US005652092A

United States Patent [19]

Vitek et al.

[11] Patent Number: 5,652,092

[45] Date of Patent: Jul. 29, 1997

[54] AMYLOID PRECURSOR PROTEINS AND METHOD OF USING SAME TO ASSESS AGENTS WHICH DOWN-REGULATE FORMATION OF β-AMYLOID PEPTIDE

[75] Inventors: Michael Peter Vitek, East Norwich, N.Y.; Jack Steven Jacobsen, Ramsey, N.J.

[73] Assignee: American Cyanamid Company, Madison, N.J.

[21] Appl. No.: 462,859

[22] Filed: Jun. 5, 1995

Related U.S. Application Data

[60] Division of Ser. No. 123,659, Sep. 20, 1993, which is a continuation-in-part of Ser. No. 877,675, May 1, 1992, abandoned.

[51] Int. Cl.[6] .......................... C07K 14/435; C12N 1/21; C12N 5/10; C12N 15/12

[52] U.S. Cl. .............................. 435/4; 435/7.1; 435/69.1; 435/172.3; 530/350; 530/839

[58] Field of Search .......................... 435/6, 4, 7.1, 69.1, 435/172.3, 240.2, 252.3, 7.2, 254.11; 436/501, 811; 530/350, 839

[56] References Cited

U.S. PATENT DOCUMENTS

| | | | |
|---|---|---|---|
| 5,348,963 | 9/1994 | Gandy | 514/313 |

FOREIGN PATENT DOCUMENTS

| | | |
|---|---|---|
| 33187/93 | 10/1993 | Australia . |
| 0447836 | 9/1991 | European Pat. Off. . |
| 0451700 | 10/1991 | European Pat. Off. . |
| WO88/03951 | 6/1988 | WIPO . |
| WO90/0154 | 2/1990 | WIPO . |
| WO90/14840 | 12/1990 | WIPO . |

OTHER PUBLICATIONS

Sahasrabudhe, S.R. et al; J. Biol. Chem. 267:25602–25608 (1992).

Vitek, M.P. et al., *Soc. Neurosci. Abstr.* 17(1–2):1443 (1991).

*Primary Examiner*—Dian C. Jacobson
*Attorney, Agent, or Firm*—Anne M. Rosenblum

[57] ABSTRACT

This application describes a purified and isolated fragment of a nucleic acid molecule encoding an amyloid precursor mutein, wherein the fragment comprises a nucleic acid sequence encoding at least one marker and a nucleic acid sequence of about 419, about 475 or about 494 amino acid residues in which a portion thereof encodes a β-amyloid protein domain. Also described is a method for screening for a compound which reduces the formation of β-amyloid protein.

7 Claims, 54 Drawing Sheets

```
Sequence Range: 1 to 8591

        10        20        30        40        50        60        70        80        90
         *         *         *         *         *         *         *         *         *
GGCGTAATCTGCTGCTTGCAAACAAAAAAACCACCGCTACCAGCGGTGGTTTGTTTGCCGGATCAAGAGCTACCAACTCTTTTTCCGAAG
CCGCATTAGACGACGAACGTTTGTTTTTTTGGTGGCGATGGTCGCCACCAAACAAACGGCCTAGTTCTCGATGGTTGAGAAAAAGGCTTC

       100       110       120       130       140       150       160       170       180
         *         *         *         *         *         *         *         *         *
GTAACTGGCTTCAGCAGAGCGCAGATACCAAATACTGTCCTTCTAGTGTAGCCGTAGTTAGGCCACCACTTCAAGAACTCTGTAGCACCG
CATTGACCGAAGTCGTCTCGCGTCTATGGTTTATGACAGGAAGATCACATCGGCATCAATCCGGTGGTGAAGTTCTTGAGACATCGTGGC

       190       200       210       220       230       240       250       260       270
         *         *         *         *         *         *         *         *         *
CCTACATACCTCGCTCTGCTAATCCTGTTACCAGTGGCTGCTGCCAGTGGCGATAAGTCGTGTCTTACCGGGTTGGACTCAAGACGATAG
GGATGTATGGAGCGAGACGATTAGGACAATGGTCACCGACGACGGTCACCGCTATTCAGCACAGAATGGCCCAACCTGAGTTCTGCTATC

       280       290       300       310       320       330       340       350       360
         *         *         *         *         *         *         *         *         *
TTACCGGATAAGGCGCAGCGGTCGGGCTGAACGGGGGGTTCGTGCACACAGCCCAGCTTGGAGCGAACGACCTACACCGAACTGAGATAC
AATGGCCTATTCCGCGTCGCCAGCCCGACTTGCCCCCCAAGCACGTGTGTCGGGTCGAACCTCGCTTGCTGGATGTGGCTTGACTCTATG

       370       380       390       400       410       420       430       440       450
         *         *         *         *         *         *         *         *         *
CTACAGCGTGAGCATTGAGAAAGCGCCACGCTTCCCGAAGGGAGAAAGGCGGACAGGTATCCGGTAAGCGGCAGGGTCGGAACAGGAGAG
GATGTCGCACTCGTAACTCTTTCGCGGTGCGAAGGGCTTCCCTCTTTCCGCCTGTCCATAGGCCATTCGCCGTCCCAGCCTTGTCCTCTC
```

FIG.7A

```
     460       470       480       490       500       510       520       530       540
       *         *         *         *         *         *         *         *         *
CGCACGAGGGAGCTTCCAGGGGGAAACGCCTGGTATCTTTATAGTCCTGTCGGGTTTCGCCACCTCTGACTTGAGCGTCGATTTTTGTGA
GCGTGCTCCCTCGAAGGTCCCCCTTTGCGGACCATAGAAATATCAGGACAGCCCAAAGCGGTGGAGACTGAACTCGCAGCTAAAAACACT

     550       560       570       580       590       600       610       620       630
       *         *         *         *         *         *         *         *         *
TGCTCGTCAGGGGGGCGGAGCCTATGGAAAAACGCCAGCAACGCAAGCTAGCTTCTAGCTAGAAATTGTAAACGTTAATATTTTGTTAAA
ACGAGCAGTCCCCCCGCCTCGGATACCTTTTTGCGGTCGTTGCGTTCGATCGAAGATCGATCTTTAACATTTGCAATTATAAAACAATTT

     640       650       660       670       680       690       700       710       720
       *         *         *         *         *         *         *         *         *
ATTCGCGTTAAATTTTTGTTAAATCAGCTCATTTTTTAACCAATAGGCCGAAATCGGCAAAATCCCTTATAAATCAAAAGAATAGCCCGA
TAAGCGCAATTTAAAAACAATTTAGTCGAGTAAAAAATTGGTTATCCGGCTTTAGCCGTTTTAGGGAATATTTAGTTTTCTTATCGGGCT

     730       740       750       760       770       780       790       800       810
       *         *         *         *         *         *         *         *         *
GATAGGGTTGAGTGTTGTTCCAGTTTGGAACAAGAGTCCACTATTAAAGAACGTGGACTCCAACGTCAAAGGGCGAAAAACCGTCTATCA
CTATCCCAACTCACAACAAGGTCAAACCTTGTTCTCAGGTGATAATTTCTTGCACCTGAGGTTGCAGTTTCCCGCTTTTTGGCAGATAGT

   820       830       840       850       860       870       880       890       900
       *         *         *         *         *         *         *         *         *
GGGCGATGGCCGCCCACTACGTGAACCATCACCCAAATCAAGTTTTTTGGGGTCGAGGTGCCGTAAAGCACTAAATCGGAACCCTAAAGG
CCCGCTACCGGCGGGTGATGCACTTGGTAGTGGGTTTAGTTCAAAAAACCCCAGCTCCACGGCATTTCGTGATTTAGCCTTGGGATTTCC
```

FIG.7B

```
     910       920       930       940       950       960       970       980       990
       *         *         *         *         *         *         *         *         *
GAGCCCCCGATTTAGAGCTTGACGGGGAAAGCCGGCGAACGTGGCGAGAAAGGAAGGGAAGAAAGCGAAAGGAGCGGGCGCTAGGGCGCT
CTCGGGGGCTAAATCTCGAACTGCCCCTTTCGGCCGCTTGCACCGCTCTTTCCTTCCCTTCTTTCGCTTTCCTCGCCCGCGATCCCGCGA

    1000      1010      1020      1030      1040      1050      1060      1070      1080
       *         *         *         *         *         *         *         *         *
GGCAAGTGTAGCGGTCACGCTGCGCGTAACCACCACACCCGCCGCGCTTAATGCGCCGCTACAGGGCGCGTACTATGGTTGCTTTGACGA
CCGTTCACATCGCCAGTGCGACGCGCATTGGTGGTGTGGGCGGCGCGAATTACGCGGCGATGTCCCGCGCATGATACCAACGAAACTGCT

    1090      1100      1110      1120      1130      1140      1150      1160      1170
       *         *         *         *         *         *         *         *         *
GACCGTATAACGTGCTTTCCTCGTTGGAATCAGAGCGGGAGCTAAACAGGAGGCCGATTAAAGGGATTTTAGACAGGAACGGTACGCCAG
CTGGCATATTGCACGAAAGGAGCAACCTTAGTCTCGCCCTCGATTTGTCCTCCGGCTAATTTCCCTAAAATCTGTCCTTGCCATGCGGTC

    1180      1190      1200      1210      1220      1230      1240      1250      1260
       *         *         *         *         *         *         *         *         *
CTGGATCACCGCGGTCTTTCTCAACGTAACACTTTACAGCGGCGCGTCATTTGATATGATGCGCCCCGCTTCCCGATAAGGGAGCAGGCC
GACCTAGTGGCGCCAGAAAGAGTTGCATTGTGAAATGTCGCCGCGCAGTAAACTATACTACGCGGGGCGAAGGGCTATTCCCTCGTCCGG

    1270      1280      1290      1300      1310      1320      1330      1340      1350
       *         *         *         *         *         *         *         *         *
AGTAAAAGCATTACCCGTGGTGGGGTTCCCGAGCGGCCAAAGGGAGCAGACTCTAAATCTGCCGTCATCGACTTCGAAGGTTCGAATCCT
TCATTTTCGTAATGGGCACCACCCCAAGGGCTCGCCGGTTTCCCTCGTCTGAGATTTAGACGGCAGTAGCTGAAGCTTCCAAGCTTAGGA

    1360      1370      1380      1390      1400      1410      1420      1430      1440
       *         *         *         *         *         *         *         *         *
TCCCCCACCACCATCACTTTCAAAAGTCCGAAAGAATCTGCTCCCTGCTTGTGTGTTGGAGGTCGCTGAGTAGTGCGCGAGTAAAATTTA
AGGGGGTGGTGGTAGTGAAAGTTTTCAGGCTTTCTTAGACGAGGGACGAACACACAACCTCCAGCGACTCATCACGCGCTCATTTTAAAT
```

FIG.7C

```
1450      1460      1470      1480      1490      1500      1510      1520      1530
   *         *         *         *         *         *         *         *         *
AGCTACAACAAGGCAAGGCTTGACCGACAATTGCATGAAGAATCTGCTTAGGGTTAGGCGTTTTGCGCTGCTTCGCGATGTACGGGCCAG
TCGATGTTGTTCCGTTCCGAACTGGCTGTTAACGTACTTCTTAGACGAATCCCAATCCGCAAAACGCGACGAAGCGCTACATGCCCGGTC

1540      1550      1560      1570      1580      1590      1600      1610      1620
   *         *         *         *         *         *         *         *         *
ATATACGCGTTGACATTGATTATTGACTAGTTATTAATAGTAATCAATTACGGGGTCATTAGTTCATAGCCCATATATGGAGTTCCGCGT
TATATGCGCAACTGTAACTAATAACTGATCAATAATTATCATTAGTTAATGCCCCAGTAATCAAGTATCGGGTATATACCTCAAGGCGCA

1630      1640      1650      1660      1670      1680      1690      1700      1710
   *         *         *         *         *         *         *         *         *
TACATAACTTACGGTAAATGGCCCGCCTGGCTGACCGCCCAACGACCCCCGCCCATTGACGTCAATAATGACGTATGTTCCCATAGTAAC
ATGTATTGAATGCCATTTACCGGGCGGACCGACTGGCGGGTTGCTGGGGGCGGGTAACTGCAGTTATTACTGCATACAAGGGTATCATTG

1720      1730      1740      1750      1760      1770      1780      1790      1800
   *         *         *         *         *         *         *         *         *
GCCAATAGGGACTTTCCATTGACGTCAATGGGTGGACTATTTACGGTAAACTGCCCACTTGGCAGTACATCAAGTGTATCATATGCCAAG
CGGTTATCCCTGAAAGGTAACTGCAGTTACCCACCTGATAAATGCCATTTGACGGGTGAACCGTCATGTAGTTCACATAGTATACGGTTC

1810      1820      1830      1840      1850      1860      1870      1880      1890
   *         *         *         *         *         *         *         *         *
TACGCCCCCTATTGACGTCAATGACGGTAAATGGCCCGCCTGGCATTATGCCCAGTACATGACCTTATGGGACTTTCCTACTTGGCAGTA
ATGCGGGGGATAACTGCAGTTACTGCCATTTACCGGGCGGACCGTAATACGGGTCATGTACTGGAATACCCTGAAAGGATGAACCGTCAT
```

FIG.7D

```
      1900      1910      1920      1930      1940      1950      1960      1970      1980
         *         *         *         *         *         *         *         *         *
CATCTACGTATTAGTCATCGCTATTACCATGGTGATGCGGTTTTGGCAGTACATCAATGGGCGTGGATAGCGGTTTGACTCACGGGGATT
GTAGATGCATAATCAGTAGCGATAATGGTACCACTACGCCAAAACCGTCATGTAGTTACCCGCACCTATCGCCAAACTGAGTGCCCCTAA

      1990      2000      2010      2020      2030      2040      2050      2060      2070
         *         *         *         *         *         *         *         *         *
TCCAAGTCTCCACCCCATTGACGTCAATGGGAGTTTGTTTTGGCACCAAAATCAACGGGACTTTCCAAAATGTCGTAACAACTCCGCCCC
AGGTTCAGAGGTGGGGTAACTGCAGTTACCCTCAAACAAAACCGTGGTTTTAGTTGCCCTGAAAGGTTTTACAGCATTGTTGAGGCGGGG

      2080      2090      2100      2110      2120      2130      2140      2150      2160
         *         *         *         *         *         *         *         *         *
ATTGACGCAAATGGGCGGTAGGCGTGTACGGTGGGAGGTCTATATAAGCAGAGCTCTCTGGCTAACTAGAGAACCCACTGCTTAACTGGC
TAACTGCGTTTACCCGCCATCCGCACATGCCACCCTCCAGATATATTCGTCTCGAGAGACCGATTGATCTCTTGGGTGACGAATTGACCG

      2170      2180      2190      2200      2210      2220      2230      2240      2250
         *         *         *         *         *         *         *         *         *
TTATCGAAATTAATACGACTCACTATAGGGAGACCGGAAGCTTGGGGATCCGCTCTAGAACTAGTGGATCCCCCGGGCTGCAGGAATTCG
AATAGCTTTAATTATGCTGAGTGATATCCCTCTGGCCTTCGAACCCCTAGGCGAGATCTTGATCACCTAGGGGGCCCGACGTCCTTAAGC

      2260      2270      2280      2290      2300      2310      2320      2330      2340
         *         *         *         *         *         *         *         *         *
GGGGGGGCAGCGGTAGGCGAGAGCACGCGGAGGAGCGTGCGCGGGGCCCCGGGAGACGGCGGCGGTGGCGGCGCGGGCAGAGCAAGGACG
CCCCCCCGTCGCCATCCGCTCTCGTGCGCCTCCTCGCACGCGCCCCGGGGCCCTCTGCCGCCGCCACCGCCGCGCCCGTCTCGTTCCTGC

      2350      2360      2370      2380      2390      2400      2410      2420      2430
         *         *         *         *         *         *         *         *         *
CGGCGGATCCCACTCGCACAGCAGCGCACTCGGTGCCCCGCGCAGGGTCGCGATGCTGCCCGGTTTGGCACTGCTCCTGCTGGCCGCCTG
GCCGCCTAGGGTGAGCGTGTCGTCGCGTGAGCCACGGGGCGCGTCCCAGCGCTACGACGGGCCAAACCGTGACGAGGACGACCGGCGGAC
                                                      M  L  P  G  L  A  L  L  L  A  A  W
```

FIG.7E

```
   2440      2450      2460      2470      2480      2490      2500      2510      2520
      *         *         *         *         *         *         *         *         *
GACGGCTCGGGCGCTGGAGGTACCCACTGATGGTAATGCTGGCCTGCTGGCTGAACCCCAGATTGCCATGTTCTGTGGCAGACTGAACAT
CTGCCGAGCCCGCGACCTCCATGGGTGACTACCATTACGACCGGACGACCGACTTGGGGTCTAACGGTACAAGACACCGTCTGACTTGTA
 T  A  R  A  L  E  V  P  T  D  G  N  A  G  L  L  A  E  P  Q  I  A  M  F  C  G  R  L  N  M

   2530      2540      2550      2560      2570      2580      2590      2600      2610
      *         *         *         *         *         *         *         *         *
GCACATGAATGTCCAGAATGGGAAGTGGGATTCAGATCCATCAGGGACCAAAACCTGCATTGATACCAAGGAAGGCATCCTGCAGTATTG
CGTGTACTTACAGGTCTTACCCTTCACCCTAAGTCTAGGTAGTCCCTGGTTTTGGACGTAACTATGGTTCCTTCCGTAGGACGTCATAAC
 H  M  N  V  Q  N  G  K  W  D  S  D  P  S  G  T  K  T  C  I  D  T  K  E  G  I  L  Q  Y  C

   2620      2630      2640      2650      2660      2670      2680      2690      2700
      *         *         *         *         *         *         *         *         *
CCAAGAAGTCTACCCTGAACTGCAGATCACCAATGTGGTAGAAGCCAACCAACCAGTGACCATCCAGAACTGGTGCAAGCGGGGCCGCAA
GGTTCTTCAGATGGGACTTGACGTCTAGTGGTTACACCATCTTCGGTTGGTTGGTCACTGGTAGGTCTTGACCACGTTCGCCCCGGCGTT
 Q  E  V  Y  P  E  L  Q  I  T  N  V  V  E  A  N  Q  P  V  T  I  Q  N  W  C  K  R  G  R  K

   2710      2720      2730      2740      2750      2760      2770      2780      2790
      *         *         *         *         *         *         *         *         *
GCAGTGCAAGACCCATCCCCACTTTGTGATTCCCTACCGCTGCTTAGTTGGTGAGTTTGTAAGTGATGCCCTTCTCGTTCCTGACAAGTG
CGTCACGTTCTGGGTAGGGGTGAAACACTAAGGGATGGCGACGAATCAACCACTCAAACATTCACTACGGGAAGAGCAAGGACTGTTCAC
 Q  C  K  T  H  P  H  F  V  I  P  Y  R  C  L  V  G  E  F  V  S  D  A  L  L  V  P  D  K  C

   2800      2810      2820      2830      2840      2850      2860      2870      2880
      *         *         *         *         *         *         *         *         *
CAAATTCTTACACCAGGAGAGGATGGATGTTTGCGAAACTCATCTTCACTGGCACACCGTCGCCAAAGAGACATGCAGTGAGAAGAGTAC
GTTTAAGAATGTGGTCCTCTCCTACCTACAAACGCTTTGAGTAGAAGTGACCGTGTGGCAGCGGTTTCTCTGTACGTCACTCTTCTCATG
 K  F  L  H  Q  E  R  M  D  V  C  E  T  H  L  H  W  H  T  V  A  K  E  T  C  S  E  K  S  T
```

FIG.7F

```
      2890      2900      2910      2920      2930      2940      2950      2960      2970
         *         *         *         *         *         *         *         *         *
CAACTTGCATGACTACGGCATGTTGCTGCCCTGCGGAATTGACAAGTTCCGAGGGGTAGAGTTTGTGTGTTGCCCACTGGCTGAAGAAAG
GTTGAACGTACTGATGCCGTACAACGACGGGACGCCTTAACTGTTCAAGGCTCCCCATCTCAAACACACAACGGGTGACCGACTTCTTTC
 N  L  H  D  Y  G  M  L  L  P  C  G  I  D  K  F  R  G  V  E  F  V  C  C  P  L  A  E  E  S

      2980      2990      3000      3010      3020      3030      3040      3050      3060
         *         *         *         *         *         *         *         *         *
TGACAATGTGGATTCTGCTGATGCGGAGGAGGATGACTCGGATGTCTGGTGGGGCGGAGCAGACACAGACTATGCAGATGGGAGTGAAGA
ACTGTTACACCTAAGACGACTACGCCTCCTCCTACTGAGCCTACAGACCACCCCGCCTCGTCTGTGTCTGATACGTCTACCCTCACTTCT
 D  N  V  D  S  A  D  A  E  E  D  D  S  D  V  W  W  G  G  A  D  T  D  Y  A  D  G  S  E  D

      3070      3080      3090      3100      3110      3120      3130      3140      3150
         *         *         *         *         *         *         *         *         *
CAAAGTAGTAGAAGTAGCAGAGGAGGAAGAAGTGGCTGAGGTGGAAGAAGAAGAAGCCGATGATGACGAGGACGATGAGGATGGTGATGA
GTTTCATCATCTTCATCGTCTCCTCCTTCTTCACCGACTCCACCTTCTTCTTCTTCGGCTACTACTGCTCCTGCTACTCCTACCACTACT
 K  V  V  E  V  A  E  E  E  E  V  A  E  V  E  E  E  E  A  D  D  D  E  D  D  E  D  G  D  E

      3160      3170      3180      3190      3200      3210      3220      3230      3240
         *         *         *         *         *         *         *         *         *
GGTAGAGGAAGAGGCTGAGGAACCCTACGAAGAAGCCACAGAGAGAACCACCAGCATTGCCACCACCACCACCACCACAGAGTCTGT
CCATCTCCTTCTCCGACTCCTTGGGATGCTTCTTCGGTGTCTCTCTTGGTGGTCGTAACGGTGGTGGTGGTGGTGGTGTCTCAGACA
 V  E  E  E  A  E  E  P  Y  E  E  A  T  E  R  T  T  S  I  A  T  T  T  T  T  T  E  S  V

      3250      3260      3270      3280      3290      3300      3310      3320      3330
         *         *         *         *         *         *         *         *         *
GGAAGAGGTGGTTCGAGAGGTGTGCTCTGAACAAGCCGAGACGGGGCCGTGCCGAGCAATGATCTCCCGCTGGTACTTTGATGTGACTGA
CCTTCTCCACCAAGCTCTCCACACGAGACTTGTTCGGCTCTGCCCCGGCACGGCTCGTTACTAGAGGGCGACCATGAAACTACACTGACT
 E  E  V  V  R  E  V  C  S  E  Q  A  E  T  G  P  C  R  A  M  I  S  R  W  Y  F  D  V  T  E
```

FIG.7G

```
      3340      3350      3360      3370      3380      3390      3400      3410      3420
         *         *         *         *         *         *         *         *         *
AGGGAAGTGTGCCCCATTCTTTTACGGCGGATGTGGCGGCAACCGGAACAACTTTGACACAGAAGAGTACTGCATGGCCGTGTGTGGCAG
TCCCTTCACACGGGGTAAGAAAATGCCGCCTACACCGCCGTTGGCCTTGTTGAAACTGTGTCTTCTCATGACGTACCGGCACACACCGTC
 G  K  C  A  P  F  F  Y  G  G  C  G  G  N  R  N  N  F  D  T  E  E  Y  C  M  A  V  C  G  S

      3430      3440      3450      3460      3470      3480      3490      3500      3510
         *         *         *         *         *         *         *         *         *
CGCCATTCCTACAACAGCAGCCAGTACCCCTGATGCCGTTGACAAGTATCTCGAGCGGCCCAAGCCCCAGCAGTTCTTTGGCCTGATGGG
GCGGTAAGGATGTTGTCGTCGGTCATGGGGACTACGGCAACTGTTCATAGAGCTCGCCGGGTTCGGGGTCGTCAAGAAACCGGACTACCC
 A  I  P  T  T  A  A  S  T  P  D  A  V  D  K  Y  L  E  R  P  K  P  Q  Q  F  F  G  L  M  G

      3520      3530      3540      3550      3560      3570      3580      3590      3600
         *         *         *         *         *         *         *         *         *
AAGCTTGACAAATATCAAGACGGAGGAGATCTCTGAAGTGAAGATGGATGCAGAATTCCGACATGACTCAGGATATGAAGTTCATCATCA
TTCGAACTGTTTATAGTTCTGCCTCCTCTAGAGACTTCACTTCTACCTACGTCTTAAGGCTGTACTGAGTCCTATACTTCAAGTAGTAGT
 S  L  T  N  I  K  T  E  E  I  S  E  V  K  M  D  A  E  F  R  H  D  S  G  Y  E  V  H  H  Q

      3610      3620      3630      3640      3650      3660      3670      3680      3690
         *         *         *         *         *         *         *         *         *
AAAATTGGTGTTCTTTGCAGAAGATGTGGGTTCAAACAAAGGTGCAATCATTGGACTCATGGTGGGCGGTGTTGTCATAGCGACAGTGAT
TTTTAACCACAAGAAACGTCTTCTACACCCAAGTTTGTTTCCACGTTAGTAACCTGAGTACCACCCGCCACAACAGTATCGCTGTCACTA
 K  L  V  F  F  A  E  D  V  G  S  N  K  G  A  I  I  G  L  M  V  G  G  V  V  I  A  T  V  I

      3700      3710      3720      3730      3740      3750      3760      3770      3780
         *         *         *         *         *         *         *         *         *
CGTCATCACCTTGGTGATGCTGAAGAAGAAACAGTACACATCCATTCATCATGGTGTGGTGGAGGTTGACGCCGCTGTCACCCCAGAGGA
GCAGTAGTGGAACCACTACGACTTCTTCTTTGTCATGTGTAGGTAAGTAGTACCACACCACCTCCAACTGCGGCGACAGTGGGGTCTCCT
 V  I  T  L  V  M  L  K  K  K  Q  Y  T  S  I  H  H  G  V  V  E  V  D  A  A  V  T  P  E  E
```

FIG.7H

```
      3790      3800      3810      3820      3830      3840      3850      3860      3870
         *         *         *         *         *         *         *         *         *
GCGCCACCTGTCCAAGATGCAGCAGAACGGCTACGAAAATCCAACCTACAAGTTCTTTGAGCAGATGCAGAACTATGGGGGCTTCATGTA
CGCGGTGGACAGGTTCTACGTCGTCTTGCCGATGCTTTTAGGTTGGATGTTCAAGAAACTCGTCTACGTCTTGATACCCCCGAAGTACAT
 R  H  L  S  K  M  Q  Q  N  G  Y  E  N  P  T  Y  K  F  F  E  Q  M  Q  N  Y  G  G  F  M  *

      3880      3890      3900      3910      3920      3930      3940      3950      3960
         *         *         *         *         *         *         *         *         *
GGATCCATATATAGGGCCCGGGTTATAATTACCTCAGGTCGACCTAGAGGGCCCTATTCTATAGTGTCACCTAAATGCTAGAGGATCTTT
CCTAGGTATATATCCCGGGCCCAATATTAATGGAGTCCAGCTGGATCTCCCGGGATAAGATATCACAGTGGATTTACGATCTCCTAGAAA

      3970      3980      3990      4000      4010      4020      4030      4040      4050
         *         *         *         *         *         *         *         *         *
GTGAAGGAACCTTACTTCTGTGGTGTGACATAATTGGACAAACTACCTACAGAGATTTAAAGCTCTAAGGTAAATATAAAATTTTTAAGT
CACTTCCTTGGAATGAAGACACCACACTGTATTAACCTGTTTGATGGATGTCTCTAAATTTCGAGATTCCATTTATATTTTAAAAATTCA

      4060      4070      4080      4090      4100      4110      4120      4130      4140
         *         *         *         *         *         *         *         *         *
GTATAATGTGTTAAACTACTGATTCTAATTGTTTGTGTATTTTAGATTCCAACCTATGGAACTGATGAATGGGAGCAGTGGTGGAATGCC
CATATTACACAATTTGATGACTAAGATTAACAAACACATAAAATCTAAGGTTGGATACCTTGACTACTTACCCTCGTCACCACCTTACGG

      4150      4160      4170      4180      4190      4200      4210      4220      4230
         *         *         *         *         *         *         *         *         *
TTTAATGAGGAAAACCTGTTTTGCTCAGAAGAAATGCCATCTAGTGATGATGAGGCTACTGCTGACTCTCAACATTCTACTCCTCCAAAA
AAATTACTCCTTTTGGACAAAACGAGTCTTCTTTACGGTAGATCACTACTACTCCGATGACGACTGAGAGTTGTAAGATGAGGAGGTTTT

      4240      4250      4260      4270      4280      4290      4300      4310      4320
         *         *         *         *         *         *         *         *         *
AAGAAGAGAAAGGTAGAAGACCCCAAGGACTTTCCTTCAGAATTGCTAAGTTTTTGAGTCATGCTGTGTTTAGTAATAGAACTCTTGCT
TTCTTCTCTTTCCATCTTCTGGGGTTCCTGAAAGGAAGTCTTAACGATTCAAAAACTCAGTACGACACAAATCATTATCTTGAGAACGA
```

FIG.7I

```
      4330      4340      4350      4360      4370      4380      4390      4400      4410
         *         *         *         *         *         *         *         *         *
TGCTTTGCTATTTACACCACAAAGGAAAAAGCTGCACTGCTATACAAGAAAATTATGGAAAAATATTTGATGTATAGTGCCTTGACTAGA
ACGAAACGATAAATGTGGTGTTTCCTTTTTCGACGTGACGATATGTTCTTTTAATACCTTTTTATAAACTACATATCACGGAACTGATCT

      4420      4430      4440      4450      4460      4470      4480      4490      4500
         *         *         *         *         *         *         *         *         *
GATCATAATCAGCCATACCACATTTGTAGAGGTTTTACTTGCTTTAAAAAACCTCCCACACCTCCCCCTGAACCTGAAACATAAAATGAA
CTAGTATTAGTCGGTATGGTGTAAACATCTCCAAAATGAACGAAATTTTTTGGAGGGTGTGGAGGGGGACTTGGACTTTGTATTTTACTT

      4510      4520      4530      4540      4550      4560      4570      4580      4590
         *         *         *         *         *         *         *         *         *
TGCAATTGTTGTTGTTAACTTGTTTATTGCAGCTTATAATGGTTACAAATAAAGCAATAGCATCACAAATTTCACAAATAAAGCATTTTT
ACGTTAACAACAACAATTGAACAAATAACGTCGAATATTACCAATGTTTATTTCGTTATCGTAGTGTTTAAAGTGTTTATTTCGTAAAAA

      4600      4610      4620      4630      4640      4650      4660      4670      4680
         *         *         *         *         *         *         *         *         *
TTCACTGCATTCTAGTTGTGGTTTGTCCAAACTCATCAATGTATCTTATCATGTCTGGATCTCCCGATCCCCTATGGTGCACTCTCAGTA
AAGTGACGTAAGATCAACACCAAACAGGTTTGAGTAGTTACATAGAATAGTACAGACCTAGAGGGCTAGGGGATACCACGTGAGAGTCAT

      4690      4700      4710      4720      4730      4740      4750      4760      4770
         *         *         *         *         *         *         *         *         *
CAATCTGCTCTGATGCCGCATAGTTAAGCCAGTATCTGCTCCCTGCTTGTGTGTTGGAGGTCGCTGAGTAGTGCGCGAGCAAAATTTAAG
GTTAGACGAGACTACGGCGTATCAATTCGGTCATAGACGAGGGACGAACACACAACCTCCAGCGACTCATCACGCGCTCGTTTTAAATTC

      4780      4790      4800      4810      4820      4830      4840      4850      4860
         *         *         *         *         *         *         *         *         *
CTACAACAAGGCAAGGCTTGACCGACAATTGCATGAAGAATCTGCTTAGGGTTAGGCGTTTTGCGCTGCTTCGCGATGTACGGGCCAGAT
GATGTTGTTCCGTTCCGAACTGGCTGTTAACGTACTTCTTAGACGAATCCCAATCCGCAAAACGCGACGAAGCGCTACATGCCCGGTCTA
```

FIG.7J

```
4870      4880      4890      4900      4910      4920      4930      4940      4950
   *         *         *         *         *         *         *         *         *
ATACGCGTATCTGAGGGGACTAGGGTGTGTTTAGGCGAAAAGCGGGGCTTCGGTTGTACGCGGTTAGGAGTCCCCTCAGGATATAGTAGT
TATGCGCATAGACTCCCCTGATCCCACACAAATCCGCTTTTCGCCCCGAAGCCAACATGCGCCAATCCTCAGGGGAGTCCTATATCATCA

4960      4970      4980      4990      5000      5010      5020      5030      5040
   *         *         *         *         *         *         *         *         *
TTCGCTTTTGCATAGGGAGGGGGAAATGTAGTCTTATGCAATACACTTGTAGTCTTGCAACATGGTAACGATGAGTTAGCAACATGCCTT
AAGCGAAAACGTATCCCTCCCCCTTTACATCAGAATACGTTATGTGAACATCAGAACGTTGTACCATTGCTACTCAATCGTTGTACGGAA

5050      5060      5070      5080      5090      5100      5110      5120      5130
   *         *         *         *         *         *         *         *         *
ACAAGGAGAGAAAAAGCACCGTGCATGCCGATTGGTGGAAGTAAGGTGGTACGATCGTGCCTTATTAGGAAGGCAACAGACAGGTCTGAC
TGTTCCTCTCTTTTTCGTGGCACGTACGGCTAACCACCTTCATTCCACCATGCTAGCACGGAATAATCCTTCCGTTGTCTGTCCAGACTG

5140      5150      5160      5170      5180      5190      5200      5210      5220
   *         *         *         *         *         *         *         *         *
ATGGATTGGACGAACCACTGAATTCCGCATTGCAGAGATAATTGTATTTAAGTGCCTAGCTCGATACAATAAACGCCATTTGACCATTCA
TACCTAACCTGCTTGGTGACTTAAGGCGTAACGTCTCTATTAACATAAATTCACGGATCGAGCTATGTTATTTGCGGTAAACTGGTAAGT

5230      5240      5250      5260      5270      5280      5290      5300      5310
   *         *         *         *         *         *         *         *         *
CCACATTGGTGTGCACCTCCTAGCTTCACGCTGCCGCAAGCACTCAGGGCGCAAGGGCTGCTAAAGGAAGCGGAACACGTAGAAAGCCAG
GGTGTAACCACACGTGGAGGATCGAAGTGCGACGGCGTTCGTGAGTCCCGCGTTCCCGACGATTTCCTTCGCCTTGTGCATCTTTCGGTC

5320      5330      5340      5350      5360      5370      5380      5390      5400
   *         *         *         *         *         *         *         *         *
TCCGCAGAAACGGTGCTGACCCCGGATGAATGTCAGCTACTGGGCTATCTGGACAAGGGAAAACGCAAGCGCAAAGAGAAAGCAGGTAGC
AGGCGTCTTTGCCACGACTGGGGCCTACTTACAGTCGATGACCCGATAGACCTGTTCCCTTTTGCGTTCGCGTTTCTCTTTCGTCCATCG
```

FIG.7K

```
         5410      5420      5430      5440      5450      5460      5470      5480      5490
            *         *         *         *         *         *         *         *         *
TTGCAGTGGGCTTACATGGCGATAGCTAGACTGGGCGGTTTTATGGACAGCAAGCGAACCGGAATTGCCAGCTGGGGCGCCCTCTGGTAA
AACGTCACCCGAATGTACCGCTATCGATCTGACCCGCCAAAATACCTGTCGTTCGCTTGGCCTTAACGGTCGACCCCGCGGGAGACCATT

         5500      5510      5520      5530      5540      5550      5560      5570      5580
            *         *         *         *         *         *         *         *         *
GGTTGGGAAGCCCTGCAAAGTAAACTGGATGGCTTTCTTGCCGCCAAGGATCTGATGGCGCAGGGGATCAAGATCTGATCAAGAGACAGG
CCAACCCTTCGGGACGTTTCATTTGACCTACCGAAAGAACGGCGGTTCCTAGACTACCGCGTCCCCTAGTTCTAGACTAGTTCTCTGTCC

         5590      5600      5610      5620      5630      5640      5650      5660      5670
            *         *         *         *         *         *         *         *         *
ATGAGGATCGTTTCGCATGATTGAACAAGATGGATTGCACGCAGGTTCTCCGGCCGCTTGGGTGGAGAGGCTATTCGGCTATGACTGGGC
TACTCCTAGCAAAGCGTACTAACTTGTTCTACCTAACGTGCGTCCAAGAGGCCGGCGAACCCACCTCTCCGATAAGCCGATACTGACCCG

         5680      5690      5700      5710      5720      5730      5740      5750      5760
            *         *         *         *         *         *         *         *         *
ACAACAGACAATCGGCTGCTCTGATGCCGCCGTGTTCCGGCTGTCAGCGCAGGGGCGCCCGGTTCTTTTTGTCAAGACCGACCTGTCCGG
TGTTGTCTGTTAGCCGACGAGACTACGGCGGCACAAGGCCGACAGTCGCGTCCCCGCGGGCCAAGAAAAACAGTTCTGGCTGGACAGGCC

         5770      5780      5790      5800      5810      5820      5830      5840      5850
            *         *         *         *         *         *         *         *         *
TGCCCTGAATGAACTGCAGGACGAGGCAGCGCGGCTATCGTGGCTGGCCACGACGGGCGTTCCTTGCGCAGCTGTGCTCGACGTTGTCAC
ACGGGACTTACTTGACGTCCTGCTCCGTCGCGCCGATAGCACCGACCGGTGCTGCCCGCAAGGAACGCGTCGACACGAGCTGCAACAGTG

         5860      5870      5880      5890      5900      5910      5920      5930      5940
            *         *         *         *         *         *         *         *         *
TGAAGCGGGAAGGGACTGGCTGCTATTGGGCGAAGTGCCGGGGCAGGATCTCCTGTCATCTCACCTTGCTCCTGCCGAGAAAGTATCCAT
ACTTCGCCCTTCCCTGACCGACGATAACCCGCTTCACGGCCCCGTCCTAGAGGACAGTAGAGTGGAACGAGGACGGCTCTTTCATAGGTA
```

FIG.7L

```
      5950      5960      5970      5980      5990      6000      6010      6020      6030
         *         *         *         *         *         *         *         *         *
CATGGCTGATGCAATGCGGCGGCTGCATACGCTTGATCCGGCTACCTGCCCATTCGACCACCAAGCGAAACATCGCATCGGCGAGCACGT
GTACCGACTACGTTACGCCGCCGACGTATGCGAACTAGGCCGATGGACGGGTAAGCTGGTGGTTCGCTTTGTAGCGTAGCCGCTCGTGCA

      6040      6050      6060      6070      6080      6090      6100      6110      6120
         *         *         *         *         *         *         *         *         *
ACTCGGATGGAAGCCGGTCTTGTCGATCAGGATGATCTGGACGAAGAGCATCAGGGGCTCGCGCCAGCCGAACTGTTCGCCAGGCTCAAG
TGAGCCTACCTTCGGCCAGAACAGCTAGTCCTACTAGACCTGCTTCTCGTAGTCCCCGAGCGCGGTCGGCTTGACAAGCGGTCCGAGTTC

      6130      6140      6150      6160      6170      6180      6190      6200      6210
         *         *         *         *         *         *         *         *         *
GCGCGCATGCCCGACGGCGAGGATCTCGTCGTGACCCATGGCGATGCCTGCTTGCCGAATATCATGGTGGAAAATGGCCGCTTTTCTGGA
CGCGCGTACGGGCTGCCGCTCCTAGAGCAGCACTGGGTACCGCTACGGACGAACGGCTTATAGTACCACCTTTTACCGGCGAAAAGACCT

      6220      6230      6240      6250      6260      6270      6280      6290      6300
         *         *         *         *         *         *         *         *         *
TTCATCGACTGTGGCCGGCTGGGTGTGGCGGACCGCTATCAGGACATAGCGTTGGCTACCCGTGATATTGCTGAAGAGCTTGGCGGCGAA
AAGTAGCTGACACCGGCCGACCCACACCGCCTGGCGATAGTCCTGTATCGCAACCGATGGGCACTATAACGACTTCTCGAACCGCCGCTT

      6310      6320      6330      6340      6350      6360      6370      6380      6390
         *         *         *         *         *         *         *         *         *
TGGGCTGACCGCTTCCTCGTGCTTTACGGTATCGCCGCTCCCGATTCGCAGCGCATCGCCTTCTATCGCCTTCTTGACGAGTTCTTCTGA
ACCCGACTGGCGAAGGAGCACGAAATGCCATAGCGGCGAGGGCTAAGCGTCGCGTAGCGGAAGATAGCGGAAGAACTGCTCAAGAAGACT

      6400      6410      6420      6430      6440      6450      6460      6470      6480
         *         *         *         *         *         *         *         *         *
GCGGGACTCTGGGGTTCGAAATGACCGACCAAGCGACGCCCAACCTGCCATCACGAGATTTCGATTCCACCGCCGCCTTCTATGAAAGGT
CGCCCTGAGACCCCAAGCTTTACTGGCTGGTTCGCTGCGGGTTGGACGGTAGTGCTCTAAAGCTAAGGTGGCGGCGGAAGATACTTTCCA
```

FIG.7M

```
      6490      6500      6510      6520      6530      6540      6550      6560      6570
         *         *         *         *         *         *         *         *         *
TGGGCTTCGGAATCGTTTTCCGGGACGCCGGCTGGATGATCCTCCAGCGCGGGGATCTCATGCTGGAGTTCTTCGCCCACCCCGGGCTCG
ACCCGAAGCCTTAGCAAAAGGCCCTGCGGCCGACCTACTAGGAGGTCGCGCCCCTAGAGTACGACCTCAAGAAGCGGGTGGGGCCCGAGC

      6580      6590      6600      6610      6620      6630      6640      6650      6660
         *         *         *         *         *         *         *         *         *
ATCCCCTCGCGAGTTGGTTCAGCTGCTGCCTGAGGCTGGACGACCTCGCGGAGTTCTACCGGCAGTGCAAATCCGTCGGCATCCAGGAAA
TAGGGGAGCGCTCAACCAAGTCGACGACGGACTCCGACCTGCTGGAGCGCCTCAAGATGGCCGTCACGTTTAGGCAGCCGTAGGTCCTTT

      6670      6680      6690      6700      6710      6720      6730      6740      6750
         *         *         *         *         *         *         *         *         *
CCAGCAGCGGCTATCCGCGCATCCATGCCCCCGAACTGCAGGAGTGGGGAGGCACGATGGCCGCTTTGGTCCCGGATCTTTGTGAAGGAA
GGTCGTCGCCGATAGGCGCGTAGGTACGGGGGCTTGACGTCCTCACCCCTCCGTGCTACCGGCGAAACCAGGGCCTAGAAACACTTCCTT

      6760      6770      6780      6790      6800      6810      6820      6830      6840
         *         *         *         *         *         *         *         *         *
CCTTACTTCTGTGGTGTGACATAATTGGACAAACTACCTACAGAGATTTAAAGCTCTAAGGTAAATATAAAATTTTTAAGTGTATAATGT
GGAATGAAGACACCACACTGTATTAACCTGTTTGATGGATGTCTCTAAATTTCGAGATTCCATTTATATTTTAAAAATTCACATATTACA

      6850      6860      6870      6880      6890      6900      6910      6920      6930
         *         *         *         *         *         *         *         *         *
GTTAAACTACTGATTCTAATTGTTTGTGTATTTTAGATTCCAACCTATGGAACTGATGAATGGGAGCAGTGGTGGAATGCCTTTAATGAG
CAATTTGATGACTAAGATTAACAAACACATAAAATCTAAGGTTGGATACCTTGACTACTTACCCTCGTCACCACCTTACGGAAATTACTC

      6940      6950      6960      6970      6980      6990      7000      7010      7020
         *         *         *         *         *         *         *         *         *
GAAAACCTGTTTTGCTCAGAAGAAATGCCATCTAGTGATGATGAGGCTACTGCTGACTCTCAACATTCTACTCCTCCAAAAAAGAAGAGA
CTTTTGGACAAAACGAGTCTTCTTTACGGTAGATCACTACTACTCCGATGACGACTGAGAGTTGTAAGATGAGGAGGTTTTTTCTTCTCT
```

FIG.7N

```
7030      7040      7050      7060      7070      7080      7090      7100      7110
   *         *         *         *         *         *         *         *         *
AAGGTAGAAGACCCCAAGGACTTTCCTTCAGAATTGCTAAGTTTTTGAGTCATGCTGTGTTTAGTAATAGAACTCTTGCTTGCTTTGCT
TTCCATCTTCTGGGGTTCCTGAAAGGAAGTCTTAACGATTCAAAAACTCAGTACGACACAAATCATTATCTTGAGAACGAACGAAACGA

7120      7130      7140      7150      7160      7170      7180      7190      7200
   *         *         *         *         *         *         *         *         *
ATTTACACCACAAAGGAAAAAGCTGCACTGCTATACAAGAAAATTATGGAAAAATATTCTGTAACCTTTATAAGTAGGCATAACAGTTAT
TAAATGTGGTGTTTCCTTTTTCGACGTGACGATATGTTCTTTTAATACCTTTTTATAAGACATTGGAAATATTCATCCGTATTGTCAATA

7210      7220      7230      7240      7250      7260      7270      7280      7290
   *         *         *         *         *         *         *         *         *
AATCATAACATACTGTTTTTTCTTACTCCACACAGGCATAGAGTGTCTGCTATTAATAACTATGCTCAAAAATTGTGTACCTTTAGCTTT
TTAGTATTGTATGACAAAAAAGAATGAGGTGTGTCCGTATCTCACAGACGATAATTATTGATACGAGTTTTTAACACATGGAAATCGAAA

7300      7310      7320      7330      7340      7350      7360      7370      7380
   *         *         *         *         *         *         *         *         *
TTAATTTGTAAAGGGGTTAATAAGGATTATTTGATGTATAGTGCCTTGACTAGAGATCATAATCAGCCATACCACATTTGTAGAGGTTTT
AATTAAACATTTCCCCAATTATTCCTAATAAACTACATATCACGGAACTGATCTCTAGTATTAGTCGGTATGGTGTAAACATCTCCAAAA

7390      7400      7410      7420      7430      7440      7450      7460      7470
   *         *         *         *         *         *         *         *         *
ACTTGCTTTAAAAAACCTCCCACACCTCCCCCTGAACCTGAAACATAAAATGAATGCAATTGTTGTTGTTAACTTGTTTATTGCAGCTTA
TGAACGAAATTTTTTGGAGGGTGTGGAGGGGGACTTGGACTTTGTATTTTACTTACGTTAACAACAACAATTGAACAAATAACGTCGAAT

7480      7490      7500      7510      7520      7530      7540      7550      7560
   *         *         *         *         *         *         *         *         *
TAATGGTTACAAATAAAGCAATAGCATCACAAATTTCACAAATAAAGCATTTTTTTCACTGCATTCTAGTTGTGGTTTGTCCAAACTCAT
ATTACCAATGTTTATTTCGTTATCGTAGTGTTTAAAGTGTTTATTTCGTAAAAAAAGTGACGTAAGATCAACACCAAACAGGTTTGAGTA
```

FIG.70

```
      7570      7580      7590      7600      7610      7620      7630      7640      7650
         *         *         *         *         *         *         *         *         *
CAATGTATCTTATCATGTCTGGATCGATCCCGCCATGGTATCAACGCCATATTTCTATTTACAGTAGGGACCTCTTCGTTGTGTAGGTAC
GTTACATAGAATAGTACAGACCTAGCTAGGGCGGTACCATAGTTGCGGTATAAAGATAAATGTCATCCCTGGAGAAGCAACACATCCATG

      7660      7670      7680      7690      7700      7710      7720      7730      7740
         *         *         *         *         *         *         *         *         *
CGCTGTATTCCTAGGGAAATAGTAGAGGCACCTTGAACTGTCTGCATCAGCCATATAGCCCCCGCTGTTCGACTTACAAACACAGGCACA
GCGACATAAGGATCCCTTTATCATCTCCGTGGAACTTGACAGACGTAGTCGGTATATCGGGGGCGACAAGCTGAATGTTTGTGTCCGTGT

      7750      7760      7770      7780      7790      7800      7810      7820      7830
         *         *         *         *         *         *         *         *         *
GTACTGACAAACCCATACACCTCCTCTGAAATACCCATAGTTGCTAGGGCTGTCTCCGAACTCATTACACCCTCCAAAGTCAGAGCTGTA
CATGACTGTTTGGGTATGTGGAGGAGACTTTATGGGTATCAACGATCCCGACAGAGGCTTGAGTAATGTGGGAGGTTTCAGTCTCGACAT

      7840      7850      7860      7870      7880      7890      7900      7910      7920
         *         *         *         *         *         *         *         *         *
ATTTCGCCATCAAGGGCAGCGAGGGCTTCTCCAGATAAAATAGCTTCTGCCGAGAGTCCCGTAAGGGTAGACACTTCAGCTAATCCCTCG
TAAAGCGGTAGTTCCCGTCGCTCCCGAAGAGGTCTATTTTATCGAAGACGGCTCTCAGGGCATTCCCATCTGTGAAGTCGATTAGGGAGC

      7930      7940      7950      7960      7970      7980      7990      8000      8010
         *         *         *         *         *         *         *         *         *
ATGAGGTCTACTAGAATAGTCAGTGCGGCTCCCATTTTGAAAATTCACTTACTTGATCAGCTTCAGAAGATGGCGGAGGGCCTCCAACAC
TACTCCAGATGATCTTATCAGTCACGCCGAGGGTAAAACTTTTAAGTGAATGAACTAGTCGAAGTCTTCTACCGCCTCCCGGAGGTTGTG

      8020      8030      8040      8050      8060      8070      8080      8090      8100
         *         *         *         *         *         *         *         *         *
AGTAATTTTCCTCCCGACTCTTAAAATAGAAAATGTCAAGTCAGTTAAGCAGGAAGTGGACTAACTGACGCAGCTGGCCGTGCGACATCC
TCATTAAAAGGAGGGCTGAGAATTTTATCTTTTACAGTTCAGTCAATTCGTCCTTCACCTGATTGACTGCGTCGACCGGCACGCTGTAGG
```

FIG.7P

```
      8110      8120      8130      8140      8150      8160      8170      8180      8190
         *         *         *         *         *         *         *         *         *
TCTTTTAATTAGTTGCTAGGCAACGCCCTCCAGAGGGCGTGTGGTTTTGCAAGAGGAAGCAAAAGCCTCTCCACCCAGGCCTAGAATGTT
AGAAAATTAATCAACGATCCGTTGCGGGAGGTCTCCCGCACACCAAAACGTTCTCCTTCGTTTTCGGAGAGGTGGGTCCGGATCTTACAA

      8200      8210      8220      8230      8240      8250      8260      8270      8280
         *         *         *         *         *         *         *         *         *
TCCACCCAATCATTACTATGACAACAGCTGTTTTTTTAGTATTAAGCAGAGGCCGGGGACCCCTGGCCCGCTTACTCTGGAGAAAAAG
AGGTGGGTTAGTAATGATACTGTTGTCGACAAAAAAATCATAATTCGTCTCCGGCCCCTGGGGACCCGGGCGAATGAGACCTCTTTTTC

      8290      8300      8310      8320      8330      8340      8350      8360      8370
         *         *         *         *         *         *         *         *         *
AAGAGAGGCATTGTAGAGGCTTCCAGAGGCAACTTGTCAAAACAGGACTGCTTCTATTTCTGTCACACTGTCTGGCCCTGTCACAAGGTC
TTCTCTCCGTAACATCTCCGAAGGTCTCCGTTGAACAGTTTTGTCCTGACGAAGATAAAGACAGTGTGACAGACCGGGACAGTGTTCCAG

      8380      8390      8400      8410      8420      8430      8440      8450      8460
         *         *         *         *         *         *         *         *         *
CAGCACCTCCATACCCCCTTTAATAAGCAGTTTGGGAACGGGTGCGGGTCTTACTCCGCCCATCCCGCCCCTAACTCCGCCCAGTTCCGC
GTCGTGGAGGTATGGGGGAAATTATTCGTCAAACCCTTGCCCACGCCCAGAATGAGGCGGGTAGGGCGGGGATTGAGGCGGGTCAAGGCG

      8470      8480      8490      8500      8510      8520      8530      8540      8550
         *         *         *         *         *         *         *         *         *
CCATTCTCCGCCCCATGGCTGACTAATTTTTTTTATTTATGCAGAGGCCGAGGCCGCCTCGGCCTCTGAGCTATTCCAGAAGTAGTGAGG
GGTAAGAGGCGGGGTACCGACTGATTAAAAAAAATAAATACGTCTCCGGCTCCGGCGGAGCCGGAGACTCGATAAGGTCTTCATCACTCC

      8560      8570      8580      8590
         *         *         *         *
AGGCTTTTTTGGAGGCCTAGGCTTTTGCAAAAAGCTAATTC
TCCGAAAAAACCTCCGGATCCGAAAACGTTTTTCGATTAAG
```

FIG.7Q

Sequence Range: 1 to 8591

```
        10        20        30        40        50        60        70        80        90
         *         *         *         *         *         *         *         *         *
GGCGTAATCTGCTGCTTGCAAACAAAAAAACCACCGCTACCAGCGGTGGTTTGTTTGCCGGATCAAGAGCTACCAACTCTTTTTCCGAAG
CCGCATTAGACGACGAACGTTTGTTTTTTTGGTGGCGATGGTCGCCACCAAACAAACGGCCTAGTTCTCGATGGTTGAGAAAAAGGCTTC

       100       110       120       130       140       150       160       170       180
         *         *         *         *         *         *         *         *         *
GTAACTGGCTTCAGCAGAGCGCAGATACCAAATACTGTCCTTCTAGTGTAGCCGTAGTTAGGCCACCACTTCAAGAACTCTGTAGCACCG
CATTGACCGAAGTCGTCTCGCGTCTATGGTTTATGACAGGAAGATCACATCGGCATCAATCCGGTGGTGAAGTTCTTGAGACATCGTGGC

       190       200       210       220       230       240       250       260       270
         *         *         *         *         *         *         *         *         *
CCTACATACCTCGCTCTGCTAATCCTGTTACCAGTGGCTGCTGCCAGTGGCGATAAGTCGTGTCTTACCGGGTTGGACTCAAGACGATAG
GGATGTATGGAGCGAGACGATTAGGACAATGGTCACCGACGACGGTCACCGCTATTCAGCACAGAATGGCCCAACCTGAGTTCTGCTATC

       280       290       300       310       320       330       340       350       360
         *         *         *         *         *         *         *         *         *
TTACCGGATAAGGCGCAGCGGTCGGGCTGAACGGGGGGTTCGTGCACACAGCCCAGCTTGGAGCGAACGACCTACACCGAACTGAGATAC
AATGGCCTATTCCGCGTCGCCAGCCCGACTTGCCCCCCAAGCACGTGTGTCGGGTCGAACCTCGCTTGCTGGATGTGGCTTGACTCTATG

       370       380       390       400       410       420       430       440       450
         *         *         *         *         *         *         *         *         *
CTACAGCGTGAGCATTGAGAAAGCGCCACGCTTCCCGAAGGGAGAAAGGCGGACAGGTATCCGGTAAGCGGCAGGGTCGGAACAGGAGAG
GATGTCGCACTCGTAACTCTTTCGCGGTGCGAAGGGCTTCCCTCTTTCCGCCTGTCCATAGGCCATTCGCCGTCCCAGCCTTGTCCTCTC
```

FIG.8A

```
        460       470       480       490       500       510       520       530       540
          *         *         *         *         *         *         *         *         *
CGCACGAGGGAGCTTCCAGGGGGAAACGCCTGGTATCTTTATAGTCCTGTCGGGTTTCGCCACCTCTGACTTGAGCGTCGATTTTTGTGA
GCGTGCTCCCTCGAAGGTCCCCCTTTGCGGACCATAGAAATATCAGGACAGCCCAAAGCGGTGGAGACTGAACTCGCAGCTAAAAACACT

        550       560       570       580       590       600       610       620       630
          *         *         *         *         *         *         *         *         *
TGCTCGTCAGGGGGGCGGAGCCTATGGAAAAACGCCAGCAACGCAAGCTAGCTTCTAGCTAGAAATTGTAAACGTTAATATTTTGTTAAA
ACGAGCAGTCCCCCCGCCTCGGATACCTTTTTGCGGTCGTTGCGTTCGATCGAAGATCGATCTTTAACATTTGCAATTATAAAACAATTT

        640       650       660       670       680       690       700       710       720
          *         *         *         *         *         *         *         *         *
ATTCGCGTTAAATTTTTGTTAAATCAGCTCATTTTTTAACCAATAGGCCGAAATCGGCAAAATCCCTTATAAATCAAAAGAATAGCCCGA
TAAGCGCAATTTAAAAACAATTTAGTCGAGTAAAAAATTGGTTATCCGGCTTTAGCCGTTTTAGGGAATATTTAGTTTTCTTATCGGGCT

        730       740       750       760       770       780       790       800       810
          *         *         *         *         *         *         *         *         *
GATAGGGTTGAGTGTTGTTCCAGTTTGGAACAAGAGTCCACTATTAAAGAACGTGGACTCCAACGTCAAAGGGCGAAAAACCGTCTATCA
CTATCCCAACTCACAACAAGGTCAAACCTTGTTCTCAGGTGATAATTTCTTGCACCTGAGGTTGCAGTTTCCCGCTTTTTGGCAGATAGT

      820       830       840       850       860       870       880       890       900
          *         *         *         *         *         *         *         *         *
GGGCGATGGCCGCCCACTACGTGAACCATCACCCAAATCAAGTTTTTTGGGGTCGAGGTGCCGTAAAGCACTAAATCGGAACCCTAAAGG
CCCGCTACCGGCGGGTGATGCACTTGGTAGTGGGTTTAGTTCAAAAAACCCCAGCTCCACGGCATTTCGTGATTTAGCCTTGGGATTTCC
```

FIG.8B

```
     910       920       930       940       950       960       970       980       990
       *         *         *         *         *         *         *         *         *
GAGCCCCCGATTTAGAGCTTGACGGGGAAAGCCGGCGAACGTGGCGAGAAAGGAAGGGAAGAAAGCGAAAGGAGCGGGCGCTAGGGCGCT
CTCGGGGGCTAAATCTCGAACTGCCCCTTTCGGCCGCTTGCACCGCTCTTTCCTTCCCTTCTTTCGCTTTCCTCGCCCGCGATCCCGCGA

    1000      1010      1020      1030      1040      1050      1060      1070      1080
       *         *         *         *         *         *         *         *         *
GGCAAGTGTAGCGGTCACGCTGCGCGTAACCACCACACCCGCCGCGCTTAATGCGCCGCTACAGGGCGCGTACTATGGTTGCTTTGACGA
CCGTTCACATCGCCAGTGCGACGCGCATTGGTGGTGTGGGCGGCGCGAATTACGCGGCGATGTCCCGCGCATGATACCAACGAAACTGCT

    1090      1100      1110      1120      1130      1140      1150      1160      1170
       *         *         *         *         *         *         *         *         *
GACCGTATAACGTGCTTTCCTCGTTGGAATCAGAGCGGGAGCTAAACAGGAGGCCGATTAAAGGGATTTTAGACAGGAACGGTACGCCAG
CTGGCATATTGCACGAAAGGAGCAACCTTAGTCTCGCCCTCGATTTGTCCTCCGGCTAATTTCCCTAAAATCTGTCCTTGCCATGCGGTC

    1180      1190      1200      1210      1220      1230      1240      1250      1260
       *         *         *         *         *         *         *         *         *
CTGGATCACCGCGGTCTTTCTCAACGTAACACTTTACAGCGGCGCGTCATTTGATATGATGCGCCCCGCTTCCCGATAAGGGAGCAGGCC
GACCTAGTGGCGCCAGAAAGAGTTGCATTGTGAAATGTCGCCGCGCAGTAAACTATACTACGCGGGGCGAAGGGCTATTCCCTCGTCCGG

    1270      1280      1290      1300      1310      1320      1330      1340      1350
       *         *         *         *         *         *         *         *         *
AGTAAAAGCATTACCCGTGGTGGGGTTCCCGAGCGGCCAAAGGGAGCAGACTCTAAATCTGCCGTCATCGACTTCGAAGGTTCGAATCCT
TCATTTTCGTAATGGGCACCACCCCAAGGGCTCGCCGGTTTCCCTCGTCTGAGATTTAGACGGCAGTAGCTGAAGCTTCCAAGCTTAGGA

    1360      1370      1380      1390      1400      1410      1420      1430      1440
       *         *         *         *         *         *         *         *         *
TCCCCCACCACCATCACTTTCAAAAGTCCGAAAGAATCTGCTCCCTGCTTGTGTGTTGGAGGTCGCTGAGTAGTGCGCGAGTAAAATTTA
AGGGGGTGGTGGTAGTGAAAGTTTTCAGGCTTTCTTAGACGAGGGACGAACACACAACCTCCAGCGACTCATCACGCGCTCATTTTAAAT
```

FIG.8C

```
    1450      1460      1470      1480      1490      1500      1510      1520      1530
       *         *         *         *         *         *         *         *         *
AGCTACAACAAGGCAAGGCTTGACCGACAATTGCATGAAGAATCTGCTTAGGGTTAGGCGTTTTGCGCTGCTTCGCGATGTACGGGCCAG
TCGATGTTGTTCCGTTCCGAACTGGCTGTTAACGTACTTCTTAGACGAATCCCAATCCGCAAAACGCGACGAAGCGCTACATGCCCGGTC

    1540      1550      1560      1570      1580      1590      1600      1610      1620
       *         *         *         *         *         *         *         *         *
ATATACGCGTTGACATTGATTATTGACTAGTTATTAATAGTAATCAATTACGGGGTCATTAGTTCATAGCCCATATATGGAGTTCCGCGT
TATATGCGCAACTGTAACTAATAACTGATCAATAATTATCATTAGTTAATGCCCCAGTAATCAAGTATCGGGTATATACCTCAAGGCGCA

    1630      1640      1650      1660      1670      1680      1690      1700      1710
       *         *         *         *         *         *         *         *         *
TACATAACTTACGGTAAATGGCCCGCCTGGCTGACCGCCCAACGACCCCCGCCCATTGACGTCAATAATGACGTATGTTCCCATAGTAAC
ATGTATTGAATGCCATTTACCGGGCGGACCGACTGGCGGGTTGCTGGGGGCGGGTAACTGCAGTTATTACTGCATACAAGGGTATCATTG

    1720      1730      1740      1750      1760      1770      1780      1790      1800
       *         *         *         *         *         *         *         *         *
GCCAATAGGGACTTTCCATTGACGTCAATGGGTGGACTATTTACGGTAAACTGCCCACTTGGCAGTACATCAAGTGTATCATATGCCAAG
CGGTTATCCCTGAAAGGTAACTGCAGTTACCCACCTGATAAATGCCATTTGACGGGTGAACCGTCATGTAGTTCACATAGTATACGGTTC

    1810      1820      1830      1840      1850      1860      1870      1880      1890
       *         *         *         *         *         *         *         *         *
TACGCCCCCTATTGACGTCAATGACGGTAAATGGCCCGCCTGGCATTATGCCCAGTACATGACCTTATGGGACTTTCCTACTTGGCAGTA
ATGCGGGGGATAACTGCAGTTACTGCCATTTACCGGGCGGACCGTAATACGGGTCATGTACTGGAATACCCTGAAAGGATGAACCGTCAT
```

FIG.8D

```
      1900      1910      1920      1930      1940      1950      1960      1970      1980
         *         *         *         *         *         *         *         *         *
CATCTACGTATTAGTCATCGCTATTACCATGGTGATGCGGTTTTGGCAGTACATCAATGGGCGTGGATAGCGGTTTGACTCACGGGGATT
GTAGATGCATAATCAGTAGCGATAATGGTACCACTACGCCAAAACCGTCATGTAGTTACCCGCACCTATCGCCAAACTGAGTGCCCCTAA

      1990      2000      2010      2020      2030      2040      2050      2060      2070
         *         *         *         *         *         *         *         *         *
TCCAAGTCTCCACCCCATTGACGTCAATGGGAGTTTGTTTTGGCACCAAAATCAACGGGACTTTCCAAAATGTCGTAACAACTCCGCCCC
AGGTTCAGAGGTGGGGTAACTGCAGTTACCCTCAAACAAAACCGTGGTTTTAGTTGCCCTGAAAGGTTTTACAGCATTGTTGAGGCGGGG

      2080      2090      2100      2110      2120      2130      2140      2150      2160
         *         *         *         *         *         *         *         *         *
ATTGACGCAAATGGGCGGTAGGCGTGTACGGTGGGAGGTCTATATAAGCAGAGCTCTCTGGCTAACTAGAGAACCCACTGCTTAACTGGC
TAACTGCGTTTACCCGCCATCCGCACATGCCACCCTCCAGATATATTCGTCTCGAGAGACCGATTGATCTCTTGGGTGACGAATTGACCG

      2170      2180      2190      2200      2210      2220      2230      2240      2250
         *         *         *         *         *         *         *         *         *
TTATCGAAATTAATACGACTCACTATAGGGAGACCGGAAGCTTGGGGATCCGCTCTAGAACTAGTGGATCCCCCGGGCTGCAGGAATTCG
AATAGCTTTAATTATGCTGAGTGATATCCCTCTGGCCTTCGAACCCCTAGGCGAGATCTTGATCACCTAGGGGGCCCGACGTCCTTAAGC

      2260      2270      2280      2290      2300      2310      2320      2330      2340
         *         *         *         *         *         *         *         *         *
GGGGGGGCAGCGGTAGGCGAGAGCACGCGGAGGAGCGTGCGCGGGGCCCCGGGAGACGGCGGCGGTGGCGGCGCGGGCAGAGCAAGGACG
CCCCCCCGTCGCCATCCGCTCTCGTGCGCCTCCTCGCACGCGCCCCGGGGCCCTCTGCCGCCGCCACCGCCGCGCCCGTCTCGTTCCTGC

      2350      2360      2370      2380      2390      2400      2410      2420      2430
         *         *         *         *         *         *         *         *         *
CGGCGGATCCCACTCGCACAGCAGCGCACTCGGTGCCCCGCGCAGGGTCGCGATGCTGCCCGGTTTGGCACTGCTCCTGCTGGCCGCCTG
GCCGCCTAGGGTGAGCGTGTCGTCGCGTGAGCCACGGGGCGCGTCCCAGCGCTACGACGGGCCAAACCGTGACGAGGACGACCGGCGGAC
                                                       M  L  P  G  L  A  L  L  L  L  A  A  W
```

FIG.8E

```
        2440      2450      2460      2470      2480      2490      2500      2510      2520
           *         *         *         *         *         *         *         *         *
GACGGCTCGGGCGCTGGAGGTACCCACTGATGGTAATGCTGGCCTGCTGGCTGAACCCCAGATTGCCATGTTCTGTGGCAGACTGAACAT
CTGCCGAGCCCGCGACCTCCATGGGTGACTACCATTACGACCGGACGACCGACTTGGGGTCTAACGGTACAAGACACCGTCTGACTTGTA
 T  A  R  A  L  E  V  P  T  D  G  N  A  G  L  L  A  E  P  Q  I  A  M  F  C  G  R  L  N  M

        2530      2540      2550      2560      2570      2580      2590      2600      2610
           *         *         *         *         *         *         *         *         *
GCACATGAATGTCCAGAATGGGAAGTGGGATTCAGATCCATCAGGGACCAAAACCTGCATTGATACCAAGGAAGGCATCCTGCAGTATTG
CGTGTACTTACAGGTCTTACCCTTCACCCTAAGTCTAGGTAGTCCCTGGTTTTGGACGTAACTATGGTTCCTTCCGTAGGACGTCATAAC
 H  M  N  V  Q  N  G  K  W  D  S  D  P  S  G  T  K  T  C  I  D  T  K  E  G  I  L  Q  Y  C

        2620      2630      2640      2650      2660      2670      2680      2690      2700
           *         *         *         *         *         *         *         *         *
CCAAGAAGTCTACCCTGAACTGCAGATCACCAATGTGGTAGAAGCCAACCAACCAGTGACCATCCAGAACTGGTGCAAGCGGGGCCGCAA
GGTTCTTCAGATGGGACTTGACGTCTAGTGGTTACACCATCTTCGGTTGGTTGGTCACTGGTAGGTCTTGACCACGTTCGCCCCGGCGTT
 Q  E  V  Y  P  E  L  Q  I  T  N  V  V  E  A  N  Q  P  V  T  I  Q  N  W  C  K  R  G  R  K

        2710      2720      2730      2740      2750      2760      2770      2780      2790
           *         *         *         *         *         *         *         *         *
GCAGTGCAAGACCCATCCCCACTTTGTGATTCCCTACCGCTGCTTAGTTGGTGAGTTTGTAAGTGATGCCCTTCTCGTTCCTGACAAGTG
CGTCACGTTCTGGGTAGGGGTGAAACACTAAGGGATGGCGACGAATCAACCACTCAAACATTCACTACGGGAAGAGCAAGGACTGTTCAC
 Q  C  K  T  H  P  H  F  V  I  P  Y  R  C  L  V  G  E  F  V  S  D  A  L  L  V  P  D  K  C

        2800      2810      2820      2830      2840      2850      2860      2870      2880
           *         *         *         *         *         *         *         *         *
CAAATTCTTACACCAGGAGAGGATGGATGTTTGCGAAACTCATCTTCACTGGCACACCGTCGCCAAAGAGACATGCAGTGAGAAGAGTAC
GTTTAAGAATGTGGTCCTCTCCTACCTACAAACGCTTTGAGTAGAAGTGACCGTGTGGCAGCGGTTTCTCTGTACGTCACTCTTCTCATG
 K  F  L  H  Q  E  R  M  D  V  C  E  T  H  L  H  W  H  T  V  A  K  E  T  C  S  E  K  S  T
```

FIG.8F

```
      2890      2900      2910      2920      2930      2940      2950      2960      2970
         *         *         *         *         *         *         *         *         *
CAACTTGCATGACTACGGCATGTTGCTGCCCTGCGGAATTGACAAGTTCCGAGGGGTAGAGTTTGTGTGTTGCCCACTGGCTGAAGAAAG
GTTGAACGTACTGATGCCGTACAACGACGGGACGCCTTAACTGTTCAAGGCTCCCCATCTCAAACACACAACGGGTGACCGACTTCTTTC
 N  L  H  D  Y  G  M  L  L  P  C  G  I  D  K  F  R  G  V  E  F  V  C  C  P  L  A  E  E  S

      2980      2990      3000      3010      3020      3030      3040      3050      3060
         *         *         *         *         *         *         *         *         *
TGACAATGTGGATTCTGCTGATGCGGAGGAGGATGACTCGGATGTCTGGTGGGGCGGAGCAGACACAGACTATGCAGATGGGAGTGAAGA
ACTGTTACACCTAAGACGACTACGCCTCCTCCTACTGAGCCTACAGACCACCCCGCCTCGTCTGTGTCTGATACGTCTACCCTCACTTCT
 D  N  V  D  S  A  D  A  E  E  D  D  S  D  V  W  W  G  G  A  D  T  D  Y  A  D  G  S  E  D

      3070      3080      3090      3100      3110      3120      3130      3140      3150
         *         *         *         *         *         *         *         *         *
CAAAGTAGTAGAAGTAGCAGAGGAGGAAGAAGTGGCTGAGGTGGAAGAAGAAGAAGCCGATGATGACGAGGACGATGAGGATGGTGATGA
GTTTCATCATCTTCATCGTCTCCTCCTTCTTCACCGACTCCACCTTCTTCTTCTTCGGCTACTACTGCTCCTGCTACTCCTACCACTACT
 K  V  V  E  V  A  E  E  E  E  V  A  E  V  E  E  E  E  A  D  D  D  E  D  D  E  D  G  D  E

      3160      3170      3180      3190      3200      3210      3220      3230      3240
         *         *         *         *         *         *         *         *         *
GGTAGAGGAAGAGGCTGAGGAACCCTACGAAGAAGCCACAGAGAGAACCACCAGCATTGCCACCACCACCACCACCACCACAGAGTCTGT
CCATCTCCTTCTCCGACTCCTTGGGATGCTTCTTCGGTGTCTCTCTTGGTGGTCGTAACGGTGGTGGTGGTGGTGGTGGTGTCTCAGACA
 V  E  E  E  A  E  E  P  Y  E  E  A  T  E  R  T  T  S  I  A  T  T  T  T  T  T  T  E  S  V

      3250      3260      3270      3280      3290      3300      3310      3320      3330
         *         *         *         *         *         *         *         *         *
GGAAGAGGTGGTTCGAGAGGTGTGCTCTGAACAAGCCGAGACGGGGCCGTGCCGAGCAATGATCTCCCGCTGGTACTTTGATGTGACTGA
CCTTCTCCACCAAGCTCTCCACACGAGACTTGTTCGGCTCTGCCCCGGCACGGCTCGTTACTAGAGGGCGACCATGAAACTACACTGACT
 E  E  V  V  R  E  V  C  S  E  Q  A  E  T  G  P  C  R  A  M  I  S  R  W  Y  F  D  V  T  E
```

FIG.8G

```
       3340      3350      3360      3370      3380      3390      3400      3410      3420
          *         *         *         *         *         *         *         *         *
AGGGAAGTGTGCCCCATTCTTTTACGGCGGATGTGGCGGCAACCGGAACAACTTTGACACAGAAGAGTACTGCATGGCCGTGTGTGGCAG
TCCCTTCACACGGGGTAAGAAAATGCCGCCTACACCGCCGTTGGCCTTGTTGAAACTGTGTCTTCTCATGACGTACCGGCACACACCGTC
 G  K  C  A  P  F  F  Y  G  G  C  G  G  N  R  N  N  F  D  T  E  E  Y  C  M  A  V  C  G  S

       3430      3440      3450      3460      3470      3480      3490      3500      3510
          *         *         *         *         *         *         *         *         *
CGCCATTCCTACAACAGCAGCCAGTACCCCTGATGCCGTTGACAAGTATCTCGAGCGGCCCAAGCCCCAGCAGTTCTTTGGCCTGATGGG
GCGGTAAGGATGTTGTCGTCGGTCATGGGGACTACGGCAACTGTTCATAGAGCTCGCCGGGTTCGGGGTCGTCAAGAAACCGGACTACCC
 A  I  P  T  T  A  A  S  T  P  D  A  V  D  K  Y  L  E  R  P  K  P  Q  Q  F  F  G  L  M  G

       3520      3530      3540      3550      3560      3570      3580      3590      3600
          *         *         *         *         *         *         *         *         *
AAGCTTGACAAATATCAAGACGGAGGAGATCTCTGAAGTGAAGATGGATGCAGAATTCCGACATGACTCAGGATATGAAGTTCATCATCA
TTCGAACTGTTTATAGTTCTGCCTCCTCTAGAGACTTCACTTCTACCTACGTCTTAAGGCTGTACTGAGTCCTATACTTCAAGTAGTAGT
 S  L  T  N  I  K  T  E  E  I  S  E  V  K  M  D  A  E  F  R  H  D  S  G  Y  E  V  H  H  Q

       3610      3620      3630      3640      3650      3660      3670      3680      3690
          *         *         *         *         *         *         *         *         *
AAAATTGGTGTTCTTTGCAGAAGATGTGGGTTCAAACAAAGGTGCAATCATTGGACTCATGGTGGGCGGTGTTGTCATAGCGACAGTGAT
TTTTAACCACAAGAAACGTCTTCTACACCCAAGTTTGTTTCCACGTTAGTAACCTGAGTACCACCCGCCACAACAGTATCGCTGTCACTA
 K  L  V  F  F  A  E  D  V  G  S  N  K  G  A  I  I  G  L  M  V  G  G  V  V  I  A  T  V  I

       3700      3710      3720      3730      3740      3750      3760      3770      3780
          *         *         *         *         *         *         *         *         *
CGTCATCACCTTGGTGATGCTGAAGAAGAAACAGTACACATCCATTCATCATGGTGTGGTGGAGGTTGACGCCGCTGTCACCCCAGAGGA
GCAGTAGTGGAACCACTACGACTTCTTCTTTGTCATGTGTAGGTAAGTAGTACCACACCACCTCCAACTGCGGCGACAGTGGGGTCTCCT
 V  I  T  L  V  M  L  K  K  K  Q  Y  T  S  I  H  H  G  V  V  E  V  D  A  A  V  T  P  E  E
```

FIG.8H

```
      3790      3800      3810      3820      3830      3840      3850      3860      3870
         *         *         *         *         *         *         *         *         *
GCGCCACCTGTCCAAGATGCAGCAGAACGGCTACGAAAATCCAACCTACAAGTTCTTTGAGCAGATGCAGAACTAGGGGGGCTTCATGTA
CGCGGTGGACAGGTTCTACGTCGTCTTGCCGATGCTTTTAGGTTGGATGTTCAAGAAACTCGTCTACGTCTTGATCCCCCCGAAGTACAT
 R  H  L  S  K  M  Q  Q  N  G  Y  E  N  P  T  Y  K  F  F  E  Q  M  Q  N  *

      3880      3890      3900      3910      3920      3930      3940      3950      3960
         *         *         *         *         *         *         *         *         *
GGATCCATATATAGGGCCCGGGTTATAATTACCTCAGGTCGACCTAGAGGGCCCTATTCTATAGTGTCACCTAAATGCTAGAGGATCTTT
CCTAGGTATATATCCCGGGCCCAATATTAATGGAGTCCAGCTGGATCTCCCGGGATAAGATATCACAGTGGATTTACGATCTCCTAGAAA

      3970      3980      3990      4000      4010      4020      4030      4040      4050
         *         *         *         *         *         *         *         *         *
GTGAAGGAACCTTACTTCTGTGGTGTGACATAATTGGACAAACTACCTACAGAGATTTAAAGCTCTAAGGTAAATATAAAATTTTTAAGT
CACTTCCTTGGAATGAAGACACCACACTGTATTAACCTGTTTGATGGATGTCTCTAAATTTCGAGATTCCATTTATATTTTAAAAATTCA

      4060      4070      4080      4090      4100      4110      4120      4130      4140
         *         *         *         *         *         *         *         *         *
GTATAATGTGTTAAACTACTGATTCTAATTGTTTGTGTATTTTAGATTCCAACCTATGGAACTGATGAATGGGAGCAGTGGTGGAATGCC
CATATTACACAATTTGATGACTAAGATTAACAAACACATAAAATCTAAGGTTGGATACCTTGACTACTTACCCTCGTCACCACCTTACGG

      4150      4160      4170      4180      4190      4200      4210      4220      4230
         *         *         *         *         *         *         *         *         *
TTTAATGAGGAAAACCTGTTTTGCTCAGAAGAAATGCCATCTAGTGATGATGAGGCTACTGCTGACTCTCAACATTCTACTCCTCCAAAA
AAATTACTCCTTTTGGACAAAACGAGTCTTCTTTACGGTAGATCACTACTACTCCGATGACGACTGAGAGTTGTAAGATGAGGAGGTTTT

      4240      4250      4260      4270      4280      4290      4300      4310      4320
         *         *         *         *         *         *         *         *         *
AAGAAGAGAAAGGTAGAAGACCCCAAGGACTTTCCTTCAGAATTGCTAAGTTTTTGAGTCATGCTGTGTTTAGTAATAGAACTCTTGCT
TTCTTCTCTTTCCATCTTCTGGGGTTCCTGAAAGGAAGTCTTAACGATTCAAAAACTCAGTACGACACAAATCATTATCTTGAGAACGA
```

FIG.8I

```
          4330      4340      4350      4360      4370      4380      4390      4400      4410
             *         *         *         *         *         *         *         *         *
TGCTTTGCTATTTACACCACAAAGGAAAAAGCTGCACTGCTATACAAGAAAATTATGGAAAAATATTTGATGTATAGTGCCTTGACTAGA
ACGAAACGATAAATGTGGTGTTTCCTTTTTCGACGTGACGATATGTTCTTTTAATACCTTTTTATAAACTACATATCACGGAACTGATCT

          4420      4430      4440      4450      4460      4470      4480      4490      4500
             *         *         *         *         *         *         *         *         *
GATCATAATCAGCCATACCACATTTGTAGAGGTTTTACTTGCTTTAAAAAACCTCCCACACCTCCCCCTGAACCTGAAACATAAAATGAA
CTAGTATTAGTCGGTATGGTGTAAACATCTCCAAAATGAACGAAATTTTTTGGAGGGTGTGGAGGGGGACTTGGACTTTGTATTTTACTT

          4510      4520      4530      4540      4550      4560      4570      4580      4590
             *         *         *         *         *         *         *         *         *
TGCAATTGTTGTTGTTAACTTGTTTATTGCAGCTTATAATGGTTACAAATAAAGCAATAGCATCACAAATTTCACAAATAAAGCATTTTT
ACGTTAACAACAACAATTGAACAAATAACGTCGAATATTACCAATGTTTATTTCGTTATCGTAGTGTTTAAAGTGTTTATTTCGTAAAAA

          4600      4610      4620      4630      4640      4650      4660      4670      4680
             *         *         *         *         *         *         *         *         *
TTCACTGCATTCTAGTTGTGGTTTGTCCAAACTCATCAATGTATCTTATCATGTCTGGATCTCCCGATCCCCTATGGTGCACTCTCAGTA
AAGTGACGTAAGATCAACACCAAACAGGTTTGAGTAGTTACATAGAATAGTACAGACCTAGAGGGCTAGGGGATACCACGTGAGAGTCAT

          4690      4700      4710      4720      4730      4740      4750      4760      4770
             *         *         *         *         *         *         *         *         *
CAATCTGCTCTGATGCCGCATAGTTAAGCCAGTATCTGCTCCCTGCTTGTGTGTTGGAGGTCGCTGAGTAGTGCGCGAGCAAAATTTAAG
GTTAGACGAGACTACGGCGTATCAATTCGGTCATAGACGAGGGACGAACACACAACCTCCAGCGACTCATCACGCGCTCGTTTTAAATTC

          4780      4790      4800      4810      4820      4830      4840      4850      4860
             *         *         *         *         *         *         *         *         *
CTACAACAAGGCAAGGCTTGACCGACAATTGCATGAAGAATCTGCTTAGGGTTAGGCGTTTTGCGCTGCTTCGCGATGTACGGGCCAGAT
GATGTTGTTCCGTTCCGAACTGGCTGTTAACGTACTTCTTAGACGAATCCCAATCCGCAAAACGCGACGAAGCGCTACATGCCCGGTCTA
```

FIG.8J

```
      4870      4880      4890      4900      4910      4920      4930      4940      4950
         *         *         *         *         *         *         *         *         *
ATACGCGTATCTGAGGGGACTAGGGTGTGTTTAGGCGAAAAGCGGGGCTTCGGTTGTACGCGGTTAGGAGTCCCCTCAGGATATAGTAGT
TATGCGCATAGACTCCCCTGATCCCACACAAATCCGCTTTTCGCCCCGAAGCCAACATGCGCCAATCCTCAGGGGAGTCCTATATCATCA

      4960      4970      4980      4990      5000      5010      5020      5030      5040
         *         *         *         *         *         *         *         *         *
TTCGCTTTTGCATAGGGAGGGGGAAATGTAGTCTTATGCAATACACTTGTAGTCTTGCAACATGGTAACGATGAGTTAGCAACATGCCTT
AAGCGAAAACGTATCCCTCCCCCTTTACATCAGAATACGTTATGTGAACATCAGAACGTTGTACCATTGCTACTCAATCGTTGTACGGAA

      5050      5060      5070      5080      5090      5100      5110      5120      5130
         *         *         *         *         *         *         *         *         *
ACAAGGAGAGAAAAAGCACCGTGCATGCCGATTGGTGGAAGTAAGGTGGTACGATCGTGCCTTATTAGGAAGGCAACAGACAGGTCTGAC
TGTTCCTCTCTTTTTCGTGGCACGTACGGCTAACCACCTTCATTCCACCATGCTAGCACGGAATAATCCTTCCGTTGTCTGTCCAGACTG

      5140      5150      5160      5170      5180      5190      5200      5210      5220
         *         *         *         *         *         *         *         *         *
ATGGATTGGACGAACCACTGAATTCCGCATTGCAGAGATAATTGTATTTAAGTGCCTAGCTCGATACAATAAACGCCATTTGACCATTCA
TACCTAACCTGCTTGGTGACTTAAGGCGTAACGTCTCTATTAACATAAATTCACGGATCGAGCTATGTTATTTGCGGTAAACTGGTAAGT

      5230      5240      5250      5260      5270      5280      5290      5300      5310
         *         *         *         *         *         *         *         *         *
CCACATTGGTGTGCACCTCCTAGCTTCACGCTGCCGCAAGCACTCAGGGCGCAAGGGCTGCTAAAGGAAGCGGAACACGTAGAAAGCCAG
GGTGTAACCACACGTGGAGGATCGAAGTGCGACGGCGTTCGTGAGTCCCGCGTTCCCGACGATTTCCTTCGCCTTGTGCATCTTTCGGTC

      5320      5330      5340      5350      5360      5370      5380      5390      5400
         *         *         *         *         *         *         *         *         *
TCCGCAGAAACGGTGCTGACCCCGGATGAATGTCAGCTACTGGGCTATCTGGACAAGGGAAAACGCAAGCGCAAAGAGAAAGCAGGTAGC
AGGCGTCTTTGCCACGACTGGGGCCTACTTACAGTCGATGACCCGATAGACCTGTTCCCTTTTGCGTTCGCGTTTCTCTTTCGTCCATCG
```

FIG.8K

```
      5410      5420      5430      5440      5450      5460      5470      5480      5490
         *         *         *         *         *         *         *         *         *
TTGCAGTGGGCTTACATGGCGATAGCTAGACTGGGCGGTTTTATGGACAGCAAGCGAACCGGAATTGCCAGCTGGGGCGCCCTCTGGTAA
AACGTCACCCGAATGTACCGCTATCGATCTGACCCGCCAAAATACCTGTCGTTCGCTTGGCCTTAACGGTCGACCCCGCGGGAGACCATT

      5500      5510      5520      5530      5540      5550      5560      5570      5580
         *         *         *         *         *         *         *         *         *
GGTTGGGAAGCCCTGCAAAGTAAACTGGATGGCTTTCTTGCCGCCAAGGATCTGATGGCGCAGGGGATCAAGATCTGATCAAGAGACAGG
CCAACCCTTCGGGACGTTTCATTTGACCTACCGAAAGAACGGCGGTTCCTAGACTACCGCGTCCCCTAGTTCTAGACTAGTTCTCTGTCC

      5590      5600      5610      5620      5630      5640      5650      5660      5670
         *         *         *         *         *         *         *         *         *
ATGAGGATCGTTTCGCATGATTGAACAAGATGGATTGCACGCAGGTTCTCCGGCCGCTTGGGTGGAGAGGCTATTCGGCTATGACTGGGC
TACTCCTAGCAAAGCGTACTAACTTGTTCTACCTAACGTGCGTCCAAGAGGCCGGCGAACCCACCTCTCCGATAAGCCGATACTGACCCG

      5680      5690      5700      5710      5720      5730      5740      5750      5760
         *         *         *         *         *         *         *         *         *
ACAACAGACAATCGGCTGCTCTGATGCCGCCGTGTTCCGGCTGTCAGCGCAGGGGCGCCCGGTTCTTTTTGTCAAGACCGACCTGTCCGG
TGTTGTCTGTTAGCCGACGAGACTACGGCGGCACAAGGCCGACAGTCGCGTCCCCGCGGGCCAAGAAAAACAGTTCTGGCTGGACAGGCC

      5770      5780      5790      5800      5810      5820      5830      5840      5850
         *         *         *         *         *         *         *         *         *
TGCCCTGAATGAACTGCAGGACGAGGCAGCGCGGCTATCGTGGCTGGCCACGACGGGCGTTCCTTGCGCAGCTGTGCTCGACGTTGTCAC
ACGGGACTTACTTGACGTCCTGCTCCGTCGCGCCGATAGCACCGACCGGTGCTGCCCGCAAGGAACGCGTCGACACGAGCTGCAACAGTG

      5860      5870      5880      5890      5900      5910      5920      5930      5940
         *         *         *         *         *         *         *         *         *
TGAAGCGGGAAGGGACTGGCTGCTATTGGGCGAAGTGCCGGGGCAGGATCTCCTGTCATCTCACCTTGCTCCTGCCGAGAAAGTATCCAT
ACTTCGCCCTTCCCTGACCGACGATAACCCGCTTCACGGCCCCGTCCTAGAGGACAGTAGAGTGGAACGAGGACGGCTCTTTCATAGGTA
```

FIG.8L

```
5950      5960      5970      5980      5990      6000      6010      6020      6030
   *         *         *         *         *         *         *         *         *
CATGGCTGATGCAATGCGGCGGCTGCATACGCTTGATCCGGCTACCTGCCCATTCGACCACCAAGCGAAACATCGCATCGGCGAGCACGT
GTACCGACTACGTTACGCCGCCGACGTATGCGAACTAGGCCGATGGACGGGTAAGCTGGTGGTTCGCTTTGTAGCGTAGCCGCTCGTGCA

6040      6050      6060      6070      6080      6090      6100      6110      6120
   *         *         *         *         *         *         *         *         *
ACTCGGATGGAAGCCGGTCTTGTCGATCAGGATGATCTGGACGAAGAGCATCAGGGGCTCGCGCCAGCCGAACTGTTCGCCAGGCTCAAG
TGAGCCTACCTTCGGCCAGAACAGCTAGTCCTACTAGACCTGCTTCTCGTAGTCCCCGAGCGCGGTCGGCTTGACAAGCGGTCCGAGTTC

6130      6140      6150      6160      6170      6180      6190      6200      6210
   *         *         *         *         *         *         *         *         *
GCGCGCATGCCCGACGGCGAGGATCTCGTCGTGACCCATGGCGATGCCTGCTTGCCGAATATCATGGTGGAAAATGGCCGCTTTTCTGGA
CGCGCGTACGGGCTGCCGCTCCTAGAGCAGCACTGGGTACCGCTACGGACGAACGGCTTATAGTACCACCTTTTACCGGCGAAAAGACCT

6220      6230      6240      6250      6260      6270      6280      6290      6300
   *         *         *         *         *         *         *         *         *
TTCATCGACTGTGGCCGGCTGGGTGTGGCGGACCGCTATCAGGACATAGCGTTGGCTACCCGTGATATTGCTGAAGAGCTTGGCGGCGAA
AAGTAGCTGACACCGGCCGACCCACACCGCCTGGCGATAGTCCTGTATCGCAACCGATGGGCACTATAACGACTTCTCGAACCGCCGCTT

6310      6320      6330      6340      6350      6360      6370      6380      6390
   *         *         *         *         *         *         *         *         *
TGGGCTGACCGCTTCCTCGTGCTTTACGGTATCGCCGCTCCCGATTCGCAGCGCATCGCCTTCTATCGCCTTCTTGACGAGTTCTTCTGA
ACCCGACTGGCGAAGGAGCACGAAATGCCATAGCGGCGAGGGCTAAGCGTCGCGTAGCGGAAGATAGCGGAAGAACTGCTCAAGAAGACT

6400      6410      6420      6430      6440      6450      6460      6470      6480
   *         *         *         *         *         *         *         *         *
GCGGGACTCTGGGGTTCGAAATGACCGACCAAGCGACGCCCAACCTGCCATCACGAGATTTCGATTCCACCGCCGCCTTCTATGAAAGGT
CGCCCTGAGACCCCAAGCTTTACTGGCTGGTTCGCTGCGGGTTGGACGGTAGTGCTCTAAAGCTAAGGTGGCGGCGGAAGATACTTTCCA
```

FIG.8M

```
      6490      6500      6510      6520      6530      6540      6550      6560      6570
         *         *         *         *         *         *         *         *         *
TGGGCTTCGGAATCGTTTTCCGGGACGCCGGCTGGATGATCCTCCAGCGCGGGGATCTCATGCTGGAGTTCTTCGCCCACCCCGGGCTCG
ACCCGAAGCCTTAGCAAAAGGCCCTGCGGCCGACCTACTAGGAGGTCGCGCCCCTAGAGTACGACCTCAAGAAGCGGGTGGGGCCCGAGC

      6580      6590      6600      6610      6620      6630      6640      6650      6660
         *         *         *         *         *         *         *         *         *
ATCCCCTCGCGAGTTGGTTCAGCTGCTGCCTGAGGCTGGACGACCTCGCGGAGTTCTACCGGCAGTGCAAATCCGTCGGCATCCAGGAAA
TAGGGGAGCGCTCAACCAAGTCGACGACGGACTCCGACCTGCTGGAGCGCCTCAAGATGGCCGTCACGTTTAGGCAGCCGTAGGTCCTTT

      6670      6680      6690      6700      6710      6720      6730      6740      6750
         *         *         *         *         *         *         *         *         *
CCAGCAGCGGCTATCCGCGCATCCATGCCCCCGAACTGCAGGAGTGGGGAGGCACGATGGCCGCTTTGGTCCCGGATCTTTGTGAAGGAA
GGTCGTCGCCGATAGGCGCGTAGGTACGGGGGCTTGACGTCCTCACCCCTCCGTGCTACCGGCGAAACCAGGGCCTAGAAACACTTCCTT

      6760      6770      6780      6790      6800      6810      6820      6830      6840
         *         *         *         *         *         *         *         *         *
CCTTACTTCTGTGGTGTGACATAATTGGACAAACTACCTACAGAGATTTAAAGCTCTAAGGTAAATATAAAATTTTTAAGTGTATAATGT
GGAATGAAGACACCACACTGTATTAACCTGTTTGATGGATGTCTCTAAATTTCGAGATTCCATTTATATTTTAAAAATTCACATATTACA

      6850      6860      6870      6880      6890      6900      6910      6920      6930
         *         *         *         *         *         *         *         *         *
GTTAAACTACTGATTCTAATTGTTTGTGTATTTTAGATTCCAACCTATGGAACTGATGAATGGGAGCAGTGGTGGAATGCCTTTAATGAG
CAATTTGATGACTAAGATTAACAAACACATAAAATCTAAGGTTGGATACCTTGACTACTTACCCTCGTCACCACCTTACGGAAATTACTC

      6940      6950      6960      6970      6980      6990      7000      7010      7020
         *         *         *         *         *         *         *         *         *
GAAAACCTGTTTTGCTCAGAAGAAATGCCATCTAGTGATGATGAGGCTACTGCTGACTCTCAACATTCTACTCCTCCAAAAAAGAAGAGA
CTTTTGGACAAAACGAGTCTTCTTTACGGTAGATCACTACTACTCCGATGACGACTGAGAGTTGTAAGATGAGGAGGTTTTTTCTTCTCT
```

FIG.8N

```
        7030      7040      7050      7060      7070      7080      7090      7100      7110
           *         *         *         *         *         *         *         *         *
AAGGTAGAAGACCCCAAGGACTTTCCTTCAGAATTGCTAAGTTTTTGAGTCATGCTGTGTTTAGTAATAGAACTCTTGCTTGCTTTGCT
TTCCATCTTCTGGGGTTCCTGAAAGGAAGTCTTAACGATTCAAAAACTCAGTACGACACAAATCATTATCTTGAGAACGAACGAAACGA

        7120      7130      7140      7150      7160      7170      7180      7190      7200
           *         *         *         *         *         *         *         *         *
ATTTACACCACAAAGGAAAAAGCTGCACTGCTATACAAGAAAATTATGGAAAAATATTCTGTAACCTTTATAAGTAGGCATAACAGTTAT
TAAATGTGGTGTTTCCTTTTTCGACGTGACGATATGTTCTTTTAATACCTTTTTATAAGACATTGGAAATATTCATCCGTATTGTCAATA

        7210      7220      7230      7240      7250      7260      7270      7280      7290
           *         *         *         *         *         *         *         *         *
AATCATAACATACTGTTTTTTCTTACTCCACACAGGCATAGAGTGTCTGCTATTAATAACTATGCTCAAAAATTGTGTACCTTTAGCTTT
TTAGTATTGTATGACAAAAAAGAATGAGGTGTGTCCGTATCTCACAGACGATAATTATTGATACGAGTTTTTAACACATGGAAATCGAAA

        7300      7310      7320      7330      7340      7350      7360      7370      7380
           *         *         *         *         *         *         *         *         *
TTAATTTGTAAAGGGGTTAATAAGGATTATTTGATGTATAGTGCCTTGACTAGAGATCATAATCAGCCATACCACATTTGTAGAGGTTTT
AATTAAACATTTCCCCAATTATTCCTAATAAACTACATATCACGGAACTGATCTCTAGTATTAGTCGGTATGGTGTAAACATCTCCAAAA

        7390      7400      7410      7420      7430      7440      7450      7460      7470
           *         *         *         *         *         *         *         *         *
ACTTGCTTTAAAAAACCTCCCACACCTCCCCCTGAACCTGAAACATAAAATGAATGCAATTGTTGTTGTTAACTTGTTTATTGCAGCTTA
TGAACGAAATTTTTTGGAGGGTGTGGAGGGGGACTTGGACTTTGTATTTTACTTACGTTAACAACAACAATTGAACAAATAACGTCGAAT

        7480      7490      7500      7510      7520      7530      7540      7550      7560
           *         *         *         *         *         *         *         *         *
TAATGGTTACAAATAAAGCAATAGCATCACAAATTTCACAAATAAAGCATTTTTTTCACTGCATTCTAGTTGTGGTTTGTCCAAACTCAT
ATTACCAATGTTTATTTCGTTATCGTAGTGTTTAAAGTGTTTATTTCGTAAAAAAAGTGACGTAAGATCAACACCAAACAGGTTTGAGTA
```

FIG.80

```
      7570      7580      7590      7600      7610      7620      7630      7640      7650
         *         *         *         *         *         *         *         *         *
CAATGTATCTTATCATGTCTGGATCGATCCCGCCATGGTATCAACGCCATATTTCTATTTACAGTAGGGACCTCTTCGTTGTGTAGGTAC
GTTACATAGAATAGTACAGACCTAGCTAGGGCGGTACCATAGTTGCGGTATAAAGATAAATGTCATCCCTGGAGAAGCAACACATCCATG

      7660      7670      7680      7690      7700      7710      7720      7730      7740
         *         *         *         *         *         *         *         *         *
CGCTGTATTCCTAGGGAAATAGTAGAGGCACCTTGAACTGTCTGCATCAGCCATATAGCCCCCGCTGTTCGACTTACAAACACAGGCACA
GCGACATAAGGATCCCTTTATCATCTCCGTGGAACTTGACAGACGTAGTCGGTATATCGGGGGCGACAAGCTGAATGTTTGTGTCCGTGT

      7750      7760      7770      7780      7790      7800      7810      7820      7830
         *         *         *         *         *         *         *         *         *
GTACTGACAAACCCATACACCTCCTCTGAAATACCCATAGTTGCTAGGGCTGTCTCCGAACTCATTACACCCTCCAAAGTCAGAGCTGTA
CATGACTGTTTGGGTATGTGGAGGAGACTTTATGGGTATCAACGATCCCGACAGAGGCTTGAGTAATGTGGGAGGTTTCAGTCTCGACAT

      7840      7850      7860      7870      7880      7890      7900      7910      7920
         *         *         *         *         *         *         *         *         *
ATTTCGCCATCAAGGGCAGCGAGGGCTTCTCCAGATAAAATAGCTTCTGCCGAGAGTCCCGTAAGGGTAGACACTTCAGCTAATCCCTCG
TAAAGCGGTAGTTCCCGTCGCTCCCGAAGAGGTCTATTTTATCGAAGACGGCTCTCAGGGCATTCCCATCTGTGAAGTCGATTAGGGAGC

      7930      7940      7950      7960      7970      7980      7990      8000      8010
         *         *         *         *         *         *         *         *         *
ATGAGGTCTACTAGAATAGTCAGTGCGGCTCCCATTTTGAAAATTCACTTACTTGATCAGCTTCAGAAGATGGCGGAGGGCCTCCAACAC
TACTCCAGATGATCTTATCAGTCACGCCGAGGGTAAAACTTTTAAGTGAATGAACTAGTCGAAGTCTTCTACCGCCTCCCGGAGGTTGTG

      8020      8030      8040      8050      8060      8070      8080      8090      8100
         *         *         *         *         *         *         *         *         *
AGTAATTTTCCTCCCGACTCTTAAAATAGAAAATGTCAAGTCAGTTAAGCAGGAAGTGGACTAACTGACGCAGCTGGCCGTGCGACATCC
TCATTAAAAGGAGGGCTGAGAATTTTATCTTTTACAGTTCAGTCAATTCGTCCTTCACCTGATTGACTGCGTCGACCGGCACGCTGTAGG
```

FIG.8P

```
      8110      8120      8130      8140      8150      8160      8170      8180      8190
         *         *         *         *         *         *         *         *         *
TCTTTTAATTAGTTGCTAGGCAACGCCCTCCAGAGGGCGTGTGGTTTTGCAAGAGGAAGCAAAAGCCTCTCCACCCAGGCCTAGAATGTT
AGAAAATTAATCAACGATCCGTTGCGGGAGGTCTCCCGCACACCAAAACGTTCTCCTTCGTTTTCGGAGAGGTGGGTCCGGATCTTACAA

      8200      8210      8220      8230      8240      8250      8260      8270      8280
         *         *         *         *         *         *         *         *         *
TCCACCCAATCATTACTATGACAACAGCTGTTTTTTTAGTATTAAGCAGAGGCCGGGGACCCCTGGCCCGCTTACTCTGGAGAAAAAG
AGGTGGGTTAGTAATGATACTGTTGTCGACAAAAAAATCATAATTCGTCTCCGGCCCCTGGGGACCCGGGCGAATGAGACCTCTTTTTC

      8290      8300      8310      8320      8330      8340      8350      8360      8370
         *         *         *         *         *         *         *         *         *
AAGAGAGGCATTGTAGAGGCTTCCAGAGGCAACTTGTCAAAACAGGACTGCTTCTATTTCTGTCACACTGTCTGGCCCTGTCACAAGGTC
TTCTCTCCGTAACATCTCCGAAGGTCTCCGTTGAACAGTTTTGTCCTGACGAAGATAAAGACAGTGTGACAGACCGGGACAGTGTTCCAG

      8380      8390      8400      8410      8420      8430      8440      8450      8460
         *         *         *         *         *         *         *         *         *
CAGCACCTCCATACCCCCTTTAATAAGCAGTTTGGGAACGGGTGCGGGTCTTACTCCGCCCATCCCGCCCCTAACTCCGCCCAGTTCCGC
GTCGTGGAGGTATGGGGGAAATTATTCGTCAAACCCTTGCCCACGCCCAGAATGAGGCGGGTAGGGCGGGGATTGAGGCGGGTCAAGGCG

      8470      8480      8490      8500      8510      8520      8530      8540      8550
         *         *         *         *         *         *         *         *         *
CCATTCTCCGCCCCATGGCTGACTAATTTTTTTTATTTATGCAGAGGCCGAGGCCGCCTCGGCCTCTGAGCTATTCCAGAAGTAGTGAGG
GGTAAGAGGCGGGGTACCGACTGATTAAAAAAAATAAATACGTCTCCGGCTCCGGCGGAGCCGGAGACTCGATAAGGTCTTCATCACTCC

      8560      8570      8580      8590
         *         *         *         *
AGGCTTTTTTGGAGGCCTAGGCTTTTGCAAAAAGCTAATTC
TCCGAAAAAACCTCCGGATCCGAAAACGTTTTTCGATTAAG
```

FIG.8Q

| 705 | 706 | 707 | 708 | 709 | 710 | 711 | 712 | 713 | 714 | 715 | 716 | 717 | 718 | 719 | 720 |
|---|---|---|---|---|---|---|---|---|---|---|---|---|---|---|---|
| K | K | K | Q | Y | T | S | I | H | H | G | V | V | E | V | D |
|  |  |  |  | A | A | A |  |  |  |  |  |  |  |  |  |

| 721 | 722 | 723 | 724 | 725 | 726 | 727 | 728 | 729 | 730 | 731 | 732 | 733 | 734 | 735 | 736 |
|---|---|---|---|---|---|---|---|---|---|---|---|---|---|---|---|
| A | A | V | T | P | E | E | R | H | L | S | K | M | Q | Q | N |
|  |  |  | A |  |  |  |  |  |  | A |  |  |  |  |  |

| 737 | 738 | 739 | 740 | 741 | 742 | 743 | 744 | 745 | 746 | 747 | 748 | 749 | 750 | 751 |
|---|---|---|---|---|---|---|---|---|---|---|---|---|---|---|
| G | Y | E | N | P | T | Y | K | F | F | E | Q | M | Q | N |
|  | A |  |  |  | A | A |  |  |  |  |  |  |  |  |

FIG. 9B

AMYLOID PRECURSOR PROTEINS AND METHOD OF USING SAME TO ASSESS AGENTS WHICH DOWN-REGULATE FORMATION OF β-AMYLOID PEPTIDE

RELATED U.S. APPLICATION DATA

This is a divisional of application Ser. No. 08/123,659 filed on Sep. 20, 1993, which is a continuation in part of application Ser. No. 07/877,675 filed on May 1, 1992, now abandoned.

BACKGROUND OF THE INVENTION

Description of the Related Art

Abnormal accumulation of extracellular amyloid in plaques and cerebrovascular deposits are characteristic in the brains of individuals suffering from Alzheimer's disease (AD) and Down's Syndrome (Glenner et al., BBRC, 120:885–890, 1984; Glenner et al., BBRC, 120:1131–1153, 1984). The amyloid deposited in these lesions, referred to as β-amyloid peptide (BAP), is a poorly soluble, self-aggregating, 39-43 amino acid (aa) protein which is derived via proteolytic cleavage from a larger amyloid precursor protein (APP) (Glenner et al., ibid.; Kang et al., Nature 325:733–736, 1987). BAP also is thought to be neurotoxic (Yankner et al., Science 245:417–420, 1990). APP is expressed as an integral transmembrane protein (Dyrks et al., Embo. J., 7:949–957, 1989) and is normally proteolytically cleaved by "secretase" (Sisodia et al., Science, 248:492–495, 1990; Esch et al., Science, 248:1122–1124) between BAP-16K (lystine) and -17L (leucine). Cleavage at this site therefore precludes amyloidogenesis (Palmert et al., BBRC, 156:432–437, 1988) and results in release of the amino-terminal APP fragment which is secreted into tissue culture medium (Sisodia et al., ibid., Esch et al., ibid.). Three major isoforms of APP (APP-695, APP-751 and APP-770) are derived by alternative splicing (Ponte et al., Nature 331.:525–527, 1988; Kitaguchi et al., Nature 331:530–532, 1988; and Tanzi et al., Nature 331:528–530, 1988) and are expressed as integral transmembrane proteins (Kang et al., Nature 325:733–736, 1987; Dyrks et al., EMBO J. 7:949–957, 1988).

Even though both APP-770 and -751 isoforms contain a protease inhibitor domain, it is the secreted portion of APP-751 (also known as Protease Nexin II (Van Nostrand et al., Science, 248:745–748, 1990) which is thought to be involved in cell adhesion (Schubert et al., Neuron, 3:689–694, 1989), remodeling during development, coagulation (Smith et al., Science, 248:1126–1128, 1990) and wound repair.

Disease related mutations in the APP gene are found either within BAP sequences or near the BAP domain. A mutation within BAP ($BAP_{E22Q}$) is found in APP of patients with hereditary cerebral hemorrhage with amyloidosis of Dutch origin (HCHWA-D), a condition in which a cerebrovascular BAP deposition is associated with stroke, and may be due to alteration in the rate of BAP aggregation (Wisniewki et al., Biochem. Biophys. Res. Commun. 179:1247–1254, 1991). A KM to NL double substitution two residues immediately N-terminal to BAP, which occurs in APP of patients with a particular form of early onset familial Alzheimer's disease (FAD), has been linked to the overproduction of BAP in tissue culture models (Citron et al., Nature 260:672–674, 1992). In another form of FAD, several mutations have been identified within the transmembrane-spanning domain of APP C-terminal to BAP at codon 717 (APP-770; V to F; I or G) (Kosik, Science 256:780–783, 1992). It has been suggested that these mutations alter normal coupling of APP to G-proteins (Nishimoto et al., Nature 362:75–79, 1993).

Although the mechanisms underlying proteolytic processing of APP are poorly understood, BAP is currently regarded to be central to the pathogenesis (Selkoe, Neuron, 6:487–498, 1991; Isiura, J. Neurochem. 56:363–369, 1991) and memory loss (Flood et al., Proc. Natl. Acad. Sci. 38:3363–3366, 1991) associated with Alzheimer's disease. It has been reported in the literature that BAP may be neurotoxic (Kowall et al., Proc. Natl. Acad. Sci. U.S.A. 88:7247–7251, 1991; Pike et al., Eur. J. Pharmacol. 207:367–368, 1991). Synthetic BAP (Yankner et al., Science 250:279–282, 1990) or purified plaques from Alzheimer's disease patients (Yankner et al., Science 245:417–420, 1989) are toxic to hippocampal cells in culture and neurons in rat brain, respectively. Recent reports suggest that BAP is involved in activation of the complement cascade leading to inflammation with potential neurotoxic consequences (Rogers et al., Proc. Natl. Acad. Sci. U.S.A. 89:10016–10020, 1992).

It has been observed that (a) amyloid plaques develop in AD brains, (b) a major component of plaques is BAP, (c) BAP is generated by proteolytic cleavage of APP protein, (d) mRNA levels of specific APP isoforms increase in AD suggesting that more APP protein is expressed, (e) APP point mutations which are thought to possibly alter normal processing have been identified in Familial AD (FAD) and "Dutch" disease, (f) injection of BAP into the brains of rodents both form lesions reminiscent of plaque pathology and result in memory deficits, and (g) plaque-like amyloid deposits have been detected in the brains of transgenic mice expressing human APP.

OBJECTS OF THE INVENTION

In accordance with the above observations, it is therefore an important object of the present invention to understand how APP is processed to generate BAP. In order to determine the processing mechanism, it is a purpose of this invention to develop a cleavable APP substrate system which represents target sequences of BAP including normal flanking regions to provide recognition sequences for processing enzymes. The utilization of a common substrate for parallel strategies involving in vitro cleavage assays using cellular extracts and in vivo processing assays in tissue culture or bacterial cells, or in conjunction with a selection system aimed at cloning BAP-cleaving proteases (or other relevant proteins) is preferred.

A second purpose of this invention is to develop an APP substrate which is non-cleavable by secretase in order to better detect other putative abnormal processing events which are hypothesized potentially either to compete with secretase for limited substrate, or to occur at much lower frequency than secretase and whose effects may be otherwise masked by the mass action of secretase.

A third purpose is to provide secretase-cleavable and secretase-noncleavable APP substrates as probes with which to investigate cellular posttranslational modifications to APP in an attempt to determine the potential influence on normal secretase and abnormal BAP "clipping" activities. These areas include, among others, the consideration of various known APP point mutations, contribution by different cell/tissue types (normal- or AD-specific), the Kunitz Protease Inhibitor domain present in APP-770 and -751 isoforms, APP phosphorylation and APP glycosylation.

A fourth purpose is to provide the ability to detect specific APP proteolytic events, either the normal secretase or the abnormal BAP-generating activities, which would enable the use of strategies which use phenotypic rescue as a marker for the cloning of potentially relevant and useful proteases in tissue culture systems.

Further purposes and objects of the present invention will appear as the specification proceeds.

SUMMARY OF THE INVENTION

The foregoing objects are accomplished by providing novel purified and isolated fragments of nucleic acid molecules which encode amyloid precursor muteins and the polypeptides encoded therefrom. Also described are host vector systems useful for the recombinant production of polypeptides in procaryotic and eucaryotic systems. Cells comprising the host vector systems of this invention as well as methods of recombinantly producing these polypeptides are provided by this invention. Further provided is a method to detect the recombinant polypeptides of this invention.

BRIEF DESCRIPTION OF THE DRAWINGS

The background of the invention and its departure from the art will be further described hereinbelow with reference to the accompanying drawings, wherein:

FIG. 7 represents the nucleotide and amino acid sequence of the APP-REP 751 protein, pCLL 602, which corresponds to Sequence I.D. Nos. 6 and 7, respectively.

FIG. 8 represents the nucleotide and amino acid sequence (corresponding to Sequence I.D. Nos. 8 and 9, respectively) of the APP-REP 751 protein, pCLL 621, which differs from pCLL 602 in the absence of the Met-enkephalin marker (ME). This protein, pCLL 621, is constructed from pCLL 602 with a stop codon introduced in pCLL 602 to eliminate the ME marker.

FIG. 9 shows the organization of APP-REP 751 (pCLL 621).

APP-REP is distinguished from endogenously expressed APP isoforms by the deletion of 276 central aa of APP and insertion of the Substance P (SP) reporter epitope (Sahasrabudhe et al., J. Biol. Chem. 267: 25602, 1992). Filled boxes, putative N-glycosylation sites; filled circles in the cytoplasmic domain, sites of the 8 potential phosphorylation sites; bars, location of epitopes for SP and 6E10 antibodies; arrow, secretase cleavage site.

FIG. 9B represents the cytoplasmic APP sequences indicating the position of alanine substitutions introduced in APP-REP (Sahasrabudhe et al., J. Biol. Chem. 267: 25602, 1992) by site-directed mutagenesis (Kunkel et al., Methods in Enzymology 154:367, 1987) to eliminate potential phosphorylation sites. Codons are identified by numbers according to APP-751 and represent sequences corresponding exactly to the cytoplasmic domain of APP. The alanine substitutions generated are referred to as Y709A, T710A, S711A, T724A, S731A, Y738A, T742A, Y743A and T710A/S711S, and correspond to Sequence I.D. Nos. 10–18, respectively. The underlined motif represent the 'NPXY' sequences putatively analogous to the internalization consensus sequence of LDL receptor (Chen et al., J. Biol. Chem. 265: 3116, 1990).

FIG. 10 shows the phorbol-induced release of APP-REP PN-II fragment. Immunoprecipitation analysis of cell lysate (0.5 mL; lanes 1–3) and CM (0.5 mL; lanes 4–6) from stable expression of APP-REP in (A) HTB14 (human glioblastoma/astrocytoma) and (B) 293 (human embryonic kidney) cells using antisera to SP (APP-REP proteins expressed in exponentially growing monolayers of adherent cells are radiolabeled by the metabolic incorporation of 0.15 mCi of $[^{35}S]$-methionine in a pulse for 15 minutes and chased for the times indicated with cold methionine; the supernatants are collected; CM and cell lysates are prepared (~$4\times10^6$ cells/10 cm culture dish/5 mL CM or lysate); immunoprecipitation, fractionation and quantitation are performed by scanning laser densitometry (Sahasrabudhe et al., J. Biol. Chem. 267: 25602, 1992)). Cells are pulsed with $[^{35}S]$-methionine, then chased for 0 (lanes 1 and 4) or 2 h (lanes 2–3 and 4–5) in the presence (lanes 2 and 6) or absence (lanes 1, 3, 4 and 5) of 1 μM PDBu. A dimethyl sulfoxide (DMSO) solution with or without phorbol dibutyrate (PDBu; Sigma) is supplemented to chase medium (final concentrations: 0.05% DMSO with or without 1 μM PDBu). For this and subsequent autoradiograms, molecular weight markers (lane M) are indicated (kDa). Expression of APP-REP initially results in the appearance of two full-length, cell-associated forms. An 'immature' ~63 kDa form precedes the conversion to a larger ~76 kDa 'mature' (i.e., posttranslationally modified) form. Subsequent cleavage of APP-REP by secretase releases a shorter ~67 kDa PN-II-like, N-terminal fragment into CM (Sahasrabudhe et al., J. Biol. Chem. 267: 25602, 1992).

Figure 11A:
Figure 11B:
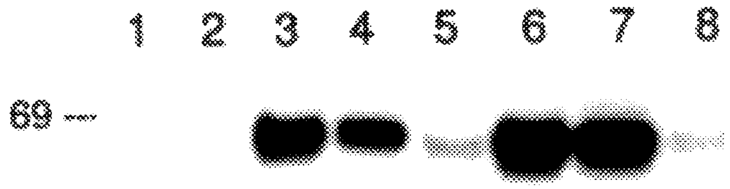

FIG. 11 shows an immunoprecipitation analysis of heterogeneous N-terminal APP-REP fragments released into CM from COS-1 cells transiently expressing APP-REP. FIG. 11*a* represents CM (0.5 mL) from cells expressing APP-REP (lane 2), a derivative containing an aa substitution Y743A (lane 3; see FIGS. 9B and 13), substrate mutant defective in cleavage by secretase (lanes 4 and 5), or vector only control (lane 1) is immunoprecipitated with SP (Lantz et al., J. Clin. Invest. 86:1396, 1990; Kishimoto et al., Science 245:1238, 1989; Downing et al., Mol. Cell. Biol. 9: 2890, 1989). FIG. 11*b* represents CM from PDBu-treated (lanes 1 and 3–5) or control (lanes 2 and 6–8) cells. APP-REP is pulsed with 0.5 mCi $[^{35}S]$-methionine for 6 h and CM (0.5 mL) immunoprecipitated with SP only (lanes 3 and 6), 6E10 only (lanes 4 and 7), 6E10 following immunodepletion of CM with SP (lanes 1 and 2, from supernatants of CM following precipitation used in lanes 3 and 6, respectively) or SP following immunodepletion of CM with 6E10 (lanes 5 and 8 from supernatants of CM following precipitation used in lanes 4 and 7, respectively). Relevant portions of the autoradiograms are shown.

Figure 12:
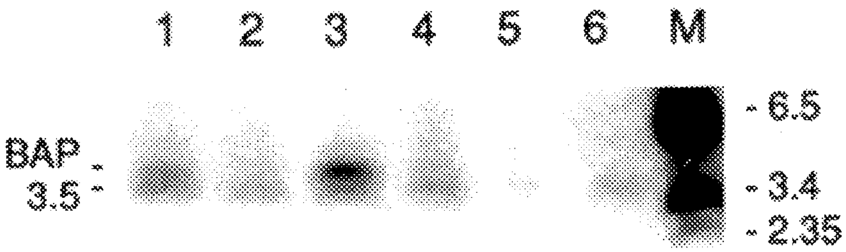

FIG. 12 shows the release of BAP into CM and effect of PDBu treatment on BAP formation. Immunoprecipitation analysis of CM from PDBu-treated (lanes 2, 4 and 5) or control (lanes 1, 3 and 6) COS-1 cells transiently expressing wild-type APP-REP (lanes 1–2), a derivative containing the Y743A substitution (lanes 3–4), or vector only control (lanes 5–6). Cells are pulsed as in FIG. 11*b* and CM (10 mL) immunoprecipitated with 6E10 antibody.

Figure 13:
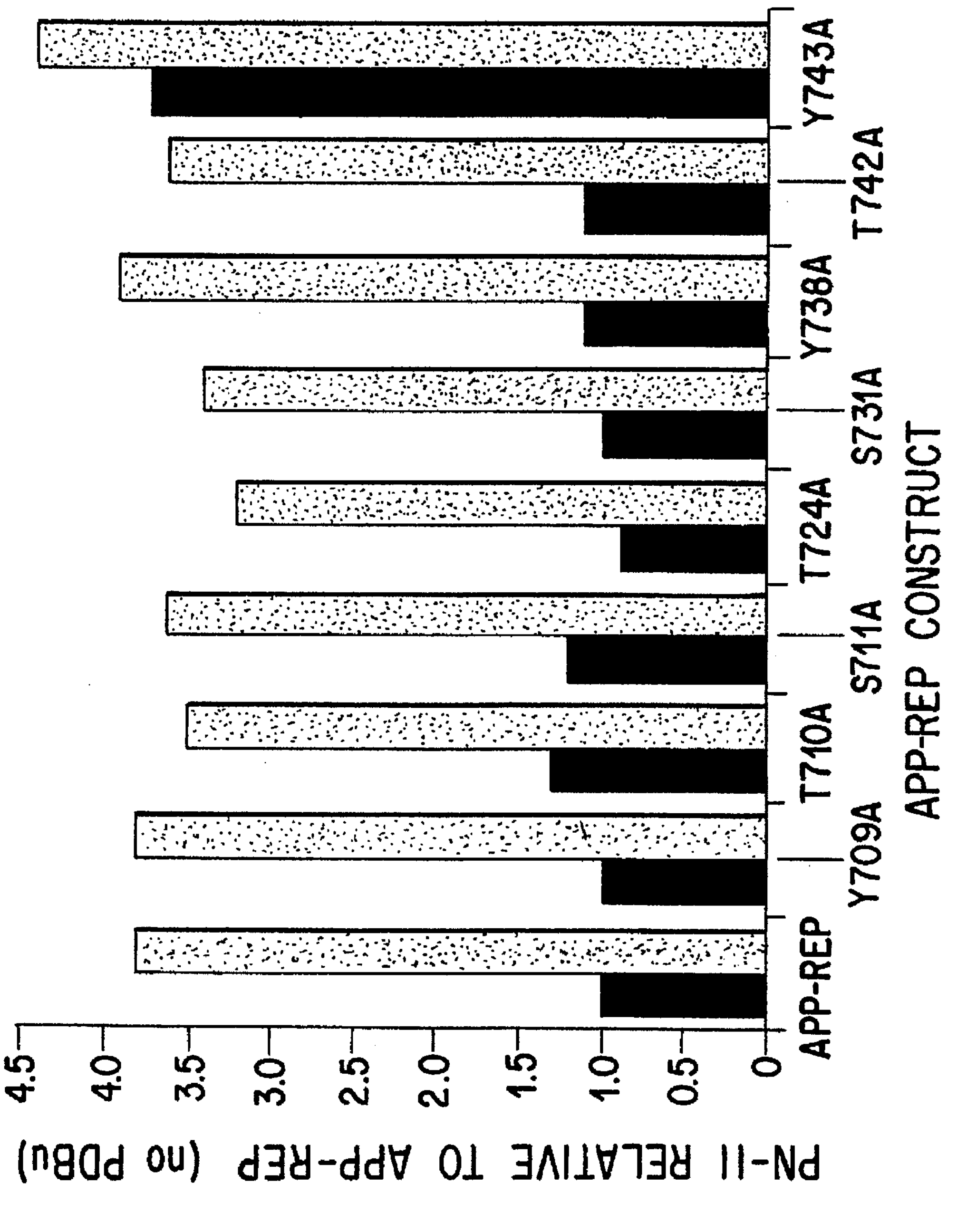

FIG. 13 shows the phorbol response in HTB14 cells stably expressing APP-REP 751 (pCLL 621) and related 'phosphorylation-minus' derivatives. Immunoprecipitation analysis of APP-REP and a panel of 'phosphorylation-minus' derivatives (FIG. 9B) stably expressed in HTB14 cells comparing treatment with PDBu and the release of PN-II. Preparation of conditioned medium (CM) and lysates and immunoprecipitation is as described above in FIG. 10B, except that APP-REP derivatives are pulsed in suspension, aliquoted and chased in the presence or absence of PDBu. For labeling of cells in suspension, cell monolayers are washed twice with 4 mL prelabeling medium (PM; methionine-free DMEM supplemented with 25 mM HEPES, pH 7.4) and incubated for 30 minutes at 37° C. to starve for methionine. Cells are then suspended by gentle trituration, pelleted, resuspended in 2 mL labeling medium (LM; PM supplemented with 2% dialyzed fetal bovine serum, GIBCO) and pulsed for 15 minutes at 37° C. with 0.15 mCi $[^{35}S]$-methionine. An excess of ice cold LM is then added and the cells are washed twice by centrifugation at 4° C. Labeled cells are then resuspended at 4° C. in 2 mL fresh chase medium (LM supplemented with 1 mM cold methionine) and incubated at 37° C. for 2 hours. Amount of PN-II is expressed in arbitrary units relative to that expressed by APP-REP control (no PDBu treatment). Control (filled bar) and 1 μM PDBu-treated (open bar) samples are indicated.

DETAILED DESCRIPTION OF THE INVENTION

In accordance with the present invention, there are provided purified and isolated fragments of nucleic acid molecules encoding amyloid precursor muteins, wherein each fragment comprises a nucleic acid sequence encoding at least one marker and a separate nucleic acid sequence of about 419, about 475 or about 494 amino acid residues in which a portion thereof encodes a β-amyloid protein domain (BAP region). In the portion which encodes the β-amyloid protein domain, the sequence may also have deleted therefrom the amino acid residues from position 11 to position 28. The fragments of the invention may include, but are not limited to, the nucleic acid molecules selected from the group consisting of pCLL602, pCLL603, pCLL604, pCLL605, pCLL606, pCLL607, pCLL608, pCLL609, pCLL610, pCLL611, pCLL612, pCLL613, pCLL621, pCLL918, pCLL919, pCLL920, pCLL962, pCLL964, pCLL987, pCLL988, pCLL989, pCLL990 and the like.

As used herein, the term "amyloid precursor mutein" is intended to encompass an amyloid precursor protein that is mutated, i.e., it is derived from a nucleic acid molecule which has changes in its primary structure as compared to wild-type amyloid precursor protein (APP). Wild-type APP exists in three isoforms. Thus, the nucleic acid molecule is changed in its primary structure for each of the three isoforms of wild-type APP. As is known to those of skill in the art, a mutation may be a substitution, deletion, or insertion of at least one nucleotide along the primary structure of the molecule. The mutations which are encompassed by this invention are the result of saturation mutagenesis in the regions of APP which are susceptible to cleavage by endoproteolytic enzymes. These mutations include deletions of nucleic acids encoding particular amino acids, substitution of nucleic acid sequences encoding one amino acid for a different amino acid and addition of nucleic acid sequences encoding additional amino acids not present in the wild type APP sequence. The term "marker" encompasses any substance capable of being detected or allowing the nucleic acid or polypeptide of this invention to be detected. Examples of markers are detectable proteins, such as enzymes or enzyme substrates and epitopes not naturally occurring in wild-type APP that are capable of forming a complex with an antibody, e.g. a polyclonal or monoclonal antibody. In the preferred embodiment of this invention, the marker is an epitope that is capable of being detected by a commercially available antibody. In one embodiment, the marker is an epitope capable of being detected by a monoolonal antibody directed to the Substance P, the Met-enkephalin or the c-myc epitope. In the most preferred embodiment of this invention, the marker is Substance P.

The term "BAP region" is defined as the region of APP wherein endoproteolytic cleavage will yield the amino-terminus and the carboxy-terminus of the BAP which is deposited as plaques and cerebrovascular amyloid in Alzheimer's disease brain. The function of the "BAP region" is to give rise to BAP which may function as a neurotoxic and/or neurotrophic agent in the brain and as other functionalities ascribed to BAP. The "BAP region" may also be endoproteolytically cleaved by enzymes. Such enzymes may include, but are not limited to, multicatalytic proteinase, propyl-endopeptidase, Cathepsin-B, Cathepsin-D, Cathepsin-L, Cathepsin-G, secretase and the like. Secretase cleaves between lysine-16 (K-16) and leucine-17 (L-17) where full-length BAP comprises the amino acid sequence DAEFRHDSGYEVHHQKLVFFAEDVGSNKGAIIGLMVGGVVIA, which corresponds to Sequence I.D. No. 19. Desirably, the nucleic acid molecule is a cDNA which encodes an RNA translated into a protein which is the substrate for endoproteolytic activities which generate BAP.

As a preferred embodiment, the deletion constructs are the APP-REP molecules having a deletion of about 276 amino acid residues from the ectodomain. The deletion of the 276 aa portion of APP distinguishes the construct of the present invention from endogenously expressed APP on the basis of size, and beneficially increases the resolution of APP-REP fragments resulting from the proteolytic cleavage by secretase or other amyloidogenic, BAP-generating cleavage events. Proteolytic cleavage of the APP-REP target substrate is determined by the electrophoretic sizing of resulting proteolytic fragments and immunological detection of APP-specific and reporter epitopes. Deletion of the large central portion of APP sequence enhances the resolution of detecting proteolytic cleavage at different positions within the APP-REP substrate protein through working with shorter, effective target substrates. Approximate location of cleavage is determined initially by fragment sizing and epitope mapping. The exact cleavage site is later determined by peptide mapping of affinity/HPLC purified fragments and sequencing of peptide ends. The APP-REP strategy described herein is an ideal model system for the expression of marked APP proteins in tissue culture cells where characterizing the proteolytic cleavage events becomes essential. Advantageously, the reporter epitope and the size of the release fragment eliminate the ambiguity which is typically encountered in the use of the endogenous or wild-type APP. The release of the PN-II fragment from endogenous APP creates substantial difficulty in correlating the fragment with the particular isoform. In the practice of the present invention, one would be able to easily determine the identity of the reporter molecule undergoing cleavage, i.e., the shorter, easily distinguishable APP-REP protein.

Surprisingly, the APP-REP protein fragment is a good representation of the naturally occurring APP with respect to post-translational synthesis, processing and stability in the tissue culture system of the present invention. Equally beneficial, markers such as Substance P and Met-enkephalin marker epitopes strategically placed on either side of BAP readily enable the immunological detection of the amino- and the carboxy-terminal fragments, respectively, which result from the proteolytic cleavage of the APP-REP substrate.

When used in conjunction with the APP-REP fragments of the present invention, the term "full-length" refers to the intact molecule where the protein product has not yet been cleaved or processed by enzymes. The full-length APP-REP constructs should be contrasted with the wild-type APP in that there are about 276 amino acid residues deleted from the wild-type sequence. For instance, the sequence for the APP-REP 770 construct consists of about 494 amino acid residues, instead of 770. Similarly, APP-REP 751 contains about 475 amino acid residues and APP-REP 695 contains about 419 amino acid residues. To be useful in the tissue culture system, the construct requires the attachment of an additional sequence which encodes at least one marker. As herein described, the plasmid pCLL602 which is based on the APP 751 isoform contains, for example, a total of 492 amino acids due to the addition of two markers, Substance P (+12 aa) and Met-enkephalin (+5 aa) (see FIG. 1). The plasmid pCLL621 which eliminates the use of the Met-enkephalin marker has a total of 487 amino acids. It should be appreciated that the plasmids pCLL602 and pCLL621 are interchangeable in the methods disclosed herein dependent upon the necessity for the Met-enkephalin marker.

Also provided by this invention is a fragment which further includes an alanine substitution at a potential phosphorylation site within the cytoplasmic domain of the amyloid precursor protein. The amyloid precursor mutein may include, but is not limited to, the group consisting of pCLL614, pCLL615, pCLL616, pCLL626, pCLL627, pCLL628, pCLL629, pCLL630 and pCLL631. The mutants can contain the alanine substitution at any one of eight potential sites of phosphorylation or a combination thereof. For example, the tyrosine in the codon positions 709 (pCLL626), 738 (pCLL627) and 743 (pCLL629) of the APP-REP derivative, based on the structure of APP 751, may be changed to alanine. Other alanine substitutions may include threonine in positions 710 (pCLL614), 724 (pCLL630) and 742 (pCLL628) as well as serine in positions 711 (pCLL615) and 731 (pCLL631). Mutants of any combination may also be prepared such as, for example, a double mutant in positions 710 (threonine) and 711 (serine) (pCLL616). It should be readily appreciated that these potential phosphorylation sites are dependent upon the particular sequence of the isoform and whether the site is accessible to substitution.

In addition, for the purposes of this invention, the nucleic acid molecule may be DNA, cDNA or RNA. However, in the most preferred embodiment of this invention, the nucleic acid is a cDNA molecule.

This invention also encompasses each of the nucleic acid molecules described hereinabove inserted into a vector so that the nucleic acid molecule may be expressed, i.e., transcribed (when the molecule is DNA) and translated into a polypeptide in both procaryotic and eucaryotic expression systems. Suitable expression vectors useful for the practice of this invention include pSVL (Pharmacia), pRCRSV (Invitrogen), pBluesoript SK$^+$ (Stratagene), pSL301 (Invitrogen), pUC19 (New England Biolabs). However, in the preferred embodiment of this invention, the vector pcDNA-1-neo is the expression vector for expression in eucaryotic cells. As is well known to those of skill in the art, the nucleic acid molecules of this invention may be operatively linked to a promoter of RNA transcription, as well as other regulatory sequences. As used herein, the term "operatively linked" means positioned in such a manner that the promoter will direct the transcription of RNA off of the nucleic acid molecule. An example of a promoter is the human cytomegalovirus promoter. The vectors of this invention preferably are capable of transcribing and/or translating nucleic acid in vitro or in vivo. The recombinant polypeptides produced from the expression of the nucleic acid molecules of this invention are also provided.

A host vector system for the production of the recombinant polypeptides described hereinabove and for expressing the nucleic acid molecules of the subject invention are provided. The host vector system comprises one of the vectors described hereinabove in a suitable host. For the purpose of the invention, a suitable host may include, but is not limited to a eucaryotic cell, e.g., a mammalian cell, a yeast cell or an insect cell for baculovirus expression. Suitable mammalian cells may comprise, but are not limited to Chinese hamster ovary cells (CHO cells; ATCC CRL 1793), African green monkey kidney COS-1 cells (ATCC CRL 1650) and human glioblastoma/astrocytoma cells (HTB14). Each of these are available from the American Type Culture. Collection (ATCC), 12301 Parklawn Drive, Rockville, Md. 20852, U.S.A. Suitable procaryotic cells may include, but are not limited to, bacteria cells, HB101 (Invitrogen), MC1061/P3 (Invitrogen) CJ236 (Invitrogen) and JM109 (Invitrogen). Accordingly, the procaryotic or eucaryotic cell comprising the vector system of this invention is further provided by this invention.

As is known to those of skill in the art, recombinant DNA technology involves insertion of specific DNA sequences into a DNA vehicle (vector) to form a recombinant DNA molecule which is capable of being replicated in a host cell. Generally, but not necessarily, the inserted DNA sequence is foreign to the recipient DNA vehicle, i.e., the inserted DNA sequence and DNA vector are derived from organisms which do not exchange genetic information in nature, or the inserted DNA sequence comprises information which may be wholly or partially artificial. Several general methods have been developed which enable construction of recombinant DNA molecules. For example, U.S. Pat. No. 4,237,224 to Cohen and Boyer describes production of such recombinant plasmids using processes of cleavage of DNA with restriction enzymes and joining the DNA pieces by known method of ligation.

These recombinant plasmids are then introduced by means of transformation or transfection and replicated in unicellular cultures including procaryotic organisms and eucaryotic organisms and euoaryotic cells grown in tissue culture. Because of the general applicability of the techniques described therein, U.S. Pat. No. 4,237,224 is hereby incorporated by reference into the present specification. Another method for introducing recombinant DNA molecules into unicellular organisms is described by Collins and Hohn in U.S. Pat. No. 4,304,863 which is also incorporated herein by reference. This method utilized a packaging, transduction system with bacteriophage vectors (cosmids).

Nucleic acid sequences may also be inserted into viruses, for example, a vaccinia virus or a baculovirus. Such recombinant viruses may be generate, for example, by transfection of plasmids into cells infected with virus, Chakrabarti et al., (1985) Mol. Cell Biol. 5:3402–3409.

Regardless of the method used for construction, the recombinant DNA molecule is preferably compatible with the host cell, i.e., capable of being replicated in the host cell either as part of the host chromosomes or as an extrachromosomal element. The recombinant DNA molecule or recombinant virus preferable has a marker function which allows the selection of the desired recombinant DNA molecule(s) or virus, e.g., baculovirus. In addition, if all of the proper replication, transcription and translation signals are correctly arranged on the recombinant DNA molecule, the foreign gene will be properly expressed in the transformed or transfected host cells.

Different genetic signals and processing events control gene expression at different levels. For instance, DNA transcription is one level, and messenger RNA (mRNA) translation is another. Transcription of DNA is dependent upon the presence of a promoter which is a DNA sequence that directs the binding of RNA polymerase and thereby promotes RNA synthesis. The DNA sequences of eucaryotic promoter differ from those of procaryotic promoters. Furthermore, eucaryotic promoters and accompanying genetic signals may not be recognized in or may not function in a procaryotic system.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno (SD) sequence on the mRNA. For a review on maximizing gene expression, see Roberts and Lauer (1979) Methods in Enzymology 68:473.

Many other factors complicate the expression of foreign genes in procaryotes even after the proper signals are inserted and appropriately positioned. One such factor is the presence of an active proteolytic system in *E. coli* and other bacteria. This protein-degrading system appears to destroy foreign proteins selectively. A tremendous utility, therefore, would be afforded by the development of a means to protect eucaryotic proteins expressed in bacteria from proteolytic degradation. One strategy is to construct hybrid genes in which the foreign sequence is ligated in. phase (i.e., in the correct reading frame) with a procaryotic structural gene. Expression of this hybrid gone results in a recombinant protein product (a protein that is a hybrid of procaryotic and foreign amino acid sequences).

Successful expression of a cloned gone requires efficient transcription of DNA, translation of the mRNA and in some instances post-translation modification of the protein. Expression vectors have been developed to increase protein production from the cloned gene. In expression vectors, the cloned gene is often placed next to a strong promoter which is controllable so that transcription can be turned on when necessary. Cells can be grown to a high density and then the promoter can be induced to increase the number of transcripts. These, if efficiency translated, will result in high yields of polypeptide. This is an especially valuable system if the foreign protein is deleterious to the host cell.

Several recombinant DNA expression systems are described below in the Experimental Procedures section for the purpose of illustration only, and these examples should not be construed to limit the scope of the present invention.

A method for producing a recombinant polypeptide described hereinabove, is also provided. This method comprises growing the host cell containing the nucleic acid of this invention and/or the host vector system of this invention under suitable conditions, permitting production of the polypeptide and recovering the resulting recombinant polypeptide produced.

A method of detecting in a sample the presence of any of the recombinant polypeptides described hereinabove is further provided by this invention. In the preferred embodiment of this invention, the marker is an epitope directed against an antibody, the epitope of which is not present in the wild-type polypeptide or APP derivative. This method comprises obtaining a sample suspected of containing the polypeptide and contacting the sample with an antibody directed to the marker. The contacting is done under suitable conditions to favor the formation of an antibody-epitope (i.e., antigen) complex, and detecting the presence of any complex so formed. The presence of complex being a positive indication that the recombinant polypeptide is in the sample. In one embodiment of this invention, the antibody is a mouse antibody. In another embodiment of this invention, the antibody is a rabbit antibody. In the most preferred embodiment, the mouse or rabbit antibody is either a monoclonal or polyclonal antibody.

The antibody is labeled with a detectable marker selected from the group consisting of radioisotopes, dyes, enzymes and biotin. For the purposes of this invention, suitable radioisotopes include, but are not limited to, $^{32}P$, $^{35}S$, $^{3}H$, $^{131}I$ and $^{125}I$.

Suitable samples for the practice of this invention include, but are not limited to, conditioned media, cell lysates and cellular organelle fractions.

The method of this invention may utilize the recombinant polypeptide for the detection of drugs or compounds that inhibit or augment the activity of proteolytic enzymes which cleave APP to generate BAP fragments. For the purposes of example only, a recombinant polypeptide which contains a Substance-P marker epitope on the amino-terminal side of BAP and a Met-enkephalin marker epitope on the carboxy-terminal side of BAP. Using commercially available RIA kits (Peninsula), one can measure the amount of amino-marker and carboxy-marker in any given sample. Since endoproteolytic activity is shown (see FIG. 3) to allow the release of amino-terminal fragments of APP containing the amino-marker into the conditioned media while carboxy-terminal APP fragments containing the carboxy-marker remain associated with the cell, then RIA which measure the amount of amino-marker in the conditioned medium as a direct result of endoproteolytic cleavage activity between the marker epitopes preferable within the "BAP region". Using this RIA to the amino-marker, the effect of potential drugs designed to modify endoprotease activity can be tested comparing the level of amino-marker in untreated and endoprotease-inhibitor treated samples. If a difference in non-treated and treated samples is found, then the position of the cleavage or lack of cleavage can be verified as with the procedures used in FIGS. 3 to 6. Thus, the qualitative and quantitative aspects of endoproteolytic activity and its inhibition on the recombinant APP mutein is evaluated. The amino-marker may also be an enzyme such as alkaline phosphatase or β-galactosidase which would be released into the conditioned media by the action of a suitable endoprotease. Cell free samples of conditioned media containing the liberated enzyme converts a chromogenic substrate into the appropriately colored product (blue for X-Gal and yellow for ONPG) which is subsequently measured spectrophotometrically. Inhibitors of the appropriate endoprotease would suppress the release of the β-galactosidase enzyme into the conditioned medium resulting in a less colored product being observed.

Overview of the APP-REP Strategy

To study secretase and BAP-generating pathways, portions of APP cDNA clones are used to engineer a panel of APP-REPorter (APP-REP) plasmids to express "marked" proteins representing each of the APP isoforms (and other APP/BAP sequence alterations; see below) in cultured cells. The system utilizes the marker Substance-P (SP) and Met-Enkephalin (ME) which are strategically placed, respectively, on amino- and carboxy-terminal sides of BAP. Proteolytic cleavage of APP-REP target substrate is determined by the electrophoretic sizing of resulting proteolytic fragments and immunological detection of APP-specific and SP and ME reporter epitopes. Deletion of a large central portion of APP sequence also makes APP-REP readily distinguishable from the endogenous APP isoforms based on size. Moreover, the resolution of detecting proteolytic cleavage at different positions within the APP-REP substrate protein is enhanced by working with shorter target substrates. Approximate location of cleavage is determined initially by fragment sizing and epitope mapping; the exact cleavage site is later determined by peptide mapping of affinity/HPLC purified fragments and sequencing of peptide ends.

Plasmids also are derived from these constructs for developing similar strategies to express APP-REP protein in cell free reticulocyte transcription-translation and bacterial systems. Mutation of APP-REP secretase/BAPase cleavage site (by sequence substitution, deletion or FAD mutations) can reveal putative proteolytic activities associated with BAP formation including amino- and carboxy-BAPase activities which are predicted to result in altered product fragments lengths.

The plasmids, DNA sequences and microorganisms deposited in connection with the present patent application, except where specified to the contrary, are deposited in American Cyanamid Company's culture collection maintained at Lederle Laboratories in Pearl River, N.Y. and are deposited pursuant to the Budapest Treaty with the American Type Culture Collection (ATCC), 12301 Parklawn Drive, Rockville, Md. 20852, U.S.A.

Generally, the plasmids of the present invention are derived from pCLL602 and pCLL621. The *E. coli* bacterial strains which have been deposited in the ATCC on Aug. 27, 1993 include the strains carrying the expression vectors and reporter plasmids pCLL602 (ATCC 69405) and pCLL621 (ATCC 69406).

The plasmid pCLL602 consists of a full-length APP-REP 751 (XbaI-SalI fragment) containing the MET-enkephalin reporter epitope at the C-terminus of APP which is subcloned into eucaryotic expression vector. APP-REP 751 (pCLL602) is constructed by ligating restriction fragments representing N- and C-terminal sequences of APP-751 cDNA and Substance P reporter epitope sequences (Sahasrabudhe et al., J. Biol. Chem. 267:25602–25608, 1992). Essentially, an EcoRI-XhoI fragment encoding N-terminal APP-751 sequences is ligated to a short synthetic XhoI-HindIII fragment encoding Substance P (aa 1–11). The larger EcoRI-HindIII product is then ligated to a PCR amplified HindIII-SalI fragment representing C-terminal APP sequences (a portion of APP ectodomain, BAP, transmembrance and cytoplasmic APP sequences). The full-length APP-REP 751 (pCLL602) fragment is then subcloned into the SV40-based, CMV promoter driven, eucaryotic expression vector pcDNA-1-neo (pCLL601).

The plasmid pCLL621 consists of a full-length APP-REP 751 which is derived from plasmid pCLL602 with the elimination of the C-terminal MET-enkephalin reporter epitope. By site-directed mutagenesis, a stop codon is introduced immediately following the C-terminus of endogenous APP sequences.

Other plasmids of the present invention may be constructed using site-directed mutagenesis and the techniques described herein. As one example, for the plasmid pCLL935 (see Table I), N-terminal cassettes provide the APP-751 isoform (EcoRI-XhoI fragment) plus 11 aa of Substance P epitope marker (synthetic XhoI-HindIII fragment) in a pSK (+) vector. As another example, for the plasmid pCLL947 (see Table I), C-terminal cassettes provide BAP containing wild-type or mutated sequences and the cytoplasmic domain of APP including the MET-enkephalin reporter epitope (ECoRI-BamHI fragment) in a pSL301 vector. As a third example, full-length APP-REP is constructed in the bacterial cloning vector pSK(+) to form the plasmid pCLL964 (see Table II).

For the construction of the alanine substitution mutations, the alanine substitution mutations are introduced into APP-REP 751 (pCLL621) by site-directed mutagenesis. Briefly, single-stranded phagemid pCLL621 DNA is prepared in CJ236/p3 by infection with helper phage M13K07 and used as template on which oligonucleotide primers encoding APP sequences with the desired alanine mutations are annealed and elongated. The alanine substitutions may be engineered at any one of the eight sites of phosphorylation or a combination thereof (see FIGS. 9A and 9B). Examples of alanine substitutions would include, but are not limited to, tyrosine at positions 709 (pCLL626), 738 (pCLL627) and 743 (pCLL629); threonine at positions 710 (pCLL614), 724 (pCLL630) and 742 (pCLL628); serine at positions 711 (pCLL615) and 731 (pCLL631); and combinations thereof (e.g., a double mutant in positions 710 (threonine) and 711 (serine) (pCLL616)).

Bacterial Strains and Transformation

Transformation of commercially available frozen competent bacteria, maintenance and selection of transformants is according to the manufacturer. Strains HB101, DH5a or JM109 (Gibco-BRL) are used for the construction of APP-REP in pSK(+) (Stratagene, La Jolla, Calif.) and pSL 301 (Invitrogen, San Diego, Calif.). APP-REP is subsequently subcloned into the eucaryotic expression vector pcDNA-1-neo and amplified in MC1061/P3 (Invitrogen, San Diego, Calif).

Plasmid Construction

Figure 1:
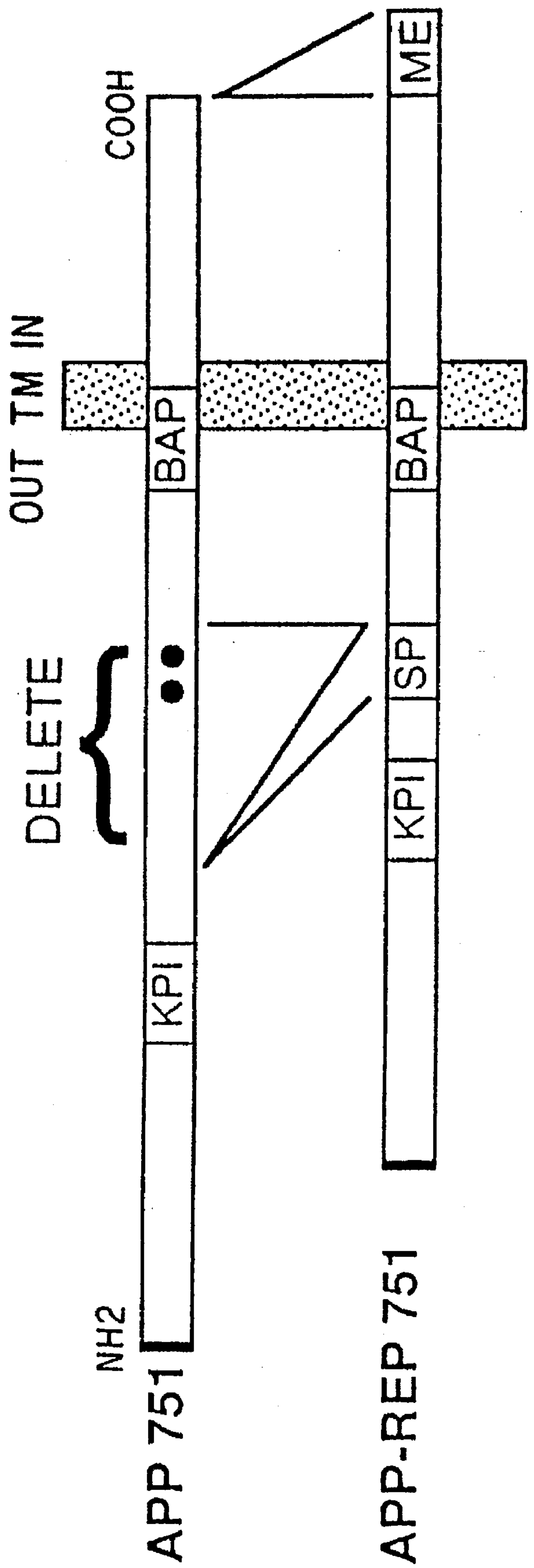
FIG. 1 shows a schematic representation of APP-REP 751 (pCLL 602). APP-REP 751 represents a cleavable APP substrate system which contains target sequences of BAP including normal flanking regions (not to scale). The APP-REP protein is marked with a 276 amino acid deletion (corresponding to APP-751 beginning at XhoI through to and including the glycine codon at 15 amino acid residues N-terminal terminal to BAP) and the insertion of sequences encoding N- and C-terminal reporter epitopes. Substrate P (SP) reporter epitope (RPKPQQFFGLM), which corresponds to Sequence I.D. No. 1, is inserted at the XhoI site. Met-enkephalin (ME) reporter epitope (YGGFM), which corresponds to Sequence I.D. No. 2, is inserted at the C-terminus of APP. The resulting construct, pCLL 602, encodes 492 amino acids (see FIG. 2).
Figure 2:
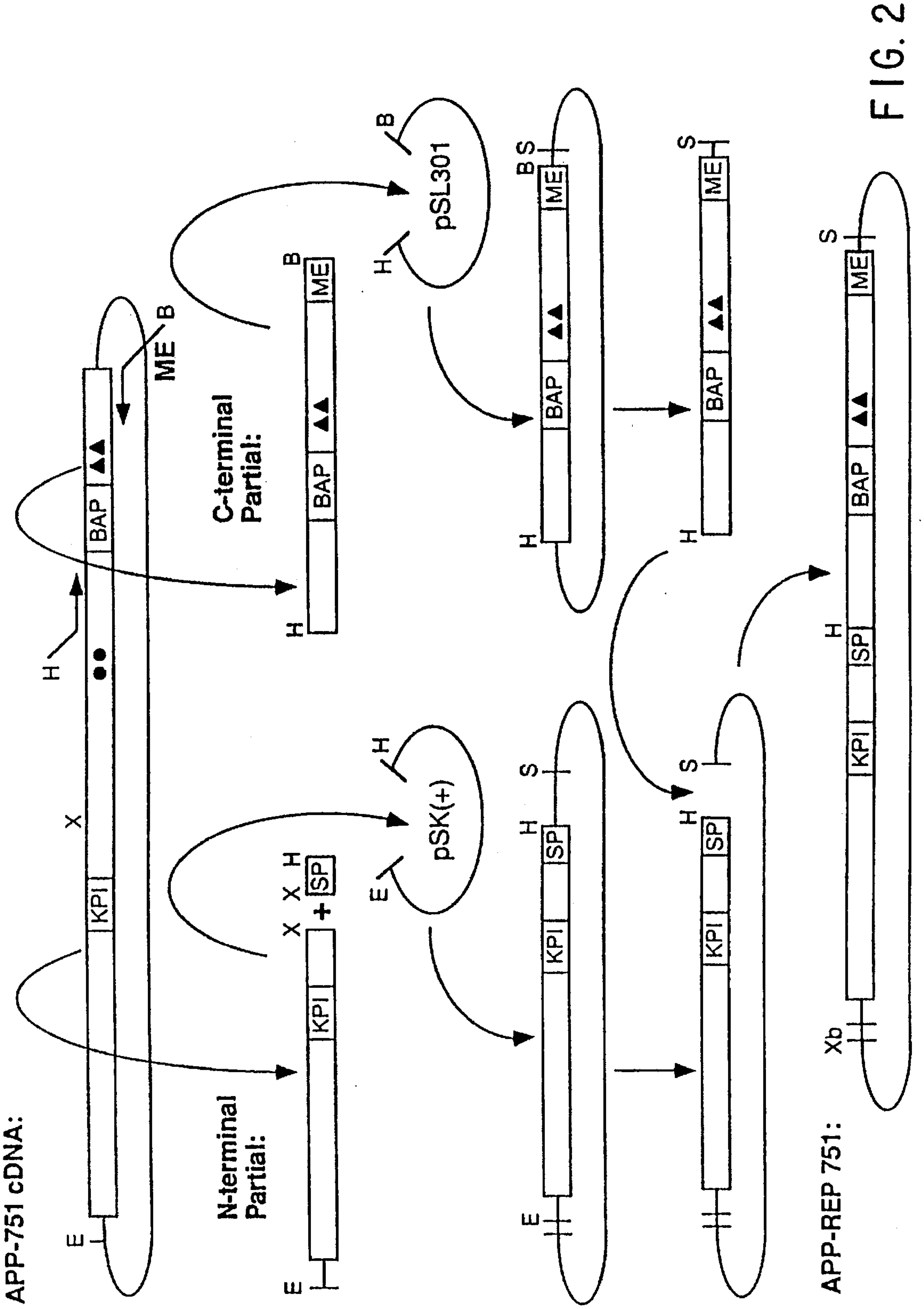
FIG. 2 shows a schematic representation depicting the construction of APP-REP from APP-751 cDNA. Partial representing N- and C-terminal regions of APP-REP are cloned separately as illustrated below. The N-terminal partial is constructed by ligating sequences encoding substance P (SP) to an N-terminal fragment of APP cDNA. The C-terminal partial is constructed by PCR amplification using the corresponding portion of APP cDNA to introduce novel ends including the Met-enkephalin (ME) reporter epitope. A functional APP-REP 751 clone is obtained by subcloning the partials as indicated. EcoRI (E), XhoI (X), HindIII (H), BamHI (B), SalI (S), XbaI (Xb).

A cassette approach is used to independently construct portions of the APP-REP plasmid (FIG. 2). The N-terminal partial includes APP sequences through the Substance P (SP) epitope, while the carboxy-terminal (C-terminal) partial includes BAP (or sequence variations of BAP) through the Met-enkephalin (ME) epitope (FIG. 1). Plasmid encoding the N-terminal cassette (pCLL935) is constructed by ligating the EcoRI-XhoI fragment derived from APP-751 cDNA to a short synthetic XhoI-HindIII fragment encoding Substance P (amino acids 1–11). This product is then ligated into the EcoRI and HindIII sites of pSK(+). Plasmid encoding the carboxy-terminal (C-terminal) cassette (pCLL947) is constructed by cloning into the HindIII-BamHI sites of pSL301 a fragment containing BAP sequences which is amplified by polymerase chain reaction. The fragment features a novel 5'-HindIII site beginning at lysine 638 of APP-751, native BAP through APP C-terminal sequences, and a C-terminal fusion including the Met-enkephalin epitope followed by a stop translation codon and a BamHI site. The resulting pSL301 HindIII-SalI fragment (including the HindIII-BamHI coding region plus BamHI-SalI polylinker sequences) is then isolated and ligated to the N-terminal cassette by subcloning into the HindIII-SalI sites of the SK(+)-based, CMV promoter driven, eucaryotic expression vector pcDNA-1-neo (pCLL601), whose polylinker is modified to accommodate the APP-REP fragment (pCLL602). Polylinker modification involves the substitution of the HindIII-XbaI fragment with a synthetic one which restores HindIII, destroys XbaI and introduces novel BamHI-XabI-Xho-SalI sites.

Tissue Culture Lines

All cells are obtained from American Type Culture Collection. and maintained according to their recommendation. They include SV40-transformed African Green monkey kidney COS-1 cells (CRL 1650) for transient expression and Chinese hamster ovary CHO-1C6 (CRL 1973) for stable expression systems. Also included are human embryonic kidney cells (CRL 1573).

Transfection Procedure

Cells are seeded at a density of 2–3×$10^6$/100 mm dish and transfected using Lipofectin (Gibco-BRL, Grand Island, N.Y.) when ~75% confluent. Plasmid DNA (0.5–4 mg) is diluted in 450 mL of Opti-MEM (Gibco-BRL, Grand Island, N.Y.) and mixed with 450 mL containing 75–100 mL Lipofectin. The mixture is incubated at room temperature for 20–30 minutes. Addition of DNA-Lipofectin mixture to cells, recovery phase and G418 selection (Gibco-BRL), when applicable, are according to the manufacturer's protocol. Cells and conditioned medium are harvested at 48–72 hours following transfection for assay of APP-REP expression.

Antisera

APP-specific antisera: anti-N-terminal APP, mouse monoclonal 22C11 (Boehringer-Mannheim Biochemicals, Indianapolis, Ind.) raised against a recombinant fusion protein expressing APP-695 (epitope mapped to aa 60–100); anti-KPI rabbit polyclonal, raised against recombinant protein encoded by the HinfI fragment derived from APP-770; and anti-APP C-terminal rabbit polyclonal M3, raised against synthetic APP peptides corresponding to APP-770 amino acid residues 649–671 (kindly provided by Dr. David Miller, New York State Institute for Basic Research in Developmental Disabilities, Staten Island, N.Y.) BAP-specific antisera: anti-mouse $IgG_1$-agarose (Sigma) for the precipitation of monoclonal 6E10 antibody, raised against synthetic $BAP_{1-24}$ (obtained from Drs. K. S. Kim and H. M. Wisniewski, New York State Institute for Basic Research in Developmental Disabilities, Staten Island, N.Y.). Reporter-specific antisera: anti-substance P, rabbit polyclonal, available from Peninsula, Belmont, Calif.; and anti-Met-enkephalin, rabbit polyclonal, available from Cambridge, Wilmington, Del.

Preparation of Radiolabeled APP-REP and Extraction from Conditioned Medium and Cell Lysates APP-REP proteins transiently expressed in exponentially growing adherent cells (~4×$10^6$) are radiolabeled by metabolic incorporation of [$^{35}$S]-methionine as follows. Cell monolayers are washed twice with prelabeling medium (methionine-free D-MEM supplemented with glutamine, sodium pyruvate, antibiotics and 1% dialyzed fetal bovine serum (Gibco-BRL)) and incubated for 15 minutes to 4 hours in prelabeling medium containing 150–450 uCi [$^{35}$S]-methionine (Amersham, 800 Ci/mmol). If chased with cold methionine, the medium is removed following the pulse, the monolayer is washed with prelabeling medium and replaced with 3 mL of the same containing 1 mM cold methionine.

The conditioned medium is recovered following radiolabeling by aspiration from plates and cell debris is removed by centrifugation for 10 minutes at 4° C. (~300×g). The conditioned medium is immediately supplemented with protease inhibitors (pepstatin A, 50 μg/mL; leupeptin, 50 μg/mL; aprotinin, 10 μg/mL; EDTA, 5 mM; PMSF, 0.25 mM) and either stored frozen at −20° C. or treated with immunoprecipitation buffer (IPB) for protein analysis (Sisodia et al., 1990). Briefly, 3 mL of CM is supplemented with 0.75 mL 5× IPB (250 mM Tris, pH 6.8; 750 mM NaCl;

25 mM EDTA; 2.5% Nonidet P40; 2.5% sodium deoxycholate; above-described protease inhibitors) and incubated for 20 minutes at 4° C. prior to use.

Lysates are prepared by washing the labeled cell monolayer twice with 5 mL pre-labeling medium and directly extracting cells in plates at 4° C. with 3.75 mL 1× IPB (including protease inhibitors). Cells are scraped into the buffer, incubated for 20 minutes at 4° C. and lysates clarified of cellular debris by centrifugation for 20 minutes at 10,000×g.

For radioiodination of cell surface proteins, monolayers are chilled on ice, washed 3 times with 5 mL ice cold PBS and then labeled at room temperature for 10 minutes following the addition of: 5 mL PBS containing 0.2 mCi $Iodine^{125}$ (NEZ-033A, New England Nuclear), 0.25 mL lactoperoxidase (1 mg/mL distilled water, Sigma), 10 mL of hydrogen peroxide solution (freshly prepared by diluting 10 mL of 30% stock in 10 mL of PBS) added at 0, 3, 6 and 9 minutes of iodination. At 10 minutes, the supernatant is removed and cells gently washed with 10 mL of ice cold PBS (containing 10 mM NaI). Four mL of PBS is added, and CM and cell lysates are prepared as above.

Immunoprecipitation Analysis

Aliquots of radiolabeled lysate or conditioned medium representing 4–8×$10^5$ cells are thawed on ice, supplemented with protease inhibitors (see above), boiled for 3 minutes in 0.35% SDS and chilled on ice. Samples are preincubated on a shaker for 1.5 hours at 4° C. with 2–10 mL 2× of preimmune (or normal rabbit) serum and 2 mg Protein A-Sepharose (Sigma; prepared in 1× IPB), and insoluble immune complexes removed by centrifugation. APP- or reporter epitope-specific antisera (0.1–10 μl) and 2 mg Protein A-Sepharose are similarly added and incubated overnight. Specific immune complexes are precipitated, washed 4 times with 0.25 mL 1× IPB (with protease inhibitors), extracted with 20 μl 2× SLP (Laemmli sample buffer; Laemmli, Nature 227:680–685, 1970), boiled for 3 minutes and fractionated by electrophoresis on SDS-polyacrylamide-tris-glycine (Bio-Rad Laboratories, Richmond, Va.) or SDS-polyacrylamide-tris-tricine Daiichi (Integrated Separation Systems, Natick, Mass.) gels. Gels are then treated with Enlightning Autoradiographic Enhancer (New England Nuclear, NEF-974) and dried in vacuo with heat and exposed to Kodak X-AR film overnight at −70° C.

Western (Immunoblot) Analysis

Lysate or 10× concentrated conditioned medium (Centricon 30 microconcentrator; Amicon, Beverly, Mass.) representing 4–8×$10^5$ cells are supplemented with an equal volume of 2× Laemmli sample buffer, boiled for 2 minutes, fractionated as above and transblotted (Semi-Phor, Hoefer Scientific Instruments, San Francisco, Calif.) to Immobilon-P membrane (Millipore, Bedford, Mass.). Membranes are pre-blocked in 10 mL 5% non-fat dry milk/PBST (PBS with 0.02% Tween 20) for 45 minutes at room temperature prior to overnight incubation at 4° C. with primary antisera (in fresh pre-blocking solution). Blots are then washed, incubated with secondary antibody, washed and developed for horseradish peroxidase activity by conventional methods (ECL Luminol Kit; Amersham, Arlington Heights, Ill.).

Peptide Mapping and Determination of the Site of Proteolytic Cleavage by Peptide Sequencing The secretase clip site is determined essentially as described by Wang et al., J. Biol. Chem. 266:16960–16964, 1991. Approximately 1×$10^6$ CHO cells stably expressing APP-REP are seeded in each 150 mm dish containing DMEM (complete with 200 μg/mL G418) and incubated for 36 hours. Cells are washed, preincubated for 6 hours in serum-free medium (MCDB 302) supplemented with antibiotics, L-glutamine (292 mg/L) and proline (12 mg/L) (Sigma) to remove serum components, washed, and incubated for another 72 hours in fresh serum-free media.

Serum-free conditioned medium is pooled and cell debris is removed by centrifugation (10 minutes at 300×g, then 30 minutes at 100,000×g) and concentrated by acetone precipitation and fractionated by HPLC. CM concentrate is loaded onto an anion exchange column (Mono Q) and protein is eluted in 20 mM Tris (pH 7.4) over a 0 to 1M NaCl gradient. Fractions containing secreted APP are identified by immunoblotting (monoclonal antibody 22C11) and relevant samples pooled, desalted (NP-5 column; Pharmacia, Piscataway, N.J.) and concentrated. Proteins are then denatured and treated with cyanogen bromide (in 10% trifluoroacetic acid). Peptides are separated by high performance liquid chromatography (Vydac $C_{18}$ reverse-phase) attached to a FAB-MS unit. Relevant peaks derived from APP-REP 751 and APP-REP $BAP_{\Delta 11-28}$ are identified by locating those peaks uncommon to both proteins. The C-terminal peptides derived from APP-REP $BAP_{\Delta 11-28}$ (predicted 14 aa) and APP-REP 751 (predicted 17 aa) are then sequenced (MilliGen solid phase peptide sequencer; Millipore, Burlington, Mass.).

Characterization of APP-REP Expression by Epitope Mapping

Figure 3:
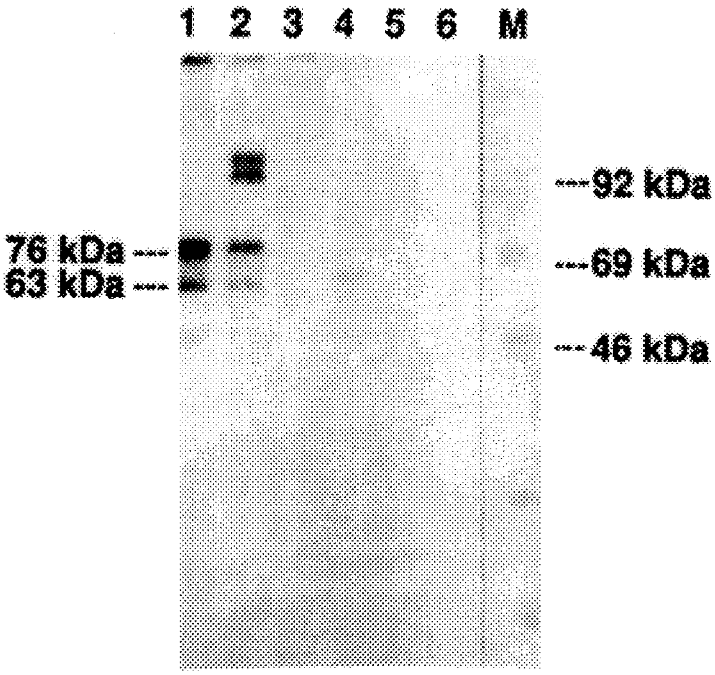
FIG. 3 shows an epitope mapping of APP-REP 751 expressed in COS-1 cells. Immunoprecipitation analysis of cell lysate and conditioned medium using the SP (anti-N-terminal substance P reporter) and M3 (anti-C-terminal APP) antisera. Lanes 1 and 2, cell lysate immunoprecipitated with SP and M3 antisera, respectively; lanes 3 and 4, conditioned medium immunoprecipitated with M3 and SP antisera, respectively; lanes 5 and 6, conditioned medium of control cells transfected with vector DNA immunoprecipitated with SP and M3 antisera, respectively; lane M, molecular weight markers.

The APP-REP strategy (FIG. 1) is a model system for the expression of marked APP proteins in tissue culture cells which is useful in characterizing proteolytic cleavage events. APP-REP protein transiently expressed in COS-1 cells is radiolabeled by metabolic incorporation of [$^{35}$S]-methionine in a 60 minute pulse, immunoprecipitated with antisera and size fractionated by gel electrophoresis, as demonstrated in FIG. 3. Immunoprecipitation with a panel of APP- and APP-REP-specific antisera which recognize epitopes mapping at various positions along APP-REP, reveals the presence of 2 proteins of ~63 and ~76 kDa in cell lysates (including cytoplasmic and membrane associated proteins) as shown in FIG. 3. The specific detection by antisera directed against the KPI domain, the carboxy-terminus of APP (M3, FIG. 3A) and Met-enkephalin as well as by the N-terminal 22C11 monoclonal in Western blot analysis suggest that both bands represent the full-length APP-REP protein. Although the 492 amino acid APP-REP is predicted to display a mobility of 54 kDa, the larger 63 and 76 kDa proteins are observed, attributing the aberrant migration properties of APP, putatively to post-translational modification like tyrosine-sulfation, glycosylation and phosphorylation (Dyrks et al., EMBO J. 7:949–957, 1988; Weidemann et al., Cell 57:115–21.26, 1989).

Analysis of the conditioned medium (CM) collected from those same cells above indicates that an N-terminal fragment of APP-REP is released into the CM. FIG. 3B reveals a shorter ~67 kDa fragment immunoprecipitable from CM with KPI and [SP antisera (and the 22C11 monoclonal by Western analysis), but not with several C-terminal APP or ME antisera. These data are consistent with the observations (Selkoe et al., PNAS U.S.A. 86:6338–6342, 1988; Palmert et al., PNAS U.S.A. 85:7341–7345, 1989) indicating that APP is a substrate for the proteolytic cleavage resulting in the secretion of an N-terminal fragment into CM and a short membrane associated C-terminal fragment.

Figure 4A:
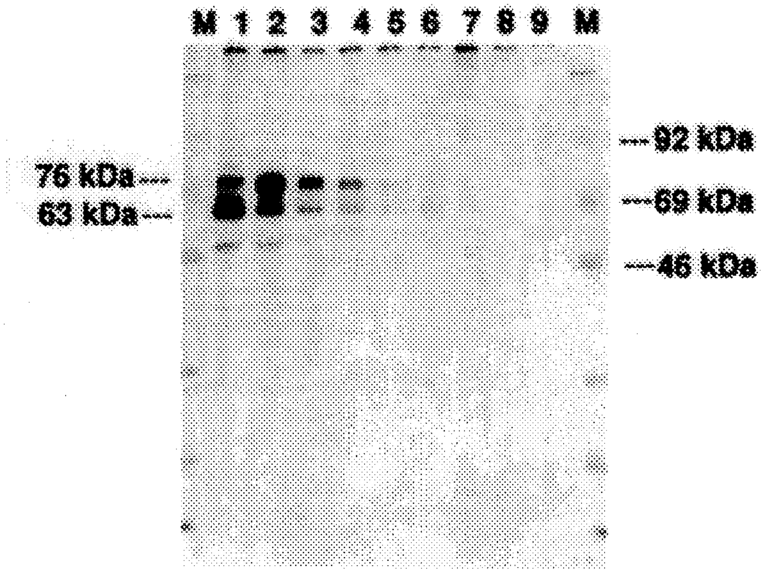
FIG. 4 shows pulse-chase analysis of APP-REP 751. Immunoprecipitation of cell lysate (A) and CM (B). COS-1 cells are pulsed with [$^{35}$S]-methionine for 15 minutes and chased using cold methionine for 0, 0.5, 1, 1.5, 2 and 4 hours (lanes 1 to 6). Lanes 7, 8 and 9 are chase intervals of 0, 1 and 2 hours for control cells transfected with vector DNA. Lane M, molecular weight markers.

Pulse-Chase Analysis Reveals the Precursor/Product Relationship between Cell Associated and Secreted Derivatives of APP-REP To show that APP-REP undergoes post-translational modification accounting for the 2 cell associated proteins, and that the N-terminal APP-REP fragment released into CM is derived from one of these precursors, APP-REP is radiolabeled with a short 15 minute pulse and both cell lysates and CM are collected at various chase intervals as shown in FIG. 4. Immunoprecipitation analysis reveals that APP-REP initially migrates at ~63 kDa and is rapidly "chased" up to ~75 kDa with conversion rate of less than 10–15 minutes (FIG. 4A; also see FIG. 5C for quantitative analysis), an observation which is consistent with the notion that APP-REP, like APP, is a substrate for post-translational modifications.

Figure 4B:
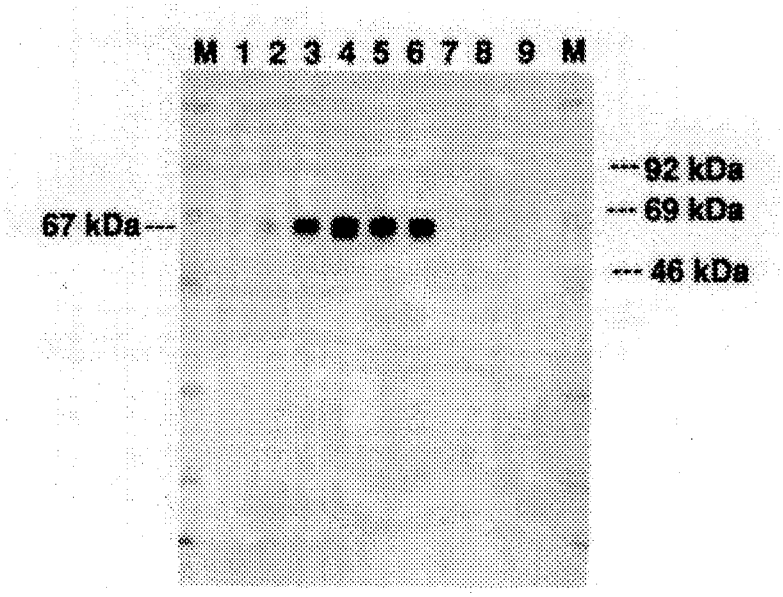
Figure 5A:
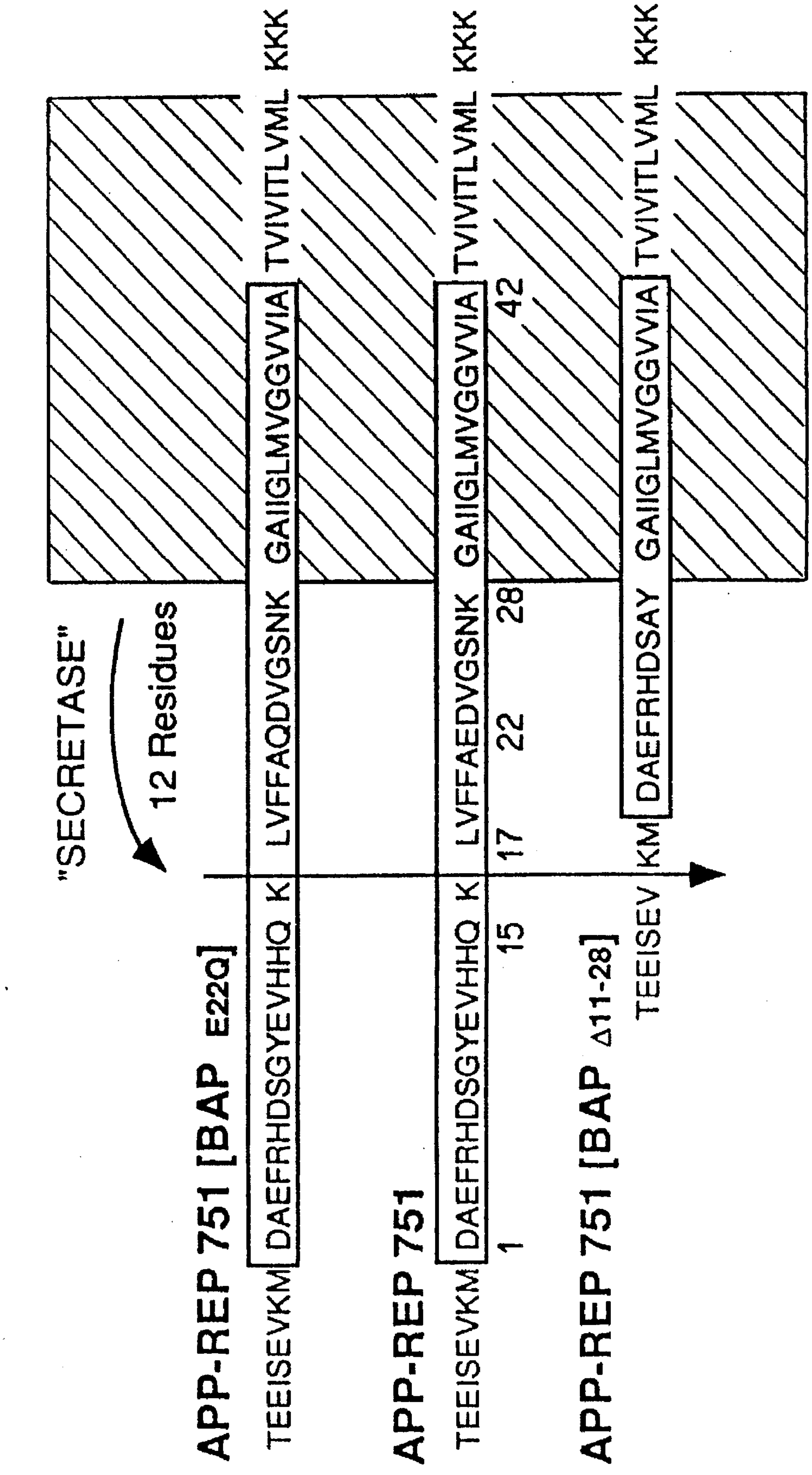
FIG. 5 shows epitope mapping and comparative expression of $BAP_{E22Q}$, APP-REP 751 and $BAP_{\Delta 11-28}$, which correspond to Sequence I.D. Nos. 2, respectively. A is a schematic representation of relevant BAP (boxed) and flanking amino acid sequences of $BAP_{E22Q}$, APP-REP 751 and $BAP_{\Delta 11-28}$ juxtapositioned against the putative transmembrane domain (shadowed). B–E are the immunoprecipitation analysis with antibodies recognizing indicated substance P (SP), KPI domain (KPI), C-terminal APP (M3) or Met-enkephalin (ME) epitopes; Lane M, molecular weight marker. B shows conditioned medium obtained from COS-1 cells expressing APP-REP 751 (lane 3), $BAP_{E22Q}$ (lanes 4, 6 and 8), $BAP_{\Delta 11-28}$ (lanes 5, 7 and 9) or control cells with (lane 2) or without (lane 1) transfection with vector DNA. C shows cell lysates obtained from COS-1 cells expressing APP-REP $BAP_{E22Q}$ (lanes 1, 4 and 7), $BAP_{\Delta 11-28}$ (lanes 2, 5 and 8) and control cells transfected with vector DNA (lanes 3, 6 and 9). D shows the accumulation of secreted APP-REP 751 fragments in the conditioned medium obtained from COS-1 cells expressing APP-REP 751 (lanes 2 and 6), $BAP_{E22Q}$ (lanes 3 and 8), $BAP_{\Delta 11-28}$ (lanes 4 and 7) or control cells transfected with vector DNA (lanes 1 and 5), which are pulsed with [$^{35}$S]-methionine and chased for 45 (lanes 1–4) or 90 (lanes 5–8) minutes with cold methionine. E shows the accumulation of secreted APP-REP fragments in the conditioned medium obtained from stable (Chinese hamster ovary cells; lanes 1–4) and transient (COS-1 cells; lanes 5 and 6) expression of APP-REP 751 (lanes 2 and 5), $BAP_{\Delta 11-28}$ (lanes 3 and 6), $BAP_{E22Q}$ (lane 4) or control cells transfected with vector DNA (lane 1).
Figure 5B:
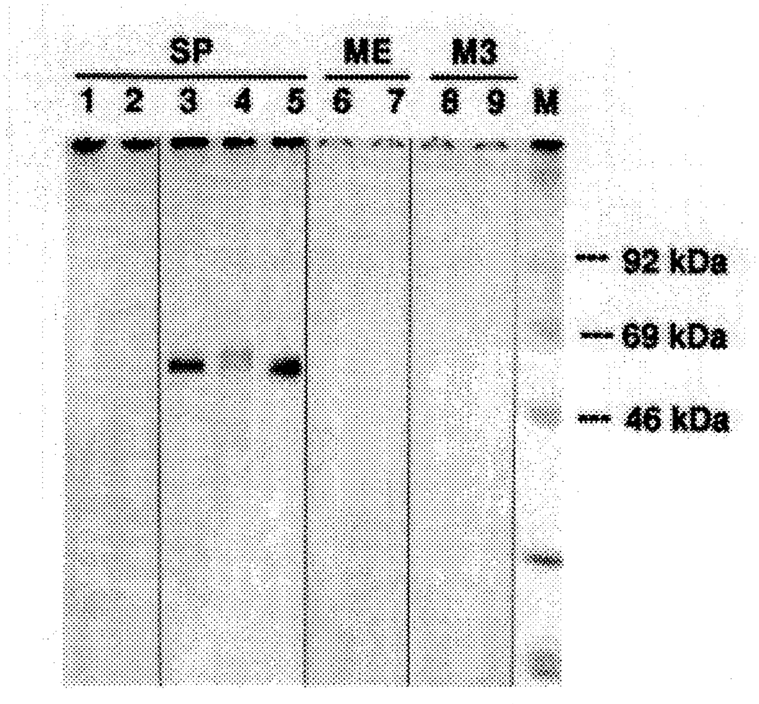
Figure 5C:
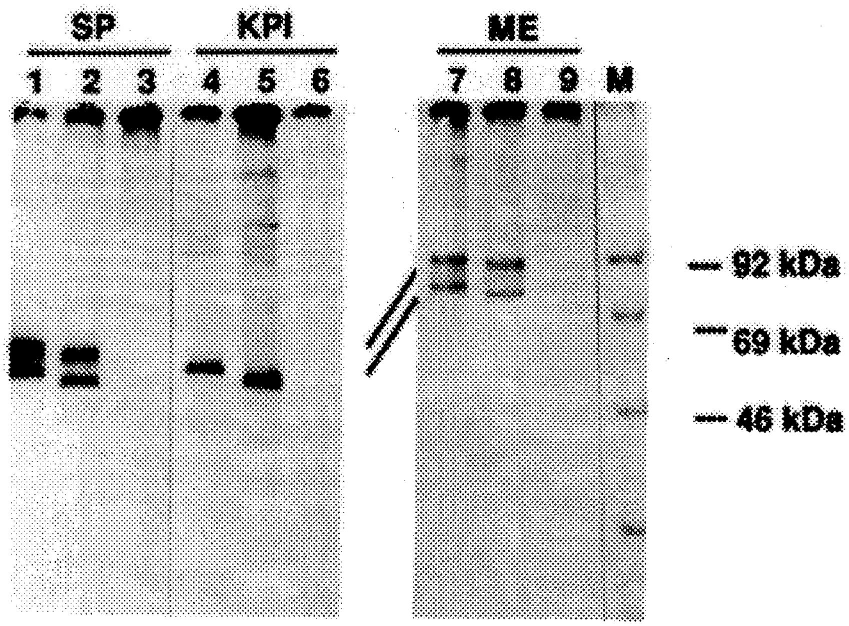
Figure 5D:
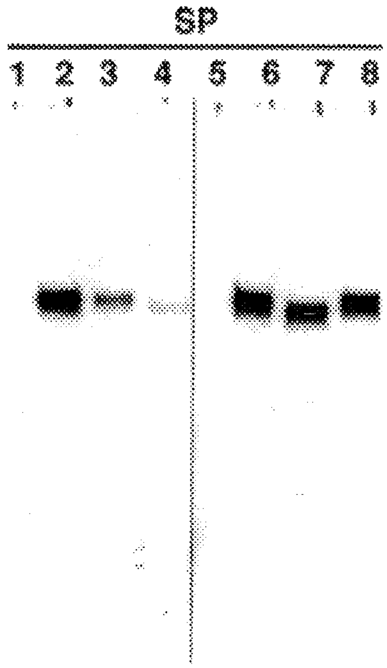

The ~76 kDa APP-REP band (cell lysate) rapidly disappears ($t_{1/2}$ ~20 minutes) (FIGS. 4A and 5C), followed by the appearance of a shorter ~67 kDa band in the CM (FIGS. 4B and 5C). The released ~67 kDa fragment accumulates rapidly and is relatively long lived ($t_{1/2}$>8 hours). The temporal pattern of intracellular APP-REP depletion, accumulation of a shorter ~67 kDa protein in CM, and the recognition of this protein only by antisera raised against N-terminal epitopes, is consistent with proteolytic cleavage of APP-REP which is similar to the normal, non-amyloidogenic, "secretase" activity which results in the release of an N-terminal APP fragment (Sisodia et al., Science 248:492–495, 1990).

Figure 5E:
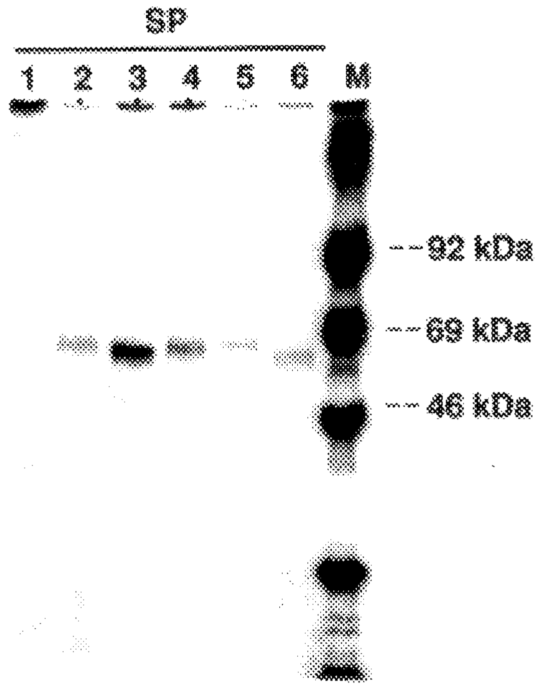

Expression of APP-REP Derivatives Containing Altered BAP Sequences Does Not Prevent Proteolytic Cleavage In an attempt to engineer non-cleavable substrates for secretase, APP-REP proteins (FIG. 5A) are expressed either lacking the secretase "cleavage/recognition site" putatively encompassed by aa residues BAP 11-28 ($BAP_{\Delta 11\text{-}28}$, pCLL604), or representing the BAP point mutation found in patients with HCHWA-D ($BAP_{E22Q}$, pCLL603). The construct representing the $BAP_{E22Q}$ mutation results in secretion of an N-terminal fragment indistinguishable from the APP-REP protein (FIG. 5C). Deletion of extracellular, juxtamembranous 18 aa ($BAP_{\Delta 11\text{-}28}$) still results, however, in the secretion of an N-terminal APP-REP fragment into the CM (FIG. 5B). A slightly faster migration of fragment derived from the deletion construct pCLL604 in comparison to that of wild-type pCLL602, is consistent with the 18 aa deletion and a corresponding loss of ~2 kDa (FIG. 5C). Pulse-chase analyses (FIG. 5D) indicate that expression of full-length precursor by each construct, proteolytic cleavage and the release of fragment into CM are both qualitatively and quantitatively similar to that of the wild-type APP-REP sequence. Chinese hamster ovary (CHO) cells stably expressing APP-REP display results similar to that of transiently expressing COS-1 cells (FIG. 5E). Collectively, these data suggest that the cleavage in each case may be the result of similar biochemical events despite the difference in juxtamembranous sequences (FIG. 5A).

Full-Length APP-REP Proteins Are Associated with Plasma Membrane Prior to Cleavage In preliminary experiments, detection of the amino-terminal APP-REP fragment in CM and not in cell lysates, suggests that the putative secretase activity may be plasma membrane-associated. One prediction of this notion is that an N-terminal portion of APP-REP may be (partially) localized to the extracellular environment prior to cleavage. In order to test this hypothesis, CHO cells stably expressing APP-REP (pCLL602) are subjected to lactoperoxidase-catalyzed iodination to radiolabel only extracellular proteins associated with the cell surface. CM and cell lysates are analyzed immediately following iodination or after a 10 minute incubation. Presence of the ~76 kDa APP-REP band in cell lysate indicates that at least a portion of full-length APP-REP is poised extracellularly in association with cell membrane. Detection of both, a reduced fraction of the ~76 kDa band in the cell lysate and a corresponding increased fraction of ~67 kDa fragment in CM following the "release" incubation suggest that the extracellular portion of APP-REP is cleaved.

Peptide Mapping to Determine the Site of Proteolysis

Figure 6A:
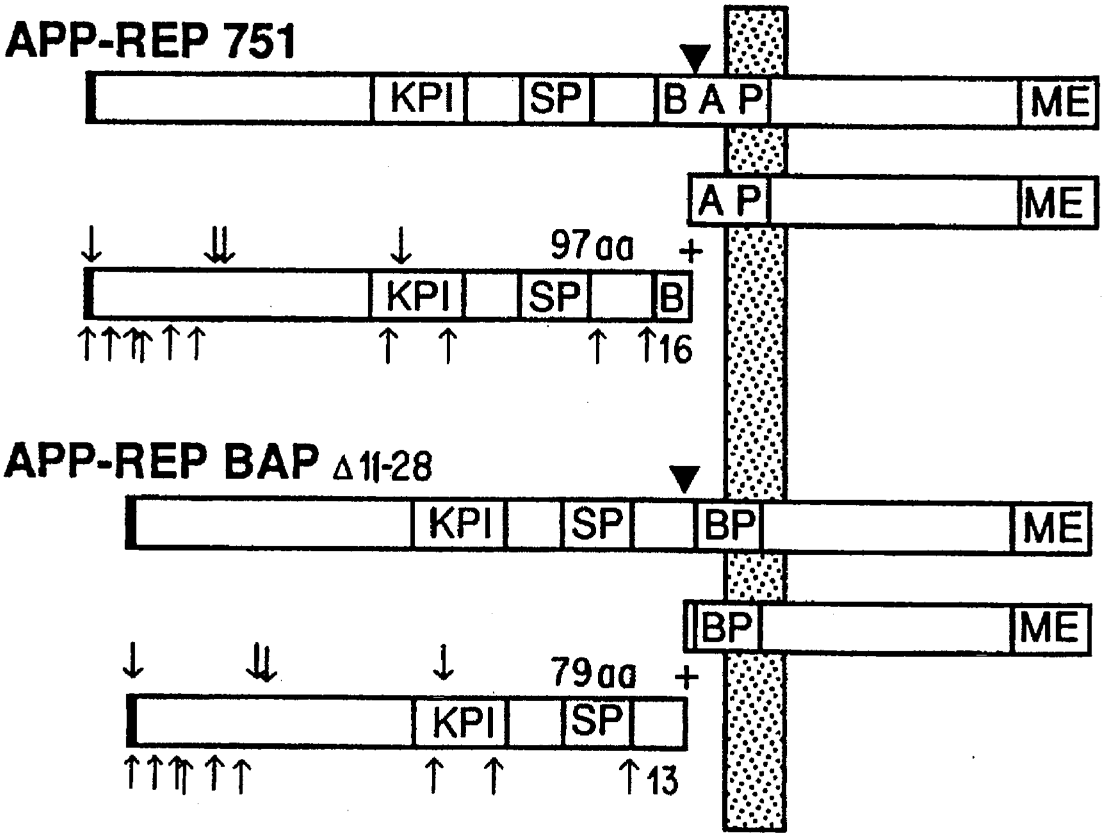
FIG. 6 shows peptide mapping of fragments secreted into the conditioned medium obtained from Chinese hamster ovary cells stably expressing APP-REP 751, $BAP_{E22Q}$ and $BAP_{11-28}$. A is the schematic representation depicting the APP-REP 751 and related derivative indicating the cleavage products and relevant carboxy-terminal fragments derived from treating the secreted fragments either with BNPS-Skatole (B) or cyanogen bromide. Downward- or upward-facing arrows represent BNPS-Skatole and cyanogen bromide cleavage sites, respectively. Amino acid lengths of relevant fragments for mapping or sequencing are given. B is the BNPS-Skatole treatment of fragments secreted into the conditioned medium obtained from CHO cells stably expressing APP-REP 751 or $BAP_{\Delta 11-28}$. Mixture of conditioned medium containing APP-REP and $BAP_{\Delta 11-28}$ (lane 1), or $BAP_{\Delta 11-28}$ (lane 2) and APP-REP 751 (lane 3) alone.
Figure 6B:
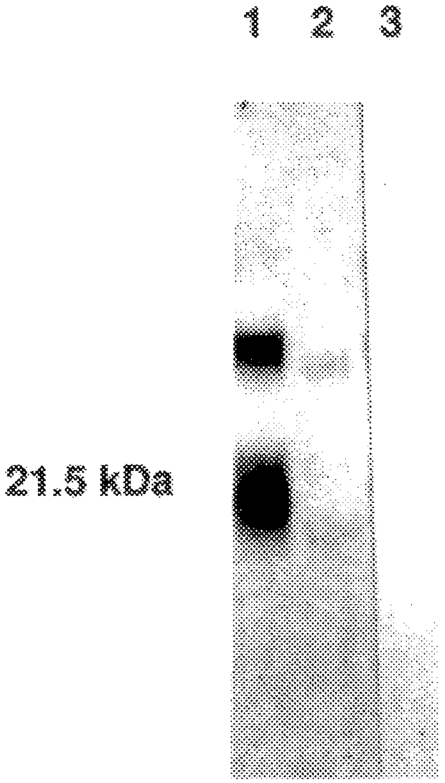

Fragment secreted into serum-free media derived from CHO cells stably expressing APP-REP with wild-type or $BAP_{\Delta 11\text{-}28}$ sequences is analyzed to determine the actual site of proteolytic cleavage as shown in FIG. 6. Peptide mapping by tryptophan-specific cleavage with BNPS-skatole is used initially to roughly determine the approximate position of cleavage in each molecule. Western blot analysis using SP antisera following BNPS-skatole treatment (FIG. 6B) reveals fragments whose lengths of ~10.5 and ~9.5 kDa, corresponding to wild type and $BAP_{\Delta 11\text{-}28}$, respectively, confirming that cleavage occurs in the C-terminal portion of the PN-II-like protein (FIG. 6A). To determine the actual position of cleavage, the secreted fragment is partially purified and treated with cyanogen bromide, and the relevant C-terminal peptides derived from APP-REP wild type and $BAP_{\Delta 11\text{-}28}$ are sequenced.

DISCUSSION

The expression of a truncated form of APP-751, namely APP-REP 751 (pCLL602) and its normal cleavage by secretase are described herein. A comparison of thr nontransfected cells and those transfected with APP-REP 751, in both COS-1 transient and CHO stable expression systems, show the production of the shorter secreted protein derived from APP-REP. Furthermore, upon a prolonged exposure of the fluorogram only one band is observed in CM. Epitope mapping with antibodies to N- and C-terminal domains of APP-REP and amino acid sequencing suggest post-translational cleavage at a site similar to that reported for intact APP protein and other truncated APP constructs. Pulse-chase experiments reveal post-translational modifications, believed to be similar to those described for the intact APP protein in which a single ~63 kDa product is chased up to ~76 kDa in the first 30 minutes. Appearance of the ~76 kDa cell membrane associated protein precedes the release of a ~67 kDa product into the CM. The released form, which is not observed in the cell lysate fraction, steadily accumulates in the CM well after the ~76 kDa band has begun to disappear suggesting a precursor-product relationship. These data indicate that the APP-REP protein is a good representation of the naturally occurring APP with regard to post-translational synthesis, processing, and stability in a tissue culture system.

Epitope mapping of APP-REP 751 mutants suggest that $BAP_{E22Q}$ as well as the $BAP_{\Delta 11\text{-}28}$ deletion constructs, are initially expressed as larger proteins of predicted lengths which subsequently are cleaved to release N-terminal fragments into the CM. The pulse-chase experiments indicate the cell-associated and secreted forms accumulate with similar kinetics.

APP is cleaved normally within the BAP sequence to release the non-amyloidogenic, amino-terminal PN-II fragment. Treatment of cells with an agent which activates protein kinase C ($PK_c$) (phorbol dibutyrate) is shown to increase the release of the amino-terminal fragment. A panel of mutant APP reporter constructs is herein expressed in which each of the potential phosphorylation sites located within the cytoplasmic domain of APP are replaced with alanine residues. Phorbol response patterns are unchanged suggesting that induced cleavage occurs independently of APP substrate phosphorylation. It is presently determined that phorbol (a) increases the release of PN-II fragment that is consistent with the normal secretase activity, (b) decreases the release of a shorter amino-terminal APP fragment cleaved near the amino-terminus of BAP, and (c) decreases the release of BAP. This is believed to be the first demonstration that any pharmacological treatment reduces the formation of BAP and indicates that $PK_c$ activators may be developed as therapeutic agents to block BAP formation.

The major proteolytic cleavage of APP occurs within the juxtamembranous ectodomain by secretase leading to the release (or secretion) of the N-terminal APP fragment (PN-II). This cleavage takes place within the BAP sequence and precludes the proteolytic generation of BAP from APP.

The APP holoprotein is phosphorylated and the phosphorylation may be involved in regulation of APP processing and the generation of BAP and amyloidogenic fragments.

Phosphorylation of APP-related peptides in vitro and analysis of APP following the activation of $PK_c$ in permeabilized cells show that cytoplasmic APP residues threonine-710 and serine 711 are substrates for phosphorylation (FIG. 9B). Treatment of cells with phorbol dibutyrate (PDBu), an agent which activates $PK_c$, increases the release of N-terminal APP fragment(s), increases the generation of C-terminal APP fragments and decreases the amount of mature, full-length APP forms.

Figure 9A:
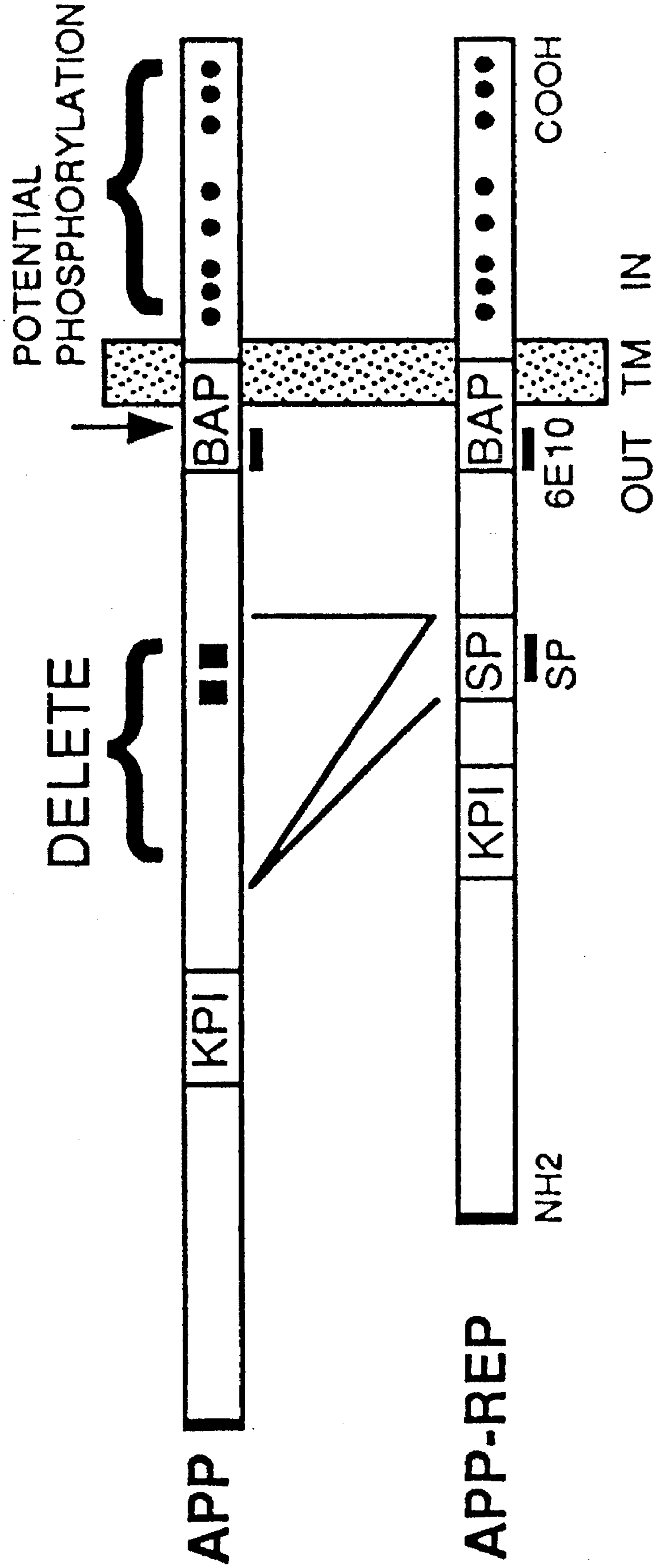
FIG. 9A is a schematic representation of APP-REP which is derived from APP-751 cDNA and contains intact sequences encoding BAP, the transmembrane spanning region and cytoplasmic C-terminus of APP (not to scale).
Figure 10A:
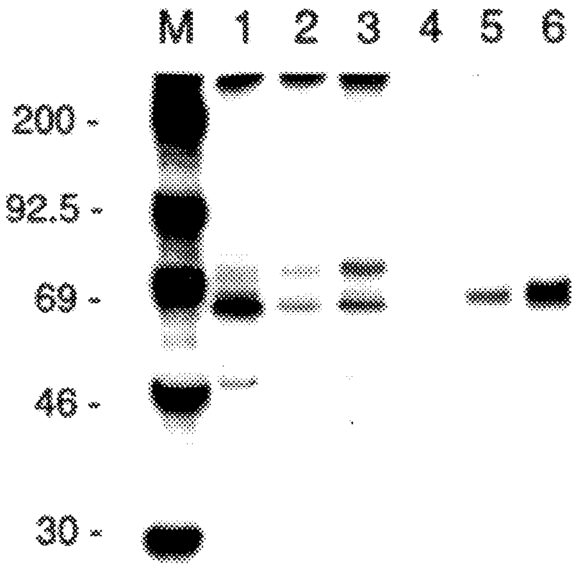
Figure 10B:
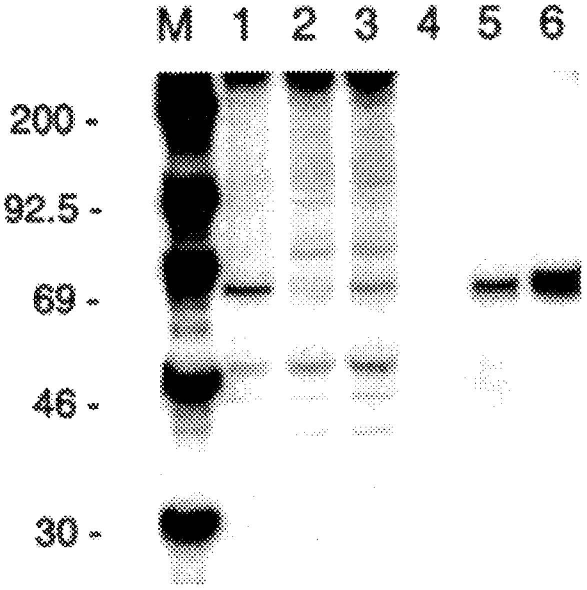

To more fully characterize the phorbol (PDBu) response of increased APP proteolysis, the APP reporter (APP-REP 751) system as a useful tissue culture model for the expression and cleavage of APP molecules is employed (FIG. 9A). Human HTB14 (FIG. 10A) and 293 (FIG. 10B) cells stably expressing APP-REP are treated with PDBu and tested for the release of N-terminal APP fragments into conditioned medium (CM) by immunoprecipitation analysis. In both transfected cell lines, a 3–4 fold increase in the amount of APP-REP-derived ~67 kDa PN-II fragment in the CM of PDBu-treated cells is observed (FIGS. 10A and 10B, compare lanes 5 to lanes 6). Analysis of corresponding cell-associated APP-REP in lysates indicates that PDBu treatment decreases the amount of full length APP-REP forms (FIGS. 10A and IOB, compare lanes 3 to lanes 2). A similar robust PDBu response is observed with the transient expression of APP-REP in COS-1 cells. In summary, PDBu increases the fraction of full-length substrate APP-REP molecules which are rapidly cleaved to release N-terminal fragment(s) into CM.

Control CM obtained from the transient expression of APP-REP is analyzed in COS-1 cells by immunoprecipitation with antibody to Substance P (SP; FIG. 9A) reporter in order to characterize the type of N-terminal APP fragments (s) released by treatment with PDBu. Ordinarily only ~67 kDa band is visualized (FIG. 11A, lanes 2 and 3), but closer examination reveals the presence of a doublet band migrating at ~65–67 kDa (FIG. 11A, lanes 4 and 5).

The APP-REP fragments released into the CM are then tested for the presence of the N-terminal portion of BAP (i.e., BAP aa residues 1–16; $BAP_{1-16}$) by differential immunoprecipitation with the monoclonal antibody 6E10 which specifically recognizes $BAP_{1-16}$ (FIG. 11B). Immunoprecipitation of CM from untreated control cells with 6E10 yields predominantly the upper component of the doublet (lane 4) as compared to precipitation with SP (lane 3). Immunodepletion of CM with 6E10 (lane 4) and subsequent immunoprecipitation with SP (lane 5) clearly reveals the lower, faster migrating ~65 kDa band. In contrast, when cells are treated with PDBu and the CM is then immunoprecipitated with SP (lane 6) or 6E10 (lane 7), nearly equal amounts are precipitated. Furthermore, if CM immunodepleted with 6E10 (lane 7) is subsequently immunoprecipitated with SP (lane 8), the faster migrating kDa band cannot be detected. This indicates the PDBu preferentially enhances the release of full-length PN-II.

To determine the effect of PDBu upon formation of BAP, a larger volume of CM from COS-1 cells transiently expressing APP-REP is analyzed for release of both PN-II fragment of BAP (FIG. 12). Immunoprecipitation of CM with 6E10 antibody reveals the presence of an ~4.2 kDa fragment (lanes 1 and 3) which is found only in the CM of transfected cells, whereas an ~3.5 kDa fragment is detected in CM of all cells (lanes 1–67). Failure to precipitate both the ~4.2 and ~3.5 kDa fragments following the addition of competing cold synthetic $BAP_{1-40}$ to CM indicates they both contain an epitope of BAP. Specificity of 6E10 antibody for BAP sequences and detection of an ~4.2 kDa fragment only in CM of cells overproducing APP-REP provides supporting evidence that the ~4.2 kDa peptide is BAP. Treatment of cells with PDBu greatly reduces the amount of ~4.2 kDa BAP fragment without influencing the ~3.5 kDa product (compare lanes 1 to 2 and 3 to 4). The presence of the $BAP_{1-16}$ epitope within the ~3.5 kDa fragment suggests that it represents a novel peptide which is not identical to a 3 kDa fragment derived from the C-terminal APP fragment which remains cell-associated following cleavage by secretase. These data demonstrate the COS-1 cells overproducing APP normally release BAP into CM and treatment with PDBu causes a reduction in release of immunoprecipitable BAP.

If phosphorylation of APP is the event which alters processing, mutations introduced at critical sites to prevent phosphorylation may block the observed PDBu response. To construct such mutants, each of the 8 aa that are potential phosphorylation substrates located within the cytoplasmic domain of APP-REP is changed to create a panel of independent 'phosphorylation-minus' derivatives (FIG. 9B) which are stably expressed in HTB14 cells. A 'double' mutant (T710A/S711A, pCLL616) is also constructed and expressed. With one exception (see below), each mutant releases basal levels of PN-II similar to that of wild type APP-REP and all typically display the 3–4 fold increase in release of PN-II in response to PDBu (FIG. 13). Quantitation of cell-associated full-length forms indicates that each mutant construct responds similarly to treatment by PDBu. An identical pattern of PDBu response with wild type APP-REP and the mutant derivatives expressed stably in 293 or transiently in COS-1 cells is observed. The inability of 'phosphorylation-minus' mutations to block PDBu responsiveness shows that APP substrate phosphorylation may not be a critical event in PDBu-stimulated release of PN-II.

Expression levels of cell-associated, full-length plasmid pCLL629 (Y743A, FIG. 9B) are similar to wild type APP-REP. However, the release of PN-II is about 3–4 fold more than untreated wild type APP-REP controls while addition of PDBu results in only a minimally enhanced release of PN-II (FIG. 13). Furthermore, this mutant displays increased formation of BAP by 3–4 fold (FIG. 12, compare lanes 1 and 3) which is decreased by PDBu treatment (FIG. 12, compare lanes 3 and 4). It is possible that elevated release of untreated Y743A mutant samples masks the PDBu response. Nevertheless, the data suggest that different mechanisms may account for the increase of PN-II release observed with PDBu treatment and the Y743 mutant since each of these manipulations has an opposite effect upon BAP release.

The substituted tyrosine of Y743A is located within a NPXY motif that may be a homolog to the cytoplasmic sequence on the LDL receptor which mediates internalization by coated pit formation and may be directly involved with a process which influences APP processing. It is likely that the APP cytoplasmic domain participates in multiple roles pertaining to APP trafficking and processing.

Cells expressing muscarinic acetylcholine receptors (m1 or m3 receptor subtypes) are observed as being capable of increasing the release of N-terminal APP fragment(s) in response to the cholinergic agonist carbachol (Buxbaum et al., Proc. Natl. Acad. Sci. U.S.A. 89:10075, 1992; Nitsch et al., Science 258:304, 1992). Increased release is blocked either by the muscarinic antagonist atropine or the $PK_c$ inhibitor staurosporine, but not by calcium ionophore A23187. Similarly, interleukin-1 (IL-1), a cytokine that may mediate APP expression via $PK_c$ (Goldgaber et al., Proc. Natl. Acad. Sci. U.S.A. 86:7606, 1989), activates a receptor-$PK_c$ coupled increase in APP release. These observations indicate that direct or indirect receptor-mediated $PK_c$ activation, or regulation of the targets of phosphorylation, in combination with the novel mutant APP-REP fragments in tissue culture systems described herein, may be uniquely employed for developing therapeutic interventions that prevent the formation of BAP.

In the tissue culture system of the present invention, both the release of PN-II (or an APP-REP equivalent) and BAP can be measured simultaneously. It is demonstrated that there is an inverse relationship between the release of both products following treatment with an activator of protein kinase C, namely, a phorbol ester. Since agonists of muscarinic receptors M1 and M3 lead to the activation of $PK_c$, such agonists are of potential therapeutic interest for down-regulating the production of BAP. That one of the APP-REP mutants (pCLL629, Y743A) reveals the simultaneous up regulation in release of both PN-II and BAP indicates the necessity to account for the production of both derivatives when screening for compounds which are aimed at modulating the processing of APP in a specific manner.

Advantageously, the decrease in release of BAP by PDBu demonstrates that BAP formation can be pharmacologically reduced and affords a drug discovery strategy for developing therapeutics using the tissue culture models of the present invention. The release of PN-II and BAP may be uniquely employed as markers for testing agents which regulate APP processing.

In accordance therewith, this invention provides a method for screening for compounds which reduce the formation of BAP which comprises measuring the amount of the marker (s) in the medium containing transfected cells stably or transiently expressing the mutants described herein, treating said cells with the sample compound, such as, for instance, a receptor mediated or direct activator of PKc (e.g., agonists of muscarinic receptors M1 and M3), and testing the medium for an increase in the amount of the marker(s). To rule out false positives, the medium containing agents which are able to increase the presence of the marker(s) are then further treated to assay for the reduction of BAP. For example, the treated cells can be contacted with an antibody directed to a portion of the BAP sequence under suitable conditions to favor the formation of an antibody-antigen complex, and the presence of any complex so formed can be detected by conventional techniques.

In the foregoing, there has been provided a detailed description of particular embodiments of the present invention for the purpose of illustration and not limitation. It is to be understood that all other modifications, ramifications and equivalents obvious to those having skill in the art based on this disclosure are intended to be included within the scope of the invention as claimed.

TABLE 1

Construction of APP—REP Partials

A. pSK(+) Amino-Terminal Constructs: Cloning of APP Isoform and Reporter Epitope (EcoRI-HindIII Fragments)

| Plasmid Name | APP Isoform (EcoRI-XhoI Fragment) | Reporter Epitope (XhoI-HindIII Fragment) |
|---|---|---|
| pCLL983 | APP 695 | Substance P* |
| pCLL935 | APP 751 | Substance P |
| pCLL934 | APP 770** | Substance P |
| pCLL913 | APP 770# | Substance P |

B. pSL301 Carboxy-Terminal Constructs: Cloning of BAP-Encoding APP Reporter Epitope Fusions (HindIII-BamHI/SalI Fragment)

| Plasmid Name | Met-Enkephalin (ME) Fusion at end of: | Name of Variation |
|---|---|---|
| pCLL947 | Full-Length APP | APP—BAP—APP—ME |
| pCLL914 | Transmembrane Domain | APP—BAP—TM—ME |
| pCLL937 | BAP | APP—BAP—ME |

TABLE 1-continued

Construction of APP—REP Partials

C. pSL301 Carboxy-Terminal Full-Length APP—ME Constructs: Introduction of Mutations in BAP (HindIII-BamHI/SalI Fragment)

| Plasmid Name | Met-Enkephalin Fusion at End of: | Name of Variation |
|---|---|---|
| pCLL949 | E to Q substitution at BAP aa #22 | $BAP_{E22Q}$ |
| pCLL957 | G to A substitiuon at BAP aa #10, deletion of BAP aa #11-28 and creation of novel NdeI site | $BAP_{\Delta 11-28}$ |

Notes:
*Substance P is a peptide containing 11 residues with the aa sequence of RPKPQQFFGLM.
**5' untranslated sequences derived from the shorter APP-770 cDNA form.
#5' untranslated sequences derived from the longer APP-751 cDNA form.

TABLE 2

Assembly of APP—REP Full-Length Constructs Containing Substance P and Met-Enkephalin Reporter Epitopes and BAP or a Variation of BAP

| Plasmid Name | Construct Name/Variation | Plasmid (N-Terminus) | Restriction Fragment (C-Terminus) |
|---|---|---|---|
| pCLL918 | APP—REP 695 | pCLL983 | pCLL947 |
| pCLL964 | APP—REP 751 | pCLL935 | pCLL947 |
| pCLL962 | APP—REP 770 | pCLL934 | pCLL947 |
| pCLL919 | APP—REP 695/$BAP_{E22Q}$ | pCLL983 | pCLL949 |
| pCLL989 | APP—REP 751/$BAP_{E22Q}$ | pCLL935 | pCLL949 |
| pCLL987 | APP—REP 770/$BAP_{E22Q}$ | pCLL934 | pCLL949 |
| pCLL920 | APP—REP 695/$BAP_{\Delta 11-28}$ | pCLL983 | pCLL957 |
| pCLL990 | APP—REP 751/$BAP_{\Delta 11-28}$ | pCLL935 | pCLL957 |
| pCLL988 | APP—REP 770/$BAP_{\Delta 11-28}$ | pCLL934 | pCLL957 |

TABLE 3

Subcloning of APP—REP Full-Length Constructs and Human Growth Hormone (hGH) into pcDNA-1-Neo[XS]

| Plasmid Name | Construct Name (in pcDNA-1-neo) | Source of Insert |
|---|---|---|
| pCLL600 | pcDNA-1-neo-hGH | p0GH* |
| pCLL601 | pcDNA-1-neo[XS] | Synthetic Fragment** |
| pCLL602 | APP—REP 751 | pCLL964 |
| pCLL603# | APP—REP 751/$BAP_{E22Q}$ | pCLL989 |
| pCLL604# | APP—REP 751/$BAP_{\Delta 11-28}$ | pCLL990 |
| pCLL605 | APP—REP 770 | pCLL962 |
| pCLL606 | APP—REP 770/$BAP_{E22Q}$ | pCLL987 |
| pCLL607 | APP—REP 770/$BAP_{\Delta 11-28}$ | pCLL988 |

Notes:
*The HindIII-EcoRI (blunt-ended) fragment encoding hGH sequences of p0HG (Nichols Diagnostics) is subcloned into the HindIII-EcoRI (blunt-ended) sites of pcDNA-1-neo.
**The HindIII-XbaI fragment of the pcDNA-1-neo polylinker is replaced with a synthetic fragment which destroys the original XbaI site and introduces several unique sites (HindIII-BamHI-XbaI-XhoI-SalI).
#Also may be created by an alternative strategy using the same pSK(+) plasmids.

TABLE 4

"Secretase-Minus" APP—REP Constructs
Engineered by Oligonucleotide-Directed Mutagenesis

| Plasmid Name | Mutation Identity | Mutated BAP Sequence Compared to Wild Type* | | | | | | | | Percent** Secretion |
|---|---|---|---|---|---|---|---|---|---|---|
| | | 14 | 15 | 16 | ¦ | 17 | 18 | 19 | 20 | |
| pCLL602 | BAP* | CAT | CAA | AAA | ¦ | TTG | GTG | TTC | TTT | 100 |
| | | H | Q | K | ¦ | L | V | F | F | |
| pCCLL608 | BAP-16KE | CAT | CAA | GAG | ¦ | TTG | GTG | TTC | TTT | 0 |
| | | H | Q | E | ¦ | L | V | F | F | |
| pCCLL609 | BAP-16KV | CAT | CAA | GTG | ¦ | TTG | GTG | TTC | TTT | 10–20 |
| | | H | Q | E | ¦ | L | V | F | F | |
| pCCLL610 | BAP-19FP | CAT | CAA | AAA | ¦ | TTG | GTG | CCG | TTT | 10–20 |
| | | H | Q | K | ¦ | L | V | P | F | |

Notes:
*Wild-type BAP
**% secretion relative to wild type BAP sequence.

TABLE 5

APP—REP Constructs Modeling APP Mutations
Associated with Diseases Involving BAP Deposition

APP "717" MUTATIONS

| | | // [BAP] | // APP Transmembrane Domain // | | | | | | | |
|---|---|---|---|---|---|---|---|---|---|---|
| | | 711 | 712 | 713 | 714 | 715 | 716 | 717 | 718 | 719 |
| | | [40 | 41 | 42] | | | | | | |
| pCLL602 | APP* | GTC | ATA | GCG | ACA | GTG | ATC | GTC | ATC | ACC |
| | | V | I | A | T | V | I | V | I | T |
| pCLL611 | 717VI** | GTC | ATA | GCG | ACA | GTG | ATC | ATC | ATC | ACC |
| | | V | I | A | T | V | I | I | I | T |
| pCLL612 | 717VG@ | GTC | ATA | GCG | ACA | GTG | ATC | GGC | ATC | ACC |
| | | V | I | A | T | V | I | G | I | T |
| pCLL613 | 717VF$ | GTC | ATA | GCG | ACA | GTG | ATC | TTC | ATC | ACC |
| | | V | I | A | T | V | I | F | I | T |

DUTCH DISEASE

| | | | | | V (Secretase Clip) | | | | | | |
|---|---|---|---|---|---|---|---|---|---|---|---|
| | | 686 | 687 | ¦ | 688 | 689 | 690 | 691 | 692 | 693 | 694 |
| | | [15 | 16 | ¦ | 17 | 18 | 19 | 20 | 21 | 22 | 23] |
| pCLL602 | BAP* | CAA | AAA | ¦ | TTG | GTG | TTC | TTT | GCA | GAA | GAT |
| | | Q | K | ¦ | L | V | F | F | A | E | D |
| pCLL603* | $BAP_{E22Q}$ | CAA | AAA | ¦ | TTG | GTG | TTC | TTT | GCA | CAA | GAT |
| pCLL606# | | Q | K | ¦ | L | V | F | F | A | Q | D |

Notes:
#APP—REP-751 and -770 derived $BAP_{E22Q}$ constructs.
**Goate et al. (1991) Nature, 349:704–706; Yoshioka et al. (1991) BBRC 178:1141–1146; Naruse et al. (1991) Lancet 337:978–979.
@Chartier-Harlin et al. (1991) Nature 353:844–846.
$Murrell et al. (1991) Science 254:97–99.

What is claimed is:

1. A method for screening for a compound which reduces the formation of β-amyloid protein, comprising the steps of:

(a) measuring the amount of marker in a suitable medium containing transfected cells stably or transiently expressing a nucleic acid molecule encoding an amyloid precursor mutein comprising a nucleic acid sequence encoding a marker and a nucleic acid sequence encoding about 419 amino acid residues of the APP-695 isoform, about 475 amino acid residues of the APP-751 isoform or about 494 amino acid residues of the APP-770 isoform wherein the nucleic acid molecule is an XbaI-SalI fragment of the gene encoding an amyloid precursor protein isoform, (b) treating said cells with the compound, and (c) testing the medium for an increase in the amount of the marker.

2. The method of claim 1, wherein the compound is a protein kinase C activator.

3. The method of claim 1, which further comprises contacting the treated cells with an antibody directed to a portion of a β-amyloid protein domain sequence under suitable conditions to favor the formation of an antibody-antigen complex, and detecting the presence of any complex so formed.

4. A method for screening for a compound which reduces the formation of β-amyloid protein, comprising the steps of:

(a) measuring the amount of marker in a suitable medium containing transfected cells stably or transiently expressing a nucleic acid molecule encoding an amyloid precursor mutein comprising a nucleic acid sequence encoding a marker and a nucleic acid sequence encoding about 419 amino acid residues of the APP-695 isoform, about 475 amino acid residues of the APP-751 isoform or about 494 amino acid residues of the APP-770 isoform wherein the amino acid residues from position 11 to position 28 are deleted from the portion of the nucleic acid sequence encoding the β-amyloid protein domain and the nucleic acid molecule is an XbaI-SalI fragment of the gene encoding an amyloid precursor protein isoform, (b) treating said cells with the compound, and (c) testing the medium for an increase in the amount of the marker.

5. The method of claim 4, which further comprises contacting the treated cells with an antibody directed to a portion of a β-amyloid protein domain sequence under suitable conditions to favor the formation of antibody-antigen complex, and detecting the presence of any complex so formed.

6. A method for screening for a compound which reduces the formation of β-amyloid protein, comprising the steps of:

(a) measuring the amount of marker in a suitable medium containing transfected cells stably or transiently expressing a nucleic acid molecule encoding an amyloid precursor mutein comprising a nucleic acid sequence encoding a marker and a nucleic acid sequence encoding about 419 amino acid residues of the APP-695 isoform, about 475 amino acid residues of the APP-751 isoform or about 494 amino acid residues of the APP-770 isoform and in which an alanine substitution at a phosphorylation site within the cytoplasmic domain of an amyloid precursor protein is encoded, wherein the nucleic acid molecule is an XbaI-SalI fragment of the gene encoding an amyloid precursor protein isoform, (b) treating said cells with the compound, and (c) testing the medium for an increase in the amount of the marker.

7. The method of claim 6, which further comprises contacting the treated cells with an antibody directed to a portion of a β-amyloid protein domain sequence under suitable conditions to favor the formation of an antibody-antigen complex, and detecting the presence of any complex so formed.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
( A ) LENGTH: 11 amino acids
( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO:1:

Arg Pro Lys Pro Gln Gln Phe Phe Gly Leu Met
1 5 10

( 2 ) INFORMATION FOR SEQ ID NO:2:

( i ) SEQUENCE CHARACTERISTICS:
( A ) LENGTH: 5 amino acids
( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO:2:

Tyr Gly Gly Phe Met
1 5

( 2 ) INFORMATION FOR SEQ ID NO:3:

( i ) SEQUENCE CHARACTERISTICS:
( A ) LENGTH: 63 amino acids
( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO:3:

Thr Glu Glu Ile Ser Glu Val Lys Met Asp Ala Glu Phe Arg His Asp
1 5 10 15

Ser Gly Tyr Glu Val His His Gln Lys Leu Val Phe Phe Ala Gln Asp
20 25 30

Val Gly Ser Asn Lys Gly Ala Ile Ile Gly Leu Met Val Gly Gly Val
35 40 45

Val Ile Ala Thr Val Ile Val Ile Thr Val Met Leu Lys Lys Lys
50 55 60

( 2 ) INFORMATION FOR SEQ ID NO:4:

( i ) SEQUENCE CHARACTERISTICS:
( A ) LENGTH: 63 amino acids
( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO:4:

Thr Glu Glu Ile Ser Glu Val Lys Met Asp Ala Glu Phe Arg His Asp
1 5 10 15

-continued

| | | | | | | | | | | | | | | |
|---|---|---|---|---|---|---|---|---|---|---|---|---|---|---|
| Ser | Gly | Tyr | Glu<br>20 | Val | His | His | Gln | Lys<br>25 | Leu | Val | Phe | Phe | Ala<br>30 | Glu | Asp |
| Val | Gly | Ser<br>35 | Asn | Lys | Gly | Ala | Ile<br>40 | Ile | Gly | Leu | Met | Val<br>45 | Gly | Gly | Val |
| Val | Ile<br>50 | Ala | Thr | Val | Ile | Val<br>55 | Ile | Thr | Val | Met | Leu<br>60 | Lys | Lys | Lys | |

(2) INFORMATION FOR SEQ ID NO:5:

(i) SEQUENCE CHARACTERISTICS:
(A) LENGTH: 45 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:5:

| | | | | | | | | | | | | | | | |
|---|---|---|---|---|---|---|---|---|---|---|---|---|---|---|---|
| Thr<br>1 | Glu | Glu | Ile | Ser<br>5 | Glu | Val | Lys | Met | Asp<br>10 | Ala | Glu | Phe | Arg | His<br>15 | Asp |
| Ser | Ala | Tyr | Gly<br>20 | Ala | Ile | Ile | Gly | Leu<br>25 | Met | Val | Gly | Gly | Val<br>30 | Val | Ile |
| Ala | Thr | Val<br>35 | Ile | Val | Ile | Thr | Val<br>40 | Met | Leu | Lys | Lys | Lys<br>45 | | | |

(2) INFORMATION FOR SEQ ID NO:6:

(i) SEQUENCE CHARACTERISTICS:
(A) LENGTH: 8591 base pairs
(B) TYPE: nucleic acid
(C) STRANDEDNESS: double
(D) TOPOLOGY: circular (ii) MOLECULE TYPE: cDNA (ix) FEATURE:
(A) NAME/KEY: CDS
(B) LOCATION: 2393..3868

(xi) SEQUENCE DESCRIPTION: SEQ ID NO:6:

```
GGCGTAATCT GCTGCTTGCA AACAAAAAAA CCACCGCTAC CAGCGGTGGT TTGTTTGCCG    60
GATCAAGAGC TACCAACTCT TTTTCCGAAG GTAACTGGCT TCAGCAGAGC GCAGATACCA   120
AATACTGTCC TTCTAGTGTA GCCGTAGTTA GGCCACCACT TCAAGAACTC TGTAGCACCG   180
CCTACATACC TCGCTCTGCT AATCCTGTTA CCAGTGGCTG CTGCCAGTGG CGATAAGTCG   240
TGTCTTACCG GGTTGGACTC AAGACGATAG TTACCGGATA AGGCGCAGCG GTCGGGCTGA   300
ACGGGGGGTT CGTGCACACA GCCCAGCTTG GAGCGAACGA CCTACACCGA ACTGAGATAC   360
CTACAGCGTG AGCATTGAGA AAGCGCCACG CTTCCCGAAG GGAGAAAGGC GGACAGGTAT   420
CCGGTAAGCG GCAGGGTCGG AACAGGAGAG CGCACGAGGG AGCTTCCAGG GGGAAACGCC   480
TGGTATCTTT ATAGTCCTGT CGGGTTTCGC CACCTCTGAC TTGAGCGTCG ATTTTTGTGA   540
TGCTCGTCAG GGGGGCGGAG CCTATGGAAA AACGCCAGCA ACGCAAGCTA GCTTCTAGCT   600
AGAAATTGTA AACGTTAATA TTTTGTTAAA ATTCGCGTTA AATTTTTGTT AAATCAGCTC   660
ATTTTTTAAC CAATAGGCCG AAATCGGCAA AATCCCTTAT AAATCAAAAG AATAGCCCGA   720
GATAGGGTTG AGTGTTGTTC CAGTTTGGAA CAAGAGTCCA CTATTAAAGA ACGTGGACTC   780
CAACGTCAAA GGGCGAAAAA CCGTCTATCA GGGCGATGGC CGCCCACTAC GTGAACCATC   840
ACCCAAATCA AGTTTTTTGG GGTCGAGGTG CCGTAAAGCA CTAAATCGGA ACCCTAAAGG   900
GAGCCCCCGA TTTAGAGCTT GACGGGGAAA GCCGGCGAAC GTGGCGAGAA AGGAAGGGAA   960
```

-continued

GAAAGCGAAA GGAGCGGGCG CTAGGGCGCT GGCAAGTGTA GCGGTCACGC TGCGCGTAAC 1020

CACCACACCC GCCGCGCTTA ATGCGCCGCT ACAGGGCGCG TACTATGGTT GCTTTGACGA 1080

GACCGTATAA CGTGCTTTCC TCGTTGGAAT CAGAGCGGGA GCTAAACAGG AGGCCGATTA 1140

AAGGGATTTT AGACAGGAAC GGTACGCCAG CTGGATCACC GCGGTCTTTC TCAACGTAAC 1200

ACTTTACAGC GGCGCGTCAT TTGATATGAT GCGCCCCGCT TCCCGATAAG GGAGCAGGCC 1260

AGTAAAAGCA TTACCCGTGG TGGGGTTCCC GAGCGGCCAA AGGGAGCAGA CTCTAAATCT 1320

GCCGTCATCG ACTTCGAAGG TTCGAATCCT TCCCCCACCA CCATCACTTT CAAAAGTCCG 1380

AAAGAATCTG CTCCCTGCTT GTGTGTTGGA GGTCGCTGAG TAGTGCGCGA GTAAAATTTA 1440

AGCTACAACA AGGCAAGGCT TGACCGACAA TTGCATGAAG AATCTGCTTA GGGTTAGGCG 1500

TTTTGCGCTG CTTCGCGATG TACGGGCCAG ATATACGCGT TGACATTGAT TATTGACTAG 1560

TTATTAATAG TAATCAATTA CGGGGTCATT AGTTCATAGC CCATATATGG AGTTCCGCGT 1620

TACATAACTT ACGGTAAATG GCCCGCCTGG CTGACCGCCC AACGACCCCC GCCCATTGAC 1680

GTCAATAATG ACGTATGTTC CCATAGTAAC GCCAATAGGG ACTTTCCATT GACGTCAATG 1740

GGTGGACTAT TTACGGTAAA CTGCCCACTT GGCAGTACAT CAAGTGTATC ATATGCCAAG 1800

TACGCCCCCT ATTGACGTCA ATGACGGTAA ATGGCCCGCC TGGCATTATG CCCAGTACAT 1860

GACCTTATGG GACTTTCCTA CTTGGCAGTA CATCTACGTA TTAGTCATCG CTATTACCAT 1920

GGTGATGCGG TTTTGGCAGT ACATCAATGG GCGTGGATAG CGGTTTGACT CACGGGGATT 1980

TCCAAGTCTC CACCCCATTG ACGTCAATGG GAGTTTGTTT TGGCACCAAA ATCAACGGGA 2040

CTTTCCAAAA TGTCGTAACA ACTCCGCCCC ATTGACGCAA ATGGGCGGTA GGCGTGTACG 2100

GTGGGAGGTC TATATAAGCA GAGCTCTCTG GCTAACTAGA GAACCCACTG CTTAACTGGC 2160

TTATCGAAAT TAATACGACT CACTATAGGG AGACCGGAAG CTTGGGGATC CGCTCTAGAA 2220

CTAGTGGATC CCCCGGGCTG CAGGAATTCG GGGGGGGCAG CGGTAGGCGA GAGCACGCGG 2280

AGGAGCGTGC GCGGGGCCCC GGGAGACGGC GGCGGTGGCG GCGCGGGCAG AGCAAGGACG 2340

CGGCGGATCC CACTCGCACA GCAGCGCACT CGGTGCCCCG CGCAGGGTCG CG ATG 2395
Met
1

CTG CCC GGT TTG GCA CTG CTC CTG CTG GCC GCC TGG ACG GCT CGG GCG 2443
Leu Pro Gly Leu Ala Leu Leu Leu Leu Ala Ala Trp Thr Ala Arg Ala
5 10 15

CTG GAG GTA CCC ACT GAT GGT AAT GCT GGC CTG CTG GCT GAA CCC CAG 2491
Leu Glu Val Pro Thr Asp Gly Asn Ala Gly Leu Leu Ala Glu Pro Gln
20 25 30

ATT GCC ATG TTC TGT GGC AGA CTG AAC ATG CAC ATG AAT GTC CAG AAT 2539
Ile Ala Met Phe Cys Gly Arg Leu Asn Met His Met Asn Val Gln Asn
35 40 45

GGG AAG TGG GAT TCA GAT CCA TCA GGG ACC AAA ACC TGC ATT GAT ACC 2587
Gly Lys Trp Asp Ser Asp Pro Ser Gly Thr Lys Thr Cys Ile Asp Thr
50 55 60 65

AAG GAA GGC ATC CTG CAG TAT TGC CAA GAA GTC TAC CCT GAA CTG CAG 2635
Lys Glu Gly Ile Leu Gln Tyr Cys Gln Glu Val Tyr Pro Glu Leu Gln
70 75 80

ATC ACC AAT GTG GTA GAA GCC AAC CAA CCA GTG ACC ATC CAG AAC TGG 2683
Ile Thr Asn Val Val Glu Ala Asn Gln Pro Val Thr Ile Gln Asn Trp
85 90 95

TGC AAG CGG GGC CGC AAG CAG TGC AAG ACC CAT CCC CAC TTT GTG ATT 2731
Cys Lys Arg Gly Arg Lys Gln Cys Lys Thr His Pro His Phe Val Ile
100 105 110

-continued

CCC TAC CGC TGC TTA GTT GGT GAG TTT GTA AGT GAT GCC CTT CTC GTT 2779
Pro Tyr Arg Cys Leu Val Gly Glu Phe Val Ser Asp Ala Leu Leu Val
115 120 125

CCT GAC AAG TGC AAA TTC TTA CAC CAG GAG AGG ATG GAT GTT TGC GAA 2827
Pro Asp Lys Cys Lys Phe Leu His Gln Glu Arg Met Asp Val Cys Glu
130 135 140 145

ACT CAT CTT CAC TGG CAC ACC GTC GCC AAA GAG ACA TGC AGT GAG AAG 2875
Thr His Leu His Trp His Thr Val Ala Lys Glu Thr Cys Ser Glu Lys
150 155 160

AGT ACC AAC TTG CAT GAC TAC GGC ATG TTG CTG CCC TGC GGA ATT GAC 2923
Ser Thr Asn Leu His Asp Tyr Gly Met Leu Leu Pro Cys Gly Ile Asp
165 170 175

AAG TTC CGA GGG GTA GAG TTT GTG TGT TGC CCA CTG GCT GAA GAA AGT 2971
Lys Phe Arg Gly Val Glu Phe Val Cys Cys Pro Leu Ala Glu Glu Ser
180 185 190

GAC AAT GTG GAT TCT GCT GAT GCG GAG GAG GAT GAC TCG GAT GTC TGG 3019
Asp Asn Val Asp Ser Ala Asp Ala Glu Glu Asp Asp Ser Asp Val Trp
195 200 205

TGG GGC GGA GCA GAC ACA GAC TAT GCA GAT GGG AGT GAA GAC AAA GTA 3067
Trp Gly Gly Ala Asp Thr Asp Tyr Ala Asp Gly Ser Glu Asp Lys Val
210 215 220 225

GTA GAA GTA GCA GAG GAG GAA GAA GTG GCT GAG GTG GAA GAA GAA GAA 3115
Val Glu Val Ala Glu Glu Glu Glu Val Ala Glu Val Glu Glu Glu Glu
230 235 240

GCC GAT GAT GAC GAG GAC GAT GAG GAT GGT GAT GAG GTA GAG GAA GAG 3163
Ala Asp Asp Asp Glu Asp Asp Glu Asp Gly Asp Glu Val Glu Glu Glu
245 250 255

GCT GAG GAA CCC TAC GAA GAA GCC ACA GAG AGA ACC ACC AGC ATT GCC 3211
Ala Glu Glu Pro Tyr Glu Glu Ala Thr Glu Arg Thr Thr Ser Ile Ala
260 265 270

ACC ACC ACC ACC ACC ACC ACA GAG TCT GTG GAA GAG GTG GTT CGA GAG 3259
Thr Thr Thr Thr Thr Thr Thr Glu Ser Val Glu Glu Val Val Arg Glu
275 280 285

GTG TGC TCT GAA CAA GCC GAG ACG GGG CCG TGC CGA GCA ATG ATC TCC 3307
Val Cys Ser Glu Gln Ala Glu Thr Gly Pro Cys Arg Ala Met Ile Ser
290 295 300 305

CGC TGG TAC TTT GAT GTG ACT GAA GGG AAG TGT GCC CCA TTC TTT TAC 3355
Arg Trp Tyr Phe Asp Val Thr Glu Gly Lys Cys Ala Pro Phe Phe Tyr
310 315 320

GGC GGA TGT GGC GGC AAC CGG AAC AAC TTT GAC ACA GAA GAG TAC TGC 3403
Gly Gly Cys Gly Gly Asn Arg Asn Asn Phe Asp Thr Glu Glu Tyr Cys
325 330 335

ATG GCC GTG TGT GGC AGC GCC ATT CCT ACA ACA GCA GCC AGT ACC CCT 3451
Met Ala Val Cys Gly Ser Ala Ile Pro Thr Thr Ala Ala Ser Thr Pro
340 345 350

GAT GCC GTT GAC AAG TAT CTC GAG CGG CCC AAG CCC CAG CAG TTC TTT 3499
Asp Ala Val Asp Lys Tyr Leu Glu Arg Pro Lys Pro Gln Gln Phe Phe
355 360 365

GGC CTG ATG GGA AGC TTG ACA AAT ATC AAG ACG GAG GAG ATC TCT GAA 3547
Gly Leu Met Gly Ser Leu Thr Asn Ile Lys Thr Glu Glu Ile Ser Glu
370 375 380 385

GTG AAG ATG GAT GCA GAA TTC CGA CAT GAC TCA GGA TAT GAA GTT CAT 3595
Val Lys Met Asp Ala Glu Phe Arg His Asp Ser Gly Tyr Glu Val His
390 395 400

CAT CAA AAA TTG GTG TTC TTT GCA GAA GAT GTG GGT TCA AAC AAA GGT 3643
His Gln Lys Leu Val Phe Phe Ala Glu Asp Val Gly Ser Asn Lys Gly
405 410 415

GCA ATC ATT GGA CTC ATG GTG GGC GGT GTT GTC ATA GCG ACA GTG ATC 3691
Ala Ile Ile Gly Leu Met Val Gly Gly Val Val Ile Ala Thr Val Ile
420 425 430

-continued

```
GTC ATC ACC TTG GTG ATG CTG AAG AAG AAA CAG TAC ACA TCC ATT CAT      3739
Val Ile Thr Leu Val Met Leu Lys Lys Lys Gln Tyr Thr Ser Ile His
    435                 440                 445

CAT GGT GTG GTG GAG GTT GAC GCC GCT GTC ACC CCA GAG GAG CGC CAC      3787
His Gly Val Val Glu Val Asp Ala Ala Val Thr Pro Glu Glu Arg His
450                 455                 460                 465

CTG TCC AAG ATG CAG CAG AAC GGC TAC GAA AAT CCA ACC TAC AAG TTC      3835
Leu Ser Lys Met Gln Gln Asn Gly Tyr Glu Asn Pro Thr Tyr Lys Phe
                470                 475                 480

TTT GAG CAG ATG CAG AAC TAT GGG GGC TTC ATG TAGGATCCAT ATATAGGGCC    3888
Phe Glu Gln Met Gln Asn Tyr Gly Gly Phe Met
            485                 490

CGGGTTATAA TTACCTCAGG TCGACCTAGA GGGCCCTATT CTATAGTGTC ACCTAAATGC    3948

TAGAGGATCT TTGTGAAGGA ACCTTACTTC TGTGGTGTGA CATAATTGGA CAAACTACCT    4008

ACAGAGATTT AAAGCTCTAA GGTAAATATA AAATTTTTAA GTGTATAATG TGTTAAACTA    4068

CTGATTCTAA TTGTTTGTGT ATTTTAGATT CCAACCTATG GAACTGATGA ATGGGAGCAG    4128

TGGTGGAATG CCTTTAATGA GGAAAACCTG TTTTGCTCAG AAGAAATGCC ATCTAGTGAT    4188

GATGAGGCTA CTGCTGACTC TCAACATTCT ACTCCTCCAA AAAAGAAGAG AAAGGTAGAA    4248

GACCCCAAGG ACTTTCCTTC AGAATTGCTA AGTTTTTTGA GTCATGCTGT GTTTAGTAAT    4308

AGAACTCTTG CTTGCTTTGC TATTTACACC ACAAAGGAAA AAGCTGCACT GCTATACAAG    4368

AAAATTATGG AAAAATATTT GATGTATAGT GCCTTGACTA GAGATCATAA TCAGCCATAC    4428

CACATTTGTA GAGGTTTTAC TTGCTTTAAA AAACCTCCCA CACCTCCCCC TGAACCTGAA    4488

ACATAAAATG AATGCAATTG TTGTTGTTAA CTTGTTTATT GCAGCTTATA ATGGTTACAA    4548

ATAAAGCAAT AGCATCACAA ATTTCACAAA TAAAGCATTT TTTTCACTGC ATTCTAGTTG    4608

TGGTTTGTCC AAACTCATCA ATGTATCTTA TCATGTCTGG ATCTCCCGAT CCCCTATGGT    4668

GCACTCTCAG TACAATCTGC TCTGATGCCG CATAGTTAAG CCAGTATCTG CTCCCTGCTT    4728

GTGTGTTGGA GGTCGCTGAG TAGTGCGCGA GCAAAATTTA AGCTACAACA AGGCAAGGCT    4788

TGACCGACAA TTGCATGAAG AATCTGCTTA GGGTTAGGCG TTTTGCGCTG CTTCGCGATG    4848

TACGGGCCAG ATATACGCGT ATCTGAGGGG ACTAGGGTGT GTTTAGGCGA AAAGCGGGGC    4908

TTCGGTTGTA CGCGGTTAGG AGTCCCCTCA GGATATAGTA GTTTCGCTTT TGCATAGGGA    4968

GGGGGAAATG TAGTCTTATG CAATACACTT GTAGTCTTGC AACATGGTAA CGATGAGTTA    5028

GCAACATGCC TTACAAGGAG AGAAAAAGCA CCGTGCATGC CGATTGGTGG AAGTAAGGTG    5088

GTACGATCGT GCCTTATTAG GAAGGCAACA GACAGGTCTG ACATGGATTG GACGAACCAC    5148

TGAATTCCGC ATTGCAGAGA TAATTGTATT TAAGTGCCTA GCTCGATACA ATAAACGCCA    5208

TTTGACCATT CACCACATTG GTGTGCACCT CCTAGCTTCA CGCTGCCGCA AGCACTCAGG    5268

GCGCAAGGGC TGCTAAAGGA AGCGGAACAC GTAGAAAGCC AGTCCGCAGA AACGGTGCTG    5328

ACCCCGGATG AATGTCAGCT ACTGGGCTAT CTGGACAAGG GAAAACGCAA GCGCAAAGAG    5388

AAAGCAGGTA GCTTGCAGTG GGCTTACATG GCGATAGCTA GACTGGGCGG TTTTATGGAC    5448

AGCAAGCGAA CCGGAATTGC CAGCTGGGGC GCCCTCTGGT AAGGTTGGGA AGCCCTGCAA    5508

AGTAAACTGG ATGGCTTTCT TGCCGCCAAG GATCTGATGG CGCAGGGGAT CAAGATCTGA    5568

TCAAGAGACA GGATGAGGAT CGTTTCGCAT GATTGAACAA GATGGATTGC ACGCAGGTTC    5628

TCCGGCCGCT TGGGTGGAGA GGCTATTCGG CTATGACTGG GCACAACAGA CAATCGGCTG    5688

CTCTGATGCC GCCGTGTTCC GGCTGTCAGC GCAGGGGCGC CCGGTTCTTT TTGTCAAGAC    5748

CGACCTGTCC GGTGCCCTGA ATGAACTGCA GGACGAGGCA GCGCGGCTAT CGTGGCTGGC    5808
```

-continued

| | | | | | | |
|---|---|---|---|---|---|---|
| CACGACGGGC | GTTCCTTGCG | CAGCTGTGCT | CGACGTTGTC | ACTGAAGCGG | GAAGGGACTG | 5868 |
| GCTGCTATTG | GGCGAAGTGC | CGGGGCAGGA | TCTCCTGTCA | TCTCACCTTG | CTCCTGCCGA | 5928 |
| GAAAGTATCC | ATCATGGCTG | ATGCAATGCG | GCGGCTGCAT | ACGCTTGATC | CGGCTACCTG | 5988 |
| CCCATTCGAC | CACCAAGCGA | AACATCGCAT | CGGCGAGCAC | GTACTCGGAT | GGAAGCCGGT | 6048 |
| CTTGTCGATC | AGGATGATCT | GGACGAAGAG | CATCAGGGGC | TCGCGCCAGC | CGAACTGTTC | 6108 |
| GCCAGGCTCA | AGGCGCGCAT | GCCCGACGGC | GAGGATCTCG | TCGTGACCCA | TGGCGATGCC | 6168 |
| TGCTTGCCGA | ATATCATGGT | GGAAAATGGC | CGCTTTTCTG | GATTCATCGA | CTGTGGCCGG | 6228 |
| CTGGGTGTGG | CGGACCGCTA | TCAGGACATA | GCGTTGGCTA | CCCGTGATAT | TGCTGAAGAG | 6288 |
| CTTGGCGGCG | AATGGGCTGA | CCGCTTCCTC | GTGCTTTACG | GTATCGCCGC | TCCCGATTCG | 6348 |
| CAGCGCATCG | CCTTCTATCG | CCTTCTTGAC | GAGTTCTTCT | GAGCGGGACT | CTGGGGTTCG | 6408 |
| AAATGACCGA | CCAAGCGACG | CCCAACCTGC | CATCACGAGA | TTTCGATTCC | ACCGCCGCCT | 6468 |
| TCTATGAAAG | GTTGGGCTTC | GGAATCGTTT | TCCGGGACGC | CGGCTGGATG | ATCCTCCAGC | 6528 |
| GCGGGGATCT | CATGCTGGAG | TTCTTCGCCC | ACCCCGGGCT | CGATCCCCTC | GCGAGTTGGT | 6588 |
| TCAGCTGCTG | CCTGAGGCTG | GACGACCTCG | CGGAGTTCTA | CCGGCAGTGC | AAATCCGTCG | 6648 |
| GCATCCAGGA | AACCAGCAGC | GGCTATCCGC | GCATCCATGC | CCCCGAACTG | CAGGAGTGGG | 6708 |
| GAGGCACGAT | GGCCGCTTTG | GTCCCGGATC | TTTGTGAAGG | AACCTTACTT | CTGTGGTGTG | 6768 |
| ACATAATTGG | ACAAACTACC | TACAGAGATT | TAAAGCTCTA | AGGTAAATAT | AAAATTTTTA | 6828 |
| AGTGTATAAT | GTGTTAAACT | ACTGATTCTA | ATTGTTTGTG | TATTTTAGAT | TCCAACCTAT | 6888 |
| GGAACTGATG | AATGGGAGCA | GTGGTGGAAT | GCCTTTAATG | AGGAAAACCT | GTTTTGCTCA | 6948 |
| GAAGAAATGC | CATCTAGTGA | TGATGAGGCT | ACTGCTGACT | CTCAACATTC | TACTCCTCCA | 7008 |
| AAAAAGAAGA | GAAAGGTAGA | AGACCCCAAG | GACTTTCCTT | CAGAATTGCT | AAGTTTTTTG | 7068 |
| AGTCATGCTG | TGTTTAGTAA | TAGAACTCTT | GCTTGCTTTG | CTATTTACAC | CACAAAGGAA | 7128 |
| AAAGCTGCAC | TGCTATACAA | GAAAATTATG | GAAAAATATT | CTGTAACCTT | TATAAGTAGG | 7188 |
| CATAACAGTT | ATAATCATAA | CATACTGTTT | TTTCTTACTC | CACACAGGCA | TAGAGTGTCT | 7248 |
| GCTATTAATA | ACTATGCTCA | AAAATTGTGT | ACCTTTAGCT | TTTTAATTTG | TAAAGGGGTT | 7308 |
| AATAAGGATT | ATTTGATGTA | TAGTGCCTTG | ACTAGAGATC | ATAATCAGCC | ATACCACATT | 7368 |
| TGTAGAGGTT | TTACTTGCTT | TAAAAAACCT | CCCACACCTC | CCCCTGAACC | TGAAACATAA | 7428 |
| AATGAATGCA | ATTGTTGTTG | TTAACTTGTT | TATTGCAGCT | TATAATGGTT | ACAAATAAAG | 7488 |
| CAATAGCATC | ACAAATTTCA | CAAATAAAGC | ATTTTTTTCA | CTGCATTCTA | GTTGTGGTTT | 7548 |
| GTCCAAACTC | ATCAATGTAT | CTTATCATGT | CTGGATCGAT | CCCGCCATGG | TATCAACGCC | 7608 |
| ATATTTCTAT | TTACAGTAGG | GACCTCTTCG | TTGTGTAGGT | ACCGCTGTAT | TCCTAGGGAA | 7668 |
| ATAGTAGAGG | CACCTTGAAC | TGTCTGCATC | AGCCATATAG | CCCCCGCTGT | TCGACTTACA | 7728 |
| AACACAGGCA | CAGTACTGAC | AAACCCATAC | ACCTCCTCTG | AAATACCCAT | AGTTGCTAGG | 7788 |
| GCTGTCTCCG | AACTCATTAC | ACCCTCCAAA | GTCAGAGCTG | TAATTTCGCC | ATCAAGGGCA | 7848 |
| GCGAGGGCTT | CTCCAGATAA | AATAGCTTCT | GCCGAGAGTC | CCGTAAGGGT | AGACACTTCA | 7908 |
| GCTAATCCCT | CGATGAGGTC | TACTAGAATA | GTCAGTGCGG | CTCCCATTTT | GAAAATTCAC | 7968 |
| TTACTTGATC | AGCTTCAGAA | GATGGCGGAG | GGCCTCCAAC | ACAGTAATTT | TCCTCCCGAC | 8028 |
| TCTTAAAATA | GAAAATGTCA | AGTCAGTTAA | GCAGGAAGTG | GACTAACTGA | CGCAGCTGGC | 8088 |
| CGTGCGACAT | CCTCTTTTAA | TTAGTTGCTA | GGCAACGCCC | TCCAGAGGGC | GTGTGGTTTT | 8148 |
| GCAAGAGGAA | GCAAAAGCCT | CTCCACCCAG | GCCTAGAATG | TTTCCACCCA | ATCATTACTA | 8208 |

-continued

```
TGACAACAGC TGTTTTTTTT AGTATTAAGC AGAGGCCGGG GACCCCTGGG CCCGCTTACT 8268

CTGGAGAAAA AGAAGAGAGG CATTGTAGAG GCTTCCAGAG GCAACTTGTC AAAACAGGAC 8328

TGCTTCTATT TCTGTCACAC TGTCTGGCCC TGTCACAAGG TCCAGCACCT CCATACCCCC 8388

TTTAATAAGC AGTTTGGGAA CGGGTGCGGG TCTTACTCCG CCCATCCCGC CCCTAACTCC 8448

GCCCAGTTCC GCCCATTCTC CGCCCCATGG CTGACTAATT TTTTTTATTT ATGCAGAGGC 8508

CGAGGCCGCC TCGGCCTCTG AGCTATTCCA GAAGTAGTGA GGAGGCTTTT TTGGAGGCCT 8568

AGGCTTTTGC AAAAAGCTAA TTC 8591
```

( 2 ) INFORMATION FOR SEQ ID NO:7:

( i ) SEQUENCE CHARACTERISTICS:
( A ) LENGTH: 492 amino acids
( B ) TYPE: amino acid
( D ) TOPOLOGY: linear ( i i ) MOLECULE TYPE: protein ( x i ) SEQUENCE DESCRIPTION: SEQ ID NO:7:

```
Met Leu Pro Gly Leu Ala Leu Leu Leu Leu Ala Ala Trp Thr Ala Arg
  1               5                  10                  15

Ala Leu Glu Val Pro Thr Asp Gly Asn Ala Gly Leu Leu Ala Glu Pro
             20                  25                  30

Gln Ile Ala Met Phe Cys Gly Arg Leu Asn Met His Met Asn Val Gln
         35                  40                  45

Asn Gly Lys Trp Asp Ser Asp Pro Ser Gly Thr Lys Thr Cys Ile Asp
     50                  55                  60

Thr Lys Glu Gly Ile Leu Gln Tyr Cys Gln Glu Val Tyr Pro Glu Leu
 65                  70                  75                      80

Gln Ile Thr Asn Val Val Glu Ala Asn Gln Pro Val Thr Ile Gln Asn
                 85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                     160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Glu Val Ala Glu Val Glu Glu Glu
225                 230                 235                     240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285
```

-continued

Glu Val Cys Ser Glu Gln Ala Glu Thr Gly Pro Cys Arg Ala Met Ile
290 295 300

Ser Arg Trp Tyr Phe Asp Val Thr Glu Gly Lys Cys Ala Pro Phe Phe
305 310 315 320

Tyr Gly Gly Cys Gly Gly Asn Arg Asn Asn Phe Asp Thr Glu Glu Tyr
325 330 335

Cys Met Ala Val Cys Gly Ser Ala Ile Pro Thr Thr Ala Ala Ser Thr
340 345 350

Pro Asp Ala Val Asp Lys Tyr Leu Glu Arg Pro Lys Pro Gln Gln Phe
355 360 365

Phe Gly Leu Met Gly Ser Leu Thr Asn Ile Lys Thr Glu Glu Ile Ser
370 375 380

Glu Val Lys Met Asp Ala Glu Phe Arg His Asp Ser Gly Tyr Glu Val
385 390 395 400

His His Gln Lys Leu Val Phe Phe Ala Glu Asp Val Gly Ser Asn Lys
405 410 415

Gly Ala Ile Ile Gly Leu Met Val Gly Gly Val Val Ile Ala Thr Val
420 425 430

Ile Val Ile Thr Leu Val Met Leu Lys Lys Lys Gln Tyr Thr Ser Ile
435 440 445

His His Gly Val Val Glu Val Asp Ala Ala Val Thr Pro Glu Glu Arg
450 455 460

His Leu Ser Lys Met Gln Gln Asn Gly Tyr Glu Asn Pro Thr Tyr Lys
465 470 475 480

Phe Phe Glu Gln Met Gln Asn Tyr Gly Gly Phe Met
485 490

( 2 ) INFORMATION FOR SEQ ID NO:8:

( i ) SEQUENCE CHARACTERISTICS:
( A ) LENGTH: 8591 base pairs
( B ) TYPE: nucleic acid
( C ) STRANDEDNESS: double
( D ) TOPOLOGY: circular ( i i ) MOLECULE TYPE: cDNA ( i x ) FEATURE:
( A ) NAME/KEY: CDS
( B ) LOCATION: 2393..3853

( x i ) SEQUENCE DESCRIPTION: SEQ ID NO:8:

GGCGTAATCT GCTGCTTGCA AACAAAAAAA CCACCGCTAC CAGCGGTGGT TTGTTTGCCG 60

GATCAAGAGC TACCAACTCT TTTTCCGAAG GTAACTGGCT TCAGCAGAGC GCAGATACCA 120

AATACTGTCC TTCTAGTGTA GCCGTAGTTA GGCCACCACT TCAAGAACTC TGTAGCACCG 180

CCTACATACC TCGCTCTGCT AATCCTGTTA CCAGTGGCTG CTGCCAGTGG CGATAAGTCG 240

TGTCTTACCG GGTTGGACTC AAGACGATAG TTACCGGATA AGGCGCAGCG GTCGGGCTGA 300

ACGGGGGGTT CGTGCACACA GCCCAGCTTG GAGCGAACGA CCTACACCGA ACTGAGATAC 360

CTACAGCGTG AGCATTGAGA AAGCGCCACG CTTCCCGAAG GGAGAAAGGC GGACAGGTAT 420

CCGGTAAGCG GCAGGGTCGG AACAGGAGAG CGCACGAGGG AGCTTCCAGG GGGAAACGCC 480

TGGTATCTTT ATAGTCCTGT CGGGTTTCGC CACCTCTGAC TTGAGCGTCG ATTTTTGTGA 540

TGCTCGTCAG GGGGGCGGAG CCTATGGAAA AACGCCAGCA ACGCAAGCTA GCTTCTAGCT 600

AGAAATTGTA AACGTTAATA TTTTGTTAAA ATTCGCGTTA AATTTTTGTT AAATCAGCTC 660

ATTTTTTAAC CAATAGGCCG AAATCGGCAA AATCCCTTAT AAATCAAAAG AATAGCCCGA 720

-continued

```
GATAGGGTTG AGTGTTGTTC CAGTTTGGAA CAAGAGTCCA CTATTAAAGA ACGTGGACTC   780

CAACGTCAAA GGGCGAAAAA CCGTCTATCA GGGCGATGGC CGCCCACTAC GTGAACCATC   840

ACCCAAATCA AGTTTTTTGG GGTCGAGGTG CCGTAAAGCA CTAAATCGGA ACCCTAAAGG   900

GAGCCCCCGA TTTAGAGCTT GACGGGGAAA GCCGGCGAAC GTGGCGAGAA AGGAAGGGAA   960

GAAAGCGAAA GGAGCGGGCG CTAGGGCGCT GGCAAGTGTA GCGGTCACGC TGCGCGTAAC  1020

CACCACACCC GCCGCGCTTA ATGCGCCGCT ACAGGGCGCG TACTATGGTT GCTTTGACGA  1080

GACCGTATAA CGTGCTTTCC TCGTTGGAAT CAGAGCGGGA GCTAAACAGG AGGCCGATTA  1140

AAGGGATTTT AGACAGGAAC GGTACGCCAG CTGGATCACC GCGGTCTTTC TCAACGTAAC  1200

ACTTTACAGC GGCGCGTCAT TTGATATGAT GCGCCCCGCT TCCCGATAAG GGAGCAGGCC  1260

AGTAAAAGCA TTACCCGTGG TGGGGTTCCC GAGCGGCCAA AGGGAGCAGA CTCTAAATCT  1320

GCCGTCATCG ACTTCGAAGG TTCGAATCCT TCCCCCACCA CCATCACTTT CAAAAGTCCG  1380

AAAGAATCTG CTCCCTGCTT GTGTGTTGGA GGTCGCTGAG TAGTGCGCGA GTAAAATTTA  1440

AGCTACAACA AGGCAAGGCT TGACCGACAA TTGCATGAAG AATCTGCTTA GGGTTAGGCG  1500

TTTTGCGCTG CTTCGCGATG TACGGGCCAG ATATACGCGT TGACATTGAT TATTGACTAG  1560

TTATTAATAG TAATCAATTA CGGGGTCATT AGTTCATAGC CCATATATGG AGTTCCGCGT  1620

TACATAACTT ACGGTAAATG GCCCGCCTGG CTGACCGCCC AACGACCCCC GCCCATTGAC  1680

GTCAATAATG ACGTATGTTC CCATAGTAAC GCCAATAGGG ACTTTCCATT GACGTCAATG  1740

GGTGGACTAT TTACGGTAAA CTGCCCACTT GGCAGTACAT CAAGTGTATC ATATGCCAAG  1800

TACGCCCCCT ATTGACGTCA ATGACGGTAA ATGGCCCGCC TGGCATTATG CCCAGTACAT  1860

GACCTTATGG GACTTTCCTA CTTGGCAGTA CATCTACGTA TTAGTCATCG CTATTACCAT  1920

GGTGATGCGG TTTTGGCAGT ACATCAATGG GCGTGGATAG CGGTTTGACT CACGGGGATT  1980

TCCAAGTCTC CACCCCATTG ACGTCAATGG GAGTTTGTTT TGGCACCAAA ATCAACGGGA  2040

CTTTCCAAAA TGTCGTAACA ACTCCGCCCC ATTGACGCAA ATGGGCGGTA GGCGTGTACG  2100

GTGGGAGGTC TATATAAGCA GAGCTCTCTG GCTAACTAGA GAACCCACTG CTTAACTGGC  2160

TTATCGAAAT TAATACGACT CACTATAGGG AGACCGGAAG CTTGGGGATC CGCTCTAGAA  2220

CTAGTGGATC CCCCGGGCTG CAGGAATTCG GGGGGGGCAG CGGTAGGCGA GAGCACGCGG  2280

AGGAGCGTGC GCGGGGCCCC GGGAGACGGC GGCGGTGGCG GCGCGGGCAG AGCAAGGACG  2340

CGGCGGATCC CACTCGCACA GCAGCGCACT CGGTGCCCCG CGCAGGGTCG CG ATG      2395
                                                          Met
                                                            1

CTG CCC GGT TTG GCA CTG CTC CTG CTG GCC GCC TGG ACG GCT CGG GCG    2443
Leu Pro Gly Leu Ala Leu Leu Leu Leu Ala Ala Trp Thr Ala Arg Ala
            5                  10                  15

CTG GAG GTA CCC ACT GAT GGT AAT GCT GGC CTG CTG GCT GAA CCC CAG    2491
Leu Glu Val Pro Thr Asp Gly Asn Ala Gly Leu Leu Ala Glu Pro Gln
        20                  25                  30

ATT GCC ATG TTC TGT GGC AGA CTG AAC ATG CAC ATG AAT GTC CAG AAT    2539
Ile Ala Met Phe Cys Gly Arg Leu Asn Met His Met Asn Val Gln Asn
    35                  40                  45

GGG AAG TGG GAT TCA GAT CCA TCA GGG ACC AAA ACC TGC ATT GAT ACC    2587
Gly Lys Trp Asp Ser Asp Pro Ser Gly Thr Lys Thr Cys Ile Asp Thr
50                  55                  60                  65

AAG GAA GGC ATC CTG CAG TAT TGC CAA GAA GTC TAC CCT GAA CTG CAG    2635
Lys Glu Gly Ile Leu Gln Tyr Cys Gln Glu Val Tyr Pro Glu Leu Gln
                70                  75                  80

ATC ACC AAT GTG GTA GAA GCC AAC CAA CCA GTG ACC ATC CAG AAC TGG    2683
```

-continued

```
Ile  Thr  Asn  Val  Val  Glu  Ala  Asn  Gln  Pro  Val  Thr  Ile  Gln  Asn  Trp
               85                       90                       95

TGC  AAG  CGG  GGC  CGC  AAG  CAG  TGC  AAG  ACC  CAT  CCC  CAC  TTT  GTG  ATT     2731
Cys  Lys  Arg  Gly  Arg  Lys  Gln  Cys  Lys  Thr  His  Pro  His  Phe  Val  Ile
          100                      105                      110

CCC  TAC  CGC  TGC  TTA  GTT  GGT  GAG  TTT  GTA  AGT  GAT  GCC  CTT  CTC  GTT     2779
Pro  Tyr  Arg  Cys  Leu  Val  Gly  Glu  Phe  Val  Ser  Asp  Ala  Leu  Leu  Val
     115                      120                      125

CCT  GAC  AAG  TGC  AAA  TTC  TTA  CAC  CAG  GAG  AGG  ATG  GAT  GTT  TGC  GAA     2827
Pro  Asp  Lys  Cys  Lys  Phe  Leu  His  Gln  Glu  Arg  Met  Asp  Val  Cys  Glu
130                      135                      140                      145

ACT  CAT  CTT  CAC  TGG  CAC  ACC  GTC  GCC  AAA  GAG  ACA  TGC  AGT  GAG  AAG     2875
Thr  His  Leu  His  Trp  His  Thr  Val  Ala  Lys  Glu  Thr  Cys  Ser  Glu  Lys
                    150                      155                      160

AGT  ACC  AAC  TTG  CAT  GAC  TAC  GGC  ATG  TTG  CTG  CCC  TGC  GGA  ATT  GAC     2923
Ser  Thr  Asn  Leu  His  Asp  Tyr  Gly  Met  Leu  Leu  Pro  Cys  Gly  Ile  Asp
               165                      170                      175

AAG  TTC  CGA  GGG  GTA  GAG  TTT  GTG  TGT  TGC  CCA  CTG  GCT  GAA  GAA  AGT     2971
Lys  Phe  Arg  Gly  Val  Glu  Phe  Val  Cys  Cys  Pro  Leu  Ala  Glu  Glu  Ser
          180                      185                      190

GAC  AAT  GTG  GAT  TCT  GCT  GAT  GCG  GAG  GAG  GAT  GAC  TCG  GAT  GTC  TGG     3019
Asp  Asn  Val  Asp  Ser  Ala  Asp  Ala  Glu  Glu  Asp  Asp  Ser  Asp  Val  Trp
     195                      200                      205

TGG  GGC  GGA  GCA  GAC  ACA  GAC  TAT  GCA  GAT  GGG  AGT  GAA  GAC  AAA  GTA     3067
Trp  Gly  Gly  Ala  Asp  Thr  Asp  Tyr  Ala  Asp  Gly  Ser  Glu  Asp  Lys  Val
210                      215                      220                      225

GTA  GAA  GTA  GCA  GAG  GAG  GAA  GAA  GTG  GCT  GAG  GTG  GAA  GAA  GAA  GAA     3115
Val  Glu  Val  Ala  Glu  Glu  Glu  Glu  Val  Ala  Glu  Val  Glu  Glu  Glu  Glu
                    230                      235                      240

GCC  GAT  GAT  GAC  GAG  GAC  GAT  GAG  GAT  GGT  GAT  GAG  GTA  GAG  GAA  GAG     3163
Ala  Asp  Asp  Asp  Glu  Asp  Asp  Glu  Asp  Gly  Asp  Glu  Val  Glu  Glu  Glu
               245                      250                      255

GCT  GAG  GAA  CCC  TAC  GAA  GAA  GCC  ACA  GAG  AGA  ACC  ACC  AGC  ATT  GCC     3211
Ala  Glu  Glu  Pro  Tyr  Glu  Glu  Ala  Thr  Glu  Arg  Thr  Thr  Ser  Ile  Ala
          260                      265                      270

ACC  ACC  ACC  ACC  ACC  ACC  ACA  GAG  TCT  GTG  GAA  GAG  GTG  GTT  CGA  GAG     3259
Thr  Thr  Thr  Thr  Thr  Thr  Thr  Glu  Ser  Val  Glu  Glu  Val  Val  Arg  Glu
     275                      280                      285

GTG  TGC  TCT  GAA  CAA  GCC  GAG  ACG  GGG  CCG  TGC  CGA  GCA  ATG  ATC  TCC     3307
Val  Cys  Ser  Glu  Gln  Ala  Glu  Thr  Gly  Pro  Cys  Arg  Ala  Met  Ile  Ser
290                      295                      300                      305

CGC  TGG  TAC  TTT  GAT  GTG  ACT  GAA  GGG  AAG  TGT  GCC  CCA  TTC  TTT  TAC     3355
Arg  Trp  Tyr  Phe  Asp  Val  Thr  Glu  Gly  Lys  Cys  Ala  Pro  Phe  Phe  Tyr
                    310                      315                      320

GGC  GGA  TGT  GGC  GGC  AAC  CGG  AAC  AAC  TTT  GAC  ACA  GAA  GAG  TAC  TGC     3403
Gly  Gly  Cys  Gly  Gly  Asn  Arg  Asn  Asn  Phe  Asp  Thr  Glu  Glu  Tyr  Cys
               325                      330                      335

ATG  GCC  GTG  TGT  GGC  AGC  GCC  ATT  CCT  ACA  ACA  GCA  GCC  AGT  ACC  CCT     3451
Met  Ala  Val  Cys  Gly  Ser  Ala  Ile  Pro  Thr  Thr  Ala  Ala  Ser  Thr  Pro
          340                      345                      350

GAT  GCC  GTT  GAC  AAG  TAT  CTC  GAG  CGG  CCC  AAG  CCC  CAG  CAG  TTC  TTT     3499
Asp  Ala  Val  Asp  Lys  Tyr  Leu  Glu  Arg  Pro  Lys  Pro  Gln  Gln  Phe  Phe
     355                      360                      365

GGC  CTG  ATG  GGA  AGC  TTG  ACA  AAT  ATC  AAG  ACG  GAG  GAG  ATC  TCT  GAA     3547
Gly  Leu  Met  Gly  Ser  Leu  Thr  Asn  Ile  Lys  Thr  Glu  Glu  Ile  Ser  Glu
370                      375                      380                      385

GTG  AAG  ATG  GAT  GCA  GAA  TTC  CGA  CAT  GAC  TCA  GGA  TAT  GAA  GTT  CAT     3595
Val  Lys  Met  Asp  Ala  Glu  Phe  Arg  His  Asp  Ser  Gly  Tyr  Glu  Val  His
                    390                      395                      400

CAT  CAA  AAA  TTG  GTG  TTC  TTT  GCA  GAA  GAT  GTG  GGT  TCA  AAC  AAA  GGT     3643
```

-continued

```
His Gln Lys Leu Val Phe Phe Ala Glu Asp Val Gly Ser Asn Lys Gly
            405                     410                     415

GCA ATC ATT GGA CTC ATG GTG GGC GGT GTT GTC ATA GCG ACA GTG ATC      3691
Ala Ile Ile Gly Leu Met Val Gly Gly Val Val Ile Ala Thr Val Ile
        420                     425                     430

GTC ATC ACC TTG GTG ATG CTG AAG AAG AAA CAG TAC ACA TCC ATT CAT      3739
Val Ile Thr Leu Val Met Leu Lys Lys Lys Gln Tyr Thr Ser Ile His
    435                     440                     445

CAT GGT GTG GTG GAG GTT GAC GCC GCT GTC ACC CCA GAG GAG CGC CAC      3787
His Gly Val Val Glu Val Asp Ala Ala Val Thr Pro Glu Glu Arg His
450                     455                     460                     465

CTG TCC AAG ATG CAG CAG AAC GGC TAC GAA AAT CCA ACC TAC AAG TTC      3835
Leu Ser Lys Met Gln Gln Asn Gly Tyr Glu Asn Pro Thr Tyr Lys Phe
                470                     475                     480

TTT GAG CAG ATG CAG AAC TAGTGGGGCT TCATGTAGGA TCCATATATA             3883
Phe Glu Gln Met Gln Asn
            485

GGGCCCGGGT TATAATTACC TCAGGTCGAC CTAGAGGGCC CTATTCTATA GTGTCACCTA    3943

AATGCTAGAG GATCTTTGTG AAGGAACCTT ACTTCTGTGG TGTGACATAA TTGGACAAAC    4003

TACCTACAGA GATTTAAAGC TCTAAGGTAA ATATAAAATT TTTAAGTGTA TAATGTGTTA    4063

AACTACTGAT TCTAATTGTT TGTGTATTTT AGATTCCAAC CTATGGAACT GATGAATGGG    4123

AGCAGTGGTG GAATGCCTTT AATGAGGAAA ACCTGTTTTG CTCAGAAGAA ATGCCATCTA    4183

GTGATGATGA GGCTACTGCT GACTCTCAAC ATTCTACTCC TCCAAAAAAG AAGAGAAAGG    4243

TAGAAGACCC CAAGGACTTT CCTTCAGAAT TGCTAAGTTT TTTGAGTCAT GCTGTGTTTA    4303

GTAATAGAAC TCTTGCTTGC TTTGCTATTT ACACCACAAA GGAAAAAGCT GCACTGCTAT    4363

ACAAGAAAAT TATGGAAAAA TATTTGATGT ATAGTGCCTT GACTAGAGAT CATAATCAGC    4423

CATACCACAT TTGTAGAGGT TTTACTTGCT TTAAAAAACC TCCCACACCT CCCCCTGAAC    4483

CTGAAACATA AAATGAATGC AATTGTTGTT GTTAACTTGT TTATTGCAGC TTATAATGGT    4543

TACAAATAAA GCAATAGCAT CACAAATTTC ACAAATAAAG CATTTTTTTC ACTGCATTCT    4603

AGTTGTGGTT TGTCCAAACT CATCAATGTA TCTTATCATG TCTGGATCTC CCGATCCCCT    4663

ATGGTGCACT CTCAGTACAA TCTGCTCTGA TGCCGCATAG TTAAGCCAGT ATCTGCTCCC    4723

TGCTTGTGTG TTGGAGGTCG CTGAGTAGTG CGCGAGCAAA ATTTAAGCTA CAACAAGGCA    4783

AGGCTTGACC GACAATTGCA TGAAGAATCT GCTTAGGGTT AGGCGTTTTG CGCTGCTTCG    4843

CGATGTACGG GCCAGATATA CGCGTATCTG AGGGGACTAG GGTGTGTTTA GGCGAAAAGC    4903

GGGGCTTCGG TTGTACGCGG TTAGGAGTCC CCTCAGGATA TAGTAGTTTC GCTTTTGCAT    4963

AGGGAGGGGG AAATGTAGTC TTATGCAATA CACTTGTAGT CTTGCAACAT GGTAACGATG    5023

AGTTAGCAAC ATGCCTTACA AGGAGAGAAA AAGCACCGTG CATGCCGATT GGTGGAAGTA    5083

AGGTGGTACG ATCGTGCCTT ATTAGGAAGG CAACAGACAG GTCTGACATG GATTGGACGA    5143

ACCACTGAAT TCCGCATTGC AGAGATAATT GTATTTAAGT GCCTAGCTCG ATACAATAAA    5203

CGCCATTTGA CCATTCACCA CATTGGTGTG CACCTCCTAG CTTCACGCTG CCGCAAGCAC    5263

TCAGGGCGCA AGGGCTGCTA AAGGAAGCGG AACACGTAGA AAGCCAGTCC GCAGAAACGG    5323

TGCTGACCCC GGATGAATGT CAGCTACTGG GCTATCTGGA CAAGGGAAAA CGCAAGCGCA    5383

AAGAGAAAGC AGGTAGCTTG CAGTGGGCTT ACATGGCGAT AGCTAGACTG GGCGGTTTTA    5443

TGGACAGCAA GCGAACCGGA ATTGCCAGCT GGGGCGCCCT CTGGTAAGGT TGGGAAGCCC    5503

TGCAAAGTAA ACTGGATGGC TTTCTTGCCG CCAAGGATCT GATGGCGCAG GGGATCAAGA    5563

TCTGATCAAG AGACAGGATG AGGATCGTTT CGCATGATTG AACAAGATGG ATTGCACGCA    5623
```

-continued

```
GGTTCTCCGG CCGCTTGGGT GGAGAGGCTA TTCGGCTATG ACTGGGCACA ACAGACAATC 5683
GGCTGCTCTG ATGCCGCCGT GTTCCGGCTG TCAGCGCAGG GGCGCCCGGT TCTTTTTGTC 5743
AAGACCGACC TGTCCGGTGC CCTGAATGAA CTGCAGGACG AGGCAGCGCG GCTATCGTGG 5803
CTGGCCACGA CGGGCGTTCC TTGCGCAGCT GTGCTCGACG TTGTCACTGA AGCGGGAAGG 5863
GACTGGCTGC TATTGGGCGA AGTGCCGGGG CAGGATCTCC TGTCATCTCA CCTTGCTCCT 5923
GCCGAGAAAG TATCCATCAT GGCTGATGCA ATGCGGCGGC TGCATACGCT TGATCCGGCT 5983
ACCTGCCCAT TCGACCACCA AGCGAAACAT CGCATCGGCG AGCACGTACT CGGATGGAAG 6043
CCGGTCTTGT CGATCAGGAT GATCTGGACG AAGAGCATCA GGGGCTCGCG CCAGCCGAAC 6103
TGTTCGCCAG GCTCAAGGCG CGCATGCCCG ACGGCGAGGA TCTCGTCGTG ACCCATGGCG 6163
ATGCCTGCTT GCCGAATATC ATGGTGGAAA ATGGCCGCTT TTCTGGATTC ATCGACTGTG 6223
GCCGGCTGGG TGTGGCGGAC CGCTATCAGG ACATAGCGTT GGCTACCCGT GATATTGCTG 6283
AAGAGCTTGG CGGCGAATGG GCTGACCGCT TCCTCGTGCT TTACGGTATC GCCGCTCCCG 6343
ATTCGCAGCG CATCGCCTTC TATCGCCTTC TTGACGAGTT CTTCTGAGCG GGACTCTGGG 6403
GTTCGAAATG ACCGACCAAG CGACGCCCAA CCTGCCATCA CGAGATTTCG ATTCCACCGC 6463
CGCCTTCTAT GAAAGGTTGG GCTTCGGAAT CGTTTTCCGG GACGCCGGCT GGATGATCCT 6523
CCAGCGCGGG GATCTCATGC TGGAGTTCTT CGCCCACCCC GGGCTCGATC CCCTCGCGAG 6583
TTGGTTCAGC TGCTGCCTGA GGCTGGACGA CCTCGCGGAG TTCTACCGGC AGTGCAAATC 6643
CGTCGGCATC CAGGAAACCA GCAGCGGCTA TCCGCGCATC CATGCCCCCG AACTGCAGGA 6703
GTGGGGAGGC ACGATGGCCG CTTTGGTCCC GGATCTTTGT GAAGGAACCT TACTTCTGTG 6763
GTGTGACATA ATTGGACAAA CTACCTACAG AGATTTAAAG CTCTAAGGTA AATATAAAAT 6823
TTTTAAGTGT ATAATGTGTT AAACTACTGA TTCTAATTGT TTGTGTATTT TAGATTCCAA 6883
CCTATGGAAC TGATGAATGG GAGCAGTGGT GGAATGCCTT TAATGAGGAA AACCTGTTTT 6943
GCTCAGAAGA AATGCCATCT AGTGATGATG AGGCTACTGC TGACTCTCAA CATTCTACTC 7003
CTCCAAAAAA GAAGAGAAAG GTAGAAGACC CCAAGGACTT TCCTTCAGAA TTGCTAAGTT 7063
TTTTGAGTCA TGCTGTGTTT AGTAATAGAA CTCTTGCTTG CTTTGCTATT TACACCACAA 7123
AGGAAAAAGC TGCACTGCTA TACAAGAAAA TTATGGAAAA ATATTCTGTA ACCTTTATAA 7183
GTAGGCATAA CAGTTATAAT CATAACATAC TGTTTTTTCT TACTCCACAC AGGCATAGAG 7243
TGTCTGCTAT TAATAACTAT GCTCAAAAAT TGTGTACCTT TAGCTTTTTA ATTTGTAAAG 7303
GGGTTAATAA GGATTATTTG ATGTATAGTG CCTTGACTAG AGATCATAAT CAGCCATACC 7363
ACATTTGTAG AGGTTTTACT TGCTTTAAAA AACCTCCCAC ACCTCCCCCT GAACCTGAAA 7423
CATAAAATGA ATGCAATTGT TGTTGTTAAC TTGTTTATTG CAGCTTATAA TGGTTACAAA 7483
TAAAGCAATA GCATCACAAA TTTCACAAAT AAAGCATTTT TTTCACTGCA TTCTAGTTGT 7543
GGTTTGTCCA AACTCATCAA TGTATCTTAT CATGTCTGGA TCGATCCCGC CATGGTATCA 7603
ACGCCATATT TCTATTTACA GTAGGGACCT CTTCGTTGTG TAGGTACCGC TGTATTCCTA 7663
GGGAAATAGT AGAGGCACCT TGAACTGTCT GCATCAGCCA TATAGCCCCC GCTGTTCGAC 7723
TTACAAACAC AGGCACAGTA CTGACAAACC CATACACCTC CTCTGAAATA CCCATAGTTG 7783
CTAGGGCTGT CTCCGAACTC ATTACACCCT CCAAAGTCAG AGCTGTAATT TCGCCATCAA 7843
GGGCAGCGAG GGCTTCTCCA GATAAAATAG CTTCTGCCGA GAGTCCCGTA AGGGTAGACA 7903
CTTCAGCTAA TCCCTCGATG AGGTCTACTA GAATAGTCAG TGCGGCTCCC ATTTTGAAAA 7963
TTCACTTACT TGATCAGCTT CAGAAGATGG CGGAGGGCCT CCAACACAGT AATTTTCCTC 8023
```

-continued

```
CCGACTCTTA AAATAGAAAA TGTCAAGTCA GTTAAGCAGG AAGTGGACTA ACTGACGCAG 8083
CTGGCCGTGC GACATCCTCT TTTAATTAGT TGCTAGGCAA CGCCCTCCAG AGGGCGTGTG 8143
GTTTTGCAAG AGGAAGCAAA AGCCTCTCCA CCCAGGCCTA GAATGTTTCC ACCCAATCAT 8203
TACTATGACA ACAGCTGTTT TTTTTAGTAT TAAGCAGAGG CCGGGGACCC CTGGGCCCGC 8263
TTACTCTGGA GAAAAAGAAG AGAGGCATTG TAGAGGCTTC CAGAGGCAAC TTGTCAAAAC 8323
AGGACTGCTT CTATTTCTGT CACACTGTCT GGCCCTGTCA CAAGGTCCAG CACCTCCATA 8383
CCCCCTTTAA TAAGCAGTTT GGGAACGGGT GCGGGTCTTA CTCCGCCCAT CCCGCCCCTA 8443
ACTCCGCCCA GTTCCGCCCA TTCTCCGCCC CATGGCTGAC TAATTTTTTT TATTTATGCA 8503
GAGGCCGAGG CCGCCTCGGC CTCTGAGCTA TTCCAGAAGT AGTGAGGAGG CTTTTTTGGA 8563
GGCCTAGGCT TTTGCAAAAA GCTAATTC                                   8591
```

( 2 ) INFORMATION FOR SEQ ID NO:9:

( i ) SEQUENCE CHARACTERISTICS:
( A ) LENGTH: 487 amino acids
( B ) TYPE: amino acid
( D ) TOPOLOGY: linear ( i i ) MOLECULE TYPE: protein ( x i ) SEQUENCE DESCRIPTION: SEQ ID NO:9:

```
Met Leu Pro Gly Leu Ala Leu Leu Leu Leu Ala Ala Trp Thr Ala Arg
 1               5                  10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255
```

-continued

Glu Ala Glu Glu Pro Tyr Glu Glu Ala Thr Glu Arg Thr Thr Ser Ile
260 265 270

Ala Thr Thr Thr Thr Thr Thr Thr Glu Ser Val Glu Glu Val Val Arg
275 280 285

Glu Val Cys Ser Glu Gln Ala Glu Thr Gly Pro Cys Arg Ala Met Ile
290 295 300

Ser Arg Trp Tyr Phe Asp Val Thr Glu Gly Lys Cys Ala Pro Phe Phe
305 310 315 320

Tyr Gly Gly Cys Gly Gly Asn Arg Asn Asn Phe Asp Thr Glu Glu Tyr
325 330 335

Cys Met Ala Val Cys Gly Ser Ala Ile Pro Thr Thr Ala Ala Ser Thr
340 345 350

Pro Asp Ala Val Asp Lys Tyr Leu Glu Arg Pro Lys Pro Gln Gln Phe
355 360 365

Phe Gly Leu Met Gly Ser Leu Thr Asn Ile Lys Thr Glu Glu Ile Ser
370 375 380

Glu Val Lys Met Asp Ala Glu Phe Arg His Asp Ser Gly Tyr Glu Val
385 390 395 400

His His Gln Lys Leu Val Phe Phe Ala Glu Asp Val Gly Ser Asn Lys
405 410 415

Gly Ala Ile Ile Gly Leu Met Val Gly Gly Val Val Ile Ala Thr Val
420 425 430

Ile Val Ile Thr Leu Val Met Leu Lys Lys Lys Gln Tyr Thr Ser Ile
435 440 445

His His Gly Val Val Glu Val Asp Ala Ala Val Thr Pro Glu Glu Arg
450 455 460

His Leu Ser Lys Met Gln Gln Asn Gly Tyr Glu Asn Pro Thr Tyr Lys
465 470 475 480

Phe Phe Glu Gln Met Gln Asn
485

( 2 ) INFORMATION FOR SEQ ID NO:10:

( i ) SEQUENCE CHARACTERISTICS:
( A ) LENGTH: 47 amino acids
( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO:10:

Lys Lys Lys Gln Tyr Thr Ser Ile His His Gly Val Val Glu Val Asp
1 5 10 15

Ala Ala Val Thr Pro Glu Glu Arg His Leu Ser Lys Met Gln Gln Asn
20 25 30

Gly Tyr Glu Asn Pro Thr Tyr Lys Phe Phe Glu Gln Met Gln Asn
35 40 45

( 2 ) INFORMATION FOR SEQ ID NO:11:

( i ) SEQUENCE CHARACTERISTICS:
( A ) LENGTH: 47 amino acids
( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO:11:

-continued

Lys Lys Lys Gln Ala Thr Ser Ile His His Gly Val Val Glu Val Asp
1 5 10 15

Ala Ala Val Thr Pro Glu Glu Arg His Leu Ser Lys Met Gln Gln Asn
20 25 30

Gly Tyr Glu Asn Pro Thr Tyr Lys Phe Phe Glu Gln Met Gln Asn
35 40 45

( 2 ) INFORMATION FOR SEQ ID NO:12:

( i ) SEQUENCE CHARACTERISTICS:
( A ) LENGTH: 47 amino acids
( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO:12:

Lys Lys Lys Gln Tyr Ala Ser Ile His His Gly Val Val Glu Val Asp
1 5 10 15

Ala Ala Val Thr Pro Glu Glu Arg His Leu Ser Lys Met Gln Gln Asn
20 25 30

Gly Tyr Glu Asn Pro Thr Tyr Lys Phe Phe Glu Gln Met Gln Asn
35 40 45

( 2 ) INFORMATION FOR SEQ ID NO:13:

( i ) SEQUENCE CHARACTERISTICS:
( A ) LENGTH: 47 amino acids
( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO:13:

Lys Lys Lys Gln Tyr Thr Ala Ile His His Gly Val Val Glu Val Asp
1 5 10 15

Ala Ala Val Thr Pro Glu Glu Arg His Leu Ser Lys Met Gln Gln Asn
20 25 30

Gly Tyr Glu Asn Pro Thr Tyr Lys Phe Phe Glu Gln Met Gln Asn
35 40 45

( 2 ) INFORMATION FOR SEQ ID NO:14:

( i ) SEQUENCE CHARACTERISTICS:
( A ) LENGTH: 47 amino acids
( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO:14:

Lys Lys Lys Gln Tyr Thr Ser Ile His His Gly Val Val Glu Val Asp
1 5 10 15

Ala Ala Val Ala Pro Glu Glu Arg His Leu Ser Lys Met Gln Gln Asn
20 25 30

Gly Tyr Glu Asn Pro Thr Tyr Lys Phe Phe Glu Gln Met Gln Asn
35 40 45

( 2 ) INFORMATION FOR SEQ ID NO:15:

( i ) SEQUENCE CHARACTERISTICS:

( A ) LENGTH: 47 amino acids
( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO:15:

Lys Lys Lys Gln Tyr Thr Ser Ile His His Gly Val Val Glu Val Asp
1 5 10 15

Ala Ala Val Thr Pro Glu Glu Arg His Leu Ala Lys Met Gln Gln Asn
20 25 30

Gly Tyr Glu Asn Pro Thr Tyr Lys Phe Phe Glu Gln Met Gln Asn
35 40 45

( 2 ) INFORMATION FOR SEQ ID NO:16:

( i ) SEQUENCE CHARACTERISTICS:
( A ) LENGTH: 47 amino acids
( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO:16:

Lys Lys Lys Gln Tyr Thr Ser Ile His His Gly Val Val Glu Val Asp
1 5 10 15

Ala Ala Val Thr Pro Glu Glu Arg His Leu Ser Lys Met Gln Gln Asn
20 25 30

Gly Ala Glu Asn Pro Thr Tyr Lys Phe Phe Glu Gln Met Gln Asn
35 40 45

( 2 ) INFORMATION FOR SEQ ID NO:17:

( i ) SEQUENCE CHARACTERISTICS:
( A ) LENGTH: 47 amino acids
( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO:17:

Lys Lys Lys Gln Tyr Thr Ser Ile His His Gly Val Val Glu Val Asp
1 5 10 15

Ala Ala Val Thr Pro Glu Glu Arg His Leu Ser Lys Met Gln Gln Asn
20 25 30

Gly Tyr Glu Asn Pro Ala Tyr Lys Phe Phe Glu Gln Met Gln Asn
35 40 45

( 2 ) INFORMATION FOR SEQ ID NO:18:

( i ) SEQUENCE CHARACTERISTICS:
( A ) LENGTH: 47 amino acids
( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO:18:

Lys Lys Lys Gln Tyr Thr Ser Ile His His Gly Val Val Glu Val Asp
1 5 10 15

Ala Ala Val Thr Pro Glu Glu Arg His Leu Ser Lys Met Gln Gln Asn
20 25 30

-continued

| | | | | | | | | | | | | | | |
|---|---|---|---|---|---|---|---|---|---|---|---|---|---|---|
| Gly | Tyr | Glu | Asn | Pro | Thr | Ala | Lys | Phe | Phe | Glu | Gln | Met | Gln | Asn |
| | | 35 | | | | | 40 | | | | | 45 | | |

( 2 ) INFORMATION FOR SEQ ID NO:19:

( i ) SEQUENCE CHARACTERISTICS:
( A ) LENGTH: 42 amino acids
( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO:19:

| | | | | | | | | | | | | | | | |
|---|---|---|---|---|---|---|---|---|---|---|---|---|---|---|---|
| Asp | Ala | Glu | Phe | Arg | His | Asp | Ser | Gly | Tyr | Glu | Val | His | His | Gln | Lys |
| 1 | | | | 5 | | | | | 10 | | | | | 15 | |
| Leu | Val | Phe | Phe | Ala | Glu | Asp | Val | Gly | Ser | Asn | Lys | Gly | Ala | Ile | Ile |
| | | | 20 | | | | | 25 | | | | | 30 | | |
| Gly | Leu | Met | Val | Gly | Gly | Val | Val | Ile | Ala | | | | | | |
| | | 35 | | | | | 40 | | | | | | | | |